(12) United States Patent
Lucy et al.

(10) Patent No.: US 7,575,861 B2
(45) Date of Patent: Aug. 18, 2009

(54) COMPOSITIONS AND METHOD FOR ACCURATE EARLY PREGNANCY DIAGNOSIS

(75) Inventors: Matthew C. Lucy, Columbia, MO (US); Nagappan Mathialagan, Ballwin, MO (US)

(73) Assignees: Monsanto Technology LLC, St. Louis, MO (US); The Curators of the University of Missouri, Columbia, MO (US)

( * ) Notice: Subject to any disclaimer, the term of this patent is extended or adjusted under 35 U.S.C. 154(b) by 365 days.

(21) Appl. No.: 10/496,164

(22) PCT Filed: Nov. 20, 2002

(86) PCT No.: PCT/US02/37236

§ 371 (c)(1),
(2), (4) Date: Dec. 29, 2004

(87) PCT Pub. No.: WO03/043524

PCT Pub. Date: May 30, 2003

(65) Prior Publication Data

US 2006/0199235 A1    Sep. 7, 2006

Related U.S. Application Data

(60) Provisional application No. 60/331,822, filed on Nov. 20, 2001.

(51) Int. Cl.
*G01N 33/53* (2006.01)
(52) U.S. Cl. .................. 435/6; 435/7.9; 435/7.92; 436/65; 436/510; 436/814; 436/817
(58) Field of Classification Search .................. None
See application file for complete search history.

(56) References Cited

U.S. PATENT DOCUMENTS

| 4,271,140 A | 6/1981 | Bunting .................. 436/500 |
| 4,895,804 A | 1/1990 | Bostwick et al. ........ 435/240.27 |
| 6,869,770 B1 * | 3/2005 | Roberts et al. ............... 435/7.1 |
| 2001/0024799 A1 | 9/2001 | Jordan et al. ................. 435/7.9 |
| 2003/0073248 A1 | 4/2003 | Roth et al. .................. 436/510 |
| 2007/0184558 A1 | 8/2007 | Roth et al. .................. 436/510 |

FOREIGN PATENT DOCUMENTS

| WO | WO 00/06038 | 2/1999 |
| WO | WO 99/47934 | 9/1999 |

OTHER PUBLICATIONS

Ranilla et al, "Plasmatic profiles of pregnancy associated glycoprotein and progesterone levels during gestation in churra and merino sheep", Theriology (1994), 42(3), 537-45 (only abstract is provided).*

Szenci et al., "Evaluation of false ultrasonographic diagnoses in cows by measuring plasma levels of bovine pregnancy-associated glycoprotein," *Vet Rec.*, 142:304-306, 1998.

Avalle et al., "Development of monoclonal and polyclonal antibodies against bovine pregnancy-associated glycoproteins (PAG) for use as reagents in localization of PAG expression and for pregnancy detection," *Biology of Reproduction, Society for the Study of Reproduction*, 64(suppl. 1):341, 2001. Abstract.

Humblot et al., "Diagnosis of pregnancy by radioimmunoassay of a pregnancy-specific protein in the plasma of dairy cows," *Theriogenology*, 30(2):257-67, 1988.

Humblot et al., "Pregnancy-specific protein B, progesterone concentrations and embryonic mortality during early pregnancy in dairy cows," *J. Reprod. Fert.*, 83:215-23, 1988.

Humblot, "Protéines spécifiques de la gestation chez les ruminants," *Reprod. Nutr. Dévelop.*, 28(6B):1753-62, 1988.

Takahashi et al., "Simple purification procedure for bovine pregnancy-associated glycoprotein with pepstatin A-coupled affinity chromatography," *Journal of Reproduction and Fertility, Abstract Series*, 26:32, 2000. Abstract.

U.S. Appl. No. 10/655,547, filed Sep. 4, 2003, Roberts et al.

U.S. Appl. No. 09/273,164, filed Mar. 19, 1999, Roberts et al.

Green et al., "The establishment of an ELISA for the detection of pregnancy-associated glycoproteins (PAGs) in the serum of pregnant cows and heifers," *Theriogenology*, 63:1481-1503, 2005.

Atkinson et al., "Characterization of placentation-specific binucleate cell glycoproteins processing a novel carbohydrate," *J. Biol. Chem.*, 268(35):26679-26685, 1993.

Birch and Loh, "Homology cloning of aspartic proteases from an endocrine cell line using the polymerase chain reaction," *Biochem. Biophys. Res. Commun.*, 177(3):920-926, 1993.

Cameron and Malmo, "Evaluation of an ultrasonic Doppler probe for pregnancy diagnosis in cattle," *Austr. Vet. J.*, 70:109-111, 1993.

Davies, "The structure and function of the aspartic proteinases," *Ann. Rev. Biophys. Chem.*, 19:189-215, 1990.

Garabayo et al., "Caprine pregnancy-associated glycoproteins (PAG): Their cloning expression and evolutionary relationship to other PAG," *Mo. Reprod. Dev*, 57:311-322, 2000.

Gerrie et al., "Pregnancy-associated alpha-2 glycoprotein: development of a sensitive enzyme-linked immunoassay and comparison of serum concentrations in adults and children," *Clinical Chimica. Acta*, 155:51-60, 1986.

Green et al., "Bovine pregnancy-associated glycoproteins (PAG) exhibit distinct expression patterns during gestation," *Biol Reprod*, 60(Suppl 1):497, 1999.

(Continued)

*Primary Examiner*—Christopher L Chin
(74) *Attorney, Agent, or Firm*—Sonnenschein Nath & Rosenthal LLP

(57) ABSTRACT

The invention provides improved assays for detection of pregnancy. In the assays, pregnancy associated glycoproteins are analyzed in conjunction with progesterone analysis. The techniques of the invention overcome limitations in the prior art by reducing the rate of false positive results. The assays provided by the invention can be implemented to increase the efficiency of commercial animal breeding programs.

39 Claims, No Drawings

OTHER PUBLICATIONS

Green et al., "Identification of a family of Kunitz domain proteins expressed in bovine and ovine trophoblast," *Biol Reprod*, 58 (Suppl 1):310.

Green et al., "Identification of a new aspartic proteinase expressed by the outer chorionic cell layer of the equine placenta," *Biol. Reprod.*, 60:1069-1077, 1999.

Green et al., "Pregnancy-associated bovine and ovine glycoproteins exhibit spatially and temporally distinct expression patterns during pregnancy," *Biol. of Repro.*, 62:1624-1631, 2000.

Green et al., "Pregnancy-associated glycoproteins of the horse," *Biol Reprod*, 50 (Suppl 1):152, 1994.

Green et al., "Pregnancy-associated glycoproteins: A family of catalytically inactive aspartic proteinases," *Mol Biol Cell*, 6 (Suppl 1):454, 1995.

Green et al., "The establishment for an ELISA for the detection of pregnancy-associated glycoproteins (PAGs) in the serum of pregnant cows and heifers," Departments of Animal Sciences and Biochemistry, University of Missouri-Columbia.

Guillomot, "Cellular interactions during implantation in domestic ruminants," *J. Reprod. Fertil.*, 49(Supp.):39-51, 1995.

Guruprasad et al., "Comparative modeling and analysis of amino acid substitutions suggests that the family of pregnancy-associated glycoproteins includes both active and inactive aspartic proteinases," *Protein Engin.*, 9:849-856, 1996.

Haig, "Genetic conflicts in human pregnancy," *Rev. Biol.*, 68:495-532, 1993.

Hughes et al., "Adaptive diversification within a large family of recently duplicated, placentally expressed genes," *Proc. Natl. Acad. Sci., USA*, 97:3319-3323, 2000.

Inoue et al., *Aspergillus niger* var. *Macrospores* proteinase B. cDNA cloning, expression, and activation of the proteinases, *Aspartic Proteinases*, 581-587, 1995.

Ishiwata et al., "Characterization of gene expression profiles in early bovine pregnancy using a custom cDNA microarray," *Mol Reprod Dev.*, 65(1):9-18, 2003.

Karen et al., "Early pregnancy diagnosis in sheep by progesterone and pregnancy-associated glycoprotein tests," *Theriogenology*, 59:1941-1948, 2003.

King et al., "Development of the bovine placentome from days 20 to 29 of gestation," *J. Reprod. Gertil.*, 59:95-100, 1980.

Kiracofe et al., "Pregnancy-specific protein B in serum of postpartum beef cows," *J. Anim. Sci.*, 71:2199-2205, 1993.

Li et al., "Mutational analysis of the vesicular stomatitis virus glycoprotein G for membrane fusion domains," *J. Virol.*, 67(7):4070-4077, 1993.

Lu et al., "Direct radioimmunoassay of progesterone in saliva," *J. Immunoassay*, 18(2):149-63, 1997.

Mialon et al., "Detection of pregnancy by radioimmunoassay of a pregnancy serum protein (PSP60) in cattle," *Reprod. Nutr. Dev.*, 34:65-72, 1994.

Mialon et al., "Peripheral concentrations of a 60-kDa pregnancy serum protein during gestation and after calving and in relationship to embryonic mortality in cattle," *Reprod. Nutr. Dev.*, 33:269-282, 1993.

Patel et al., "Effect of fetal mass, number, and stage of gestation on pregnancy-specific protein B concentrations in the bovine," *Theriogenol.*, 44:827-833, 1995.

Patel et al., "Plasma bovine pregnancy-associated glycoprotein concentrations throughout gestation in relationship to fetal number in the cow," *Eur. J. Endoc.*, 137:423-428, 1997.

Roberts et al., "Glycoproteins of the aspartyl proteinase gene family secreted by the developing placenta," *Aspartic Prot., Struct., Funct., Biol., Biom., Impl.*, 231-240, 1995.

Roberts et al., "Maternal Recognition of pregnancy," *Biol. Reprod.*, 54:294-302, 1996.

Roberts et al., "New and atypical families of type I interferons in mammals: comparative functions, structures, and evolutionary relationships," *Prog. Nucl. Acid Res. Mol. Biol.*, 56:287-326, 1997.

Sasser et al., "Characterizations of pregnancy-specific protein B in cattle," *J. Reprod. Fertil.*, 37(suppl.):109-113, 1989.

Sasser et al., "Detection of pregnancy by radioimmunoassay of a novel pregnancy-specific protein in serum of cows and a profile of serum concentrations during gestation," *Biol. Reprod.*, 35(4):936-942, 1986.

Scott et al., "Serum levels of pregnancy-associated alpha2-glycoprotein during pregnancy in autoimmune thyroid disease: relationship to disease activity," *Clinical and Experimental Immunology*, 59:564-570, 1985.

Stanley et al., "Use of a new and rapid milk progesterone assay to monitor reproductive activity in the cow," *Veterinary Record*, 664-667, 1986.

Stefanakis et al., *Bull. Hellenic Vet. Med. Soc.*, 45:37-43, 1994.

Szafranska et al., Porcine pregnancy-associated glycoproteins: new members of the aspartic proteinase gene family expressed in trophectoderm, *Biol. Reprod.*, 53:21-28, 1995.

Szafranska et al., "Gene for porcine and bovine pregnancy-associated glycoprotein 2: Its structural organization and analysis of its promoter," *Mol. Reprod. De.v*, 66:137-146, 2001.

Szenci et al., "Evaluation of false ultrasonographic diagnoses in cows by measuring plasma levels of bovine pregnancy-associated glycoprotein 1," *Vet. Record*, 142(12):304-306, 1998.

Vienravi et al., "A direct radioimmunoassay for free progesterone in saliva," *J. Med. Assoc. Thai.*, 77(3):138-147, 1994.

Wedemayer, "Structural insights into the evolution of an antibody combining site," *Science*, 276(5319):1665-1669, 1997.

Wooding, "Current topic: the syneptitheliochorial placenta of ruminants: binucleate cell fusions and hormone production," *Placenta*, 13:101-113, 1992.

Xie et al., "A novel glycoprotein of the aspartic proteinase gene family expressed in bovine placental trophectoderm," *Biol. Reprod.*, 51:1145-1153, 1994.

Xie et al., "Identification of the major pregnancy-specific antigens of cattle and sheep as inactive members of the aspartic proteinase family," *Proc. Natl. Acad. Sci., USA*, 88:10247-10251, 1991.

Xie et al., "Multiple pregnancy-associated glycoproteins are secreted by day 100 ovine placental tissue," *Biol. Reprod.*, 57:1384-1393, 1997.

Xie et al., "The diversity and evolutionary relationships of the pregnancy-associated glycoproteins, an aspartic proteinase subfamily consisting of many trophoblast-expressed genes," *Proc. Natl. Acad. Sci., USA*, 94:12809-12816, 1997.

Xie et al., The gene encoding bovine pregnancy-associated glycoprotein-1, an inactive member of the aspartic proteinase family,: *Gene*, 159:193-197, 1995.

Xie et al., "Trophoblast-specific processing ans phosphorylation of pregnancy-associated glycoprotein-1 in day 15 to 25 sheep placenta," *Biol. Reprod.*, 54:122-129, 1996.

Zoli et al., "Light and electron microscopic immunolocalization of bovine pregnancy-associated glycoprotein in the bovine placentome," *Biol. Reprod.*, 46:623-629, 1992.

Zoli et al., "Purification and characterization of a bovine pregnancy-associated glycoprotein," *Biol. Reprod.*, 45:1-10, 1991.

Zoli et al., "Radioimmunoassay of a bovine pregnancy-associated glycoprotein in serum: its application for pregnancy diagnosis," *Biol. Reprod.*, 46:83-92, 1992.

Decision on Appeal for Appeal 2007-4137 regarding U.S. Appl. No. 10/655,547, Nov. 8, 2007.

Ayad et al., "Correlation of five radioimmunoassay systems for measurement of bovine plasma pregnancy-associated glycoprotein concentrations at early pregnancy period," *Res. Vet. Sci.*, doi:10.1016/j.rvsc.2008.10.003, 2008.

U.S. Board of Appeal and Interference Decision on Appeal regarding U.S. Appl. No. 10/187,744, dated Sep. 17, 2007.

\* cited by examiner

COMPOSITIONS AND METHOD FOR ACCURATE EARLY PREGNANCY DIAGNOSIS

This application is a national stage application under 35 U.S.C. §371 of International Application No. PCT/US02/37236 filed Nov. 20, 2002, which claims benefit of priority from U.S. Provisional Ser. No. 60/331,822, filed Nov. 20, 2001, the entire contents of which are hereby incorporated by reference.

BACKGROUND OF THE INVENTION

I. Field of the Invention

The present invention relates generally to the fields of veterinary medicine, reproductive biology and diagnostics. More specifically, the present invention relates to improved methods for early stage pregnancy detection.

II. Related Art

Pregnancy diagnosis is an important component in sound reproductive management, particularly in the dairy industry (Oltenacu et al., 1990), where a high proportion of artificial inseminations fail (Streenan and Diskin, 1986). A reliable yet simple pregnancy test for cattle has long been sought. Several procedures are available, including a milk progesterone assay (Oltenacu et al., 1990; Markusfeld et al., 1990), estrone sulfate analysis (Holdsworth et al., 1982; Warnick et al., 1995), rectal palpation (Hatzidakis et al., 1993), ultrasound (Beal et al., 1992; Cameron and Malmo, 1993), and blood tests for pregnancy-specific antigens. Of these, the progesterone milk assay is the most cost effective for the producer (Oltenacu et al., 1990; Markusfeld et al., 1990). Next best is rectal palpation, performed at day 50 post-insemination (Oltenacu et al., 1990).

Even though the prior procedures for pregnancy diagnosis are potentially useful, all have fallen short of expectations in terms of their practical, on-farm use. For example, measurements of milk or serum progesterone around day 18-22 yield unacceptably high rates of false positives (Oltenacu et al., 1990; Markusfeld et al., 1990). The presence of estrone sulfate in urine or serum provides another test, but is only useful after day 100 as concentrations rise (Holdsworth et al., 1982; Warnick et al., 1995).

The discovery of pregnancy-specific protein B (PSP-B) (Butler et al., 1982) provided a new approach to pregnancy diagnosis since it could be detected in the blood of pregnant cows by the fourth week of pregnancy (Sasser et al., 1986; Humblot et al., 1988). Two other groups have developed immunoassays that may be based on an identical or immunologically similar antigen (Zoli et al., 1992a; Mialon et al., 1993; Mialon et al., 1994). In one case, the antigen (Mr~67 kDa) was called bovine pregnancy-associated glycoprotein (boPAG; now boPAG-1) (Zoli et al., 1992a); in the second, it was designated as pregnancy serum protein 60 (PSP60) (Mialon et al., 1993; Mialon et al., 1994). The immunoassay for PSP-B/boPAG1/PSP60 has two advantages. First, it can detect pregnancy relatively early. Second, interpretation of the assays does not require knowledge of the exact date of service, since boPAG-1 immunoreactive molecules are always present in the maternal serum of pregnant cows by day 28, and concentrations increase as pregnancy advances (Sasser et al., 1986; Mialon et al., 1993; Mialon et al., 1994).

There remain, however, two major disadvantages to this procedure. First, positive diagnosis in the fourth week of pregnancy remains somewhat uncertain because antigen concentrations in blood are low and somewhat variable. Second, boPAG1 concentrations rise markedly at term (Sasser et al., 1986; Zoli et al., 1992a; Mialon et al., 1993) and, due to the long circulating half-life of the molecule (Kiracofe et al., 1993), the antigen can still be detected 80-100 day postpartum (Zoli et al., 1992a; Mialon et al., 1993; Mialon et al., 1994; Kiracofe et al., 1993), compromising pregnancy diagnosis in cows bred within the early postpartum period. Thus, the test can be carried out in dairy cows at day 30 only if artificial insemination ("AI") is performed at 45-70 days postpartum.

Analysis of other BoPAGs in particular has exhibited potential for use in pregnancy testing. However, such tests can yield high false positive rates. This error rate occurs because the PAG test is done at day 25 of pregnancy. However, some embryos die between day 20 and 30 of pregnancy. This dying tissue can probably produce some PAG. Thus, the cow is PAG positive, but the embryo is dead. The results of this can be a false positive rate of 8%, which is generally considered to be unacceptable within commercial breeding programs. There is, therefore, a need for pregnancy tests with improved accuracy.

A pregnancy test that could be carried out reliably and early in pregnancy could provide definitive indication as to whether rebreeding or culling is required. In general, AI is successful less than 50% of the time and the producer must either rely on overt signs of return to estrus (that are easily missed) or delay rebreeding until pregnancy failure is confirmed by one of the methods described above. Such delays are extremely costly and constitute a major economic loss to the industry. There is thus a need for a feasible, sensitive and accurate pregnancy test in cattle that yields a low level of false positive results.

SUMMARY OF THE INVENTION

The invention provides methods for the early detection of pregnancy in livestock such as ungulates (e.g., hoofed animals). In one aspect of the invention, methods are provided for the early detection of pregnancy in a bovine animal comprising: (a) obtaining a sample from the bovine animal; (b) measuring the level of at least one bovine pregnancy associated antigen (BoPAG) in the sample; and (c) measuring the level of progesterone in the sample, wherein elevated levels of BoPAG and progesterone indicate that the bovine animal is pregnant. The sample may be from any biological material, including saliva, serum, blood, milk or urine. In certain embodiments of the invention, the sample may be obtained from the animal at days 16 to 30, days 16 to 28, days 16 to 25 and days 20 to 25 post-insemination, including about day 20, 25, 28 or 30 post-insemination. The analysis may comprise measuring the level of more that one BoPAG and, in certain embodiments, may comprise measuring one or more BoPAGs selected from the group consisting of BoPAG1, BoPAG2, BoPAG3, BoPAG4, BoPAG5, BoPAG6, BoPAG7, BoPAG8, BoPAG9, BoPAG7v; BoPAG9v; BoPAG10, BoPAG11, BoPAG12, BoPAG13, BoPAG14, BoPAG15; BoPAG16; BoPAG17; BoPAG18; BoPAG19; BoPAG20 or BoPAG21, including any combinations thereof The BoPAG may also be present in early pregnancy and may, for example, be selected from the group consisting of BoPAG2, BoPAG4, BoPAG5, BoPAG6, BoPAG7, BoPAG8, BoPAG9, BoPAG10, BoPAG11 and BoPAG21. Alternatively, the BoPAG may be present throughout pregnancy, and may also, for example, be selected from the group consisting of BoPAG2, BoPAG8, BoPAG10 and BoPAG11.

In one embodiment of the invention, a BoPAG that is analyzed is present in early pregnancy and absent at about two months post-partum. The BoPAG may, for example, be selected from the group consisting of BoPAG2, BoPAG4, BoPAG5, BoPAG6, BoPAG7, and BoPAG9. The measuring may comprise immunologic detection, including detecting a plurality of BoPAGs with polyclonal antisera. The polyclonal antisera may lack substantial binding activity to BoPAG1. In another embodiment of the invention, the polyclonal antisera is prepared against acidic fraction of day 75-85 BoPAG or comprises detecting a single BoPAG with a monoclonal antibody preparation. The immunologic detection may also comprise detection of multiple BoPAGs with a monoclonal antibody preparation. Immunologic detection may be carried out using any technique, including ELISA, RIA, and Western blot. The ELISA may comprise a sandwich ELISA comprising binding of a BoPAG to a first antibody preparation fixed to a substrate and a second antibody preparation labeled with an enzyme. In one embodiment, the enzyme is alkaline phosphatase or horseradish peroxidase. In certain embodiments of the invention, an elevated level of total BoPAG that is detected is from about 5 to about 10 ng/ml of serum, including about 5 ng/ml and 10 ng/ml. Measuring BoPAG levels may comprise, for example, nucleic acid hybridization, including Northern blotting and nucleic acid hybridization comprises amplification. The amplification may comprise RT-PCR.

In the method, measuring progesterone levels may also comprise immunologic detection. In certain embodiments of the invention, immunologic detection may comprise detecting progesterone with polyclonal antisera or detecting progesterone with a monoclonal antibody preparation. Immunologic detection may be carried out using any technique, including ELISA, RIA, and Western blot. The ELISA may comprise a sandwich ELISA comprising binding of a progesterone to a first antibody preparation fixed to a substrate and a second antibody preparation labeled with an enzyme. In one embodiment, the enzyme is alkaline phosphatase or horseradish peroxidase. The elevated level of progesterone that is detected may, in certain embodiments of the invention, comprise about 2 ng/ml of serum.

In certain embodiments of the invention, a sample is obtained at about day 25 post-insemination, and the elevated levels of BoPAG and progesterone are about 10 ng/ml and 2 ng/ml, respectively. A positive control sample may also be obtained from a pregnant bovine animal, as may a negative control sample from a non-pregnant bovine animal. The method may further comprise measuring BoPAG and progesterone levels from a second sample from the bovine animal at a second point in time.

In another aspect, the invention provides a method of making a breeding decision for a bovine animal comprising: (a) obtaining a sample from the bovine animal, wherein the bovine animal is suspected of being pregnant; (b) measuring the level of at least one bovine pregnancy associated antigen (BoPAG) in the sample; and (c) measuring the level of progesterone in the sample, wherein: (i) elevated levels of BoPAG and progesterone indicate that the bovine animal is pregnant, and no further steps need be taken; (ii) non-elevated levels of BoPAG and progesterone indicate that the bovine animal is not pregnant, and should be injected with gonadotropin-releasing hormone (GnRH), and about seven days later, injected with prostaglandin $F_{2\alpha}$ (PGF), followed by re-insemination; (iii) elevated levels of BoPAG and non-elevated levels of progesterone indicate that the bovine animal is not pregnant due to early embryo death and should be injected with GnRH, and about seven days later, injected with PGF, followed by re-insemination; or (iv) non-elevated levels of BoPAG and elevated levels of progesterone indicate that the bovine animal is not pregnant, and should be injected with PGF, followed by re-insemination. The method may also further comprise steps (ii), (iii) and (iv), about 48 hours after PGF injection and before re-insemination, administering a second injection of GnRH. The method may also further comprise, prior to step (a), inseminating the bovine animal.

DETAILED DESCRIPTION OF ILLUSTRATIVE EMBODIMENTS

The invention overcomes the limitations of the prior art by providing a reliable test for early pregnancy diagnosis and methods for use thereof. A reliable yet simple pregnancy test for cattle has long been sought. Typical prior test have either not allowed early detection of pregnancy or have suffered from a high incidence of false positive or false negative results. The prior tests, although potentially useful, have thus fallen short of expectations in terms of their practical, on-farm use.

The present invention overcomes the limitations of the prior art by analyzing placentally expressed polypeptides, designated pregnancy associated glycoproteins (PAGs), in conjunction with progesterone levels for the early and accurate diagnoses of bovine and other pregnancies. In particular, the inventors have found that by assaying for both progesterone and PAGs, early pregnancy diagnosis is possible with a high degree of accuracy. This is because the combined test measures a fetal component (PAG) and a maternal component (progesterone), both of which are essential for the establishment of successful pregnancy in cattle and other livestock species. The finding is significant because pregnancy diagnosis is an important component in reproductive management of livestock, particularly in the dairy industry where a high proportion of artificial inseminations fail and additional days open reduce the net operating income to the producer.

The tests of the invention can be carried out by detection of PAG and progesterone in the serum of animals, including bovines, in early pregnancy. In one embodiment of the invention, the assay can be carried out using polyclonal antibodies raised against early PAG enriched fraction. For example, such a fraction was purified by the inventors from day 80 bovine placenta. Alternatively, individual PAGs or combinations of PAGs can be analyzed as is described herein below. Methods for carrying out analysis of PAGs are disclosed in U.S. patent application Ser. No. 09/273,164, filed Mar. 19, 1999, the entire disclosure of which is specifically incorporated herein by reference. For progesterone analysis, commercially available assay kits are available that may be used to measure serum levels of progesterone. Using a PAG assay and the commercial progesterone assay, it was found that pregnancy detection could be performed as early as day 25 and with very low (<5%) false positive and false negative results.

I. Livestock Breeding Programs

One advance of the current invention is that it allows early detection of pregnancy with a low incidence of false positive results. Early detection of pregnancy is important because it allows rebreeding of animals found to not be pregnant. A low incidence of false positives is necessary to allow implementation of an effective rebreeding protocol. Prior pregnancy tests typically either were unable to be used for early testing or exhibited high incidence of false positives.

A type of early pregnancy test which has been used is the detection of pregnancy associated antigens (PAGs). An advantage of this test is that it can be done at day 25 of pregnancy. However, some embryos die between day 20 and 30 of pregnancy and, in some cases, the dying tissue may produce PAG. Thus cows may be PAG positive but the embryo is dead.

As discussed herein below, the inventors have found that by analyzing progesterone levels in addition to PAGs, a very low incidence (<5%) of false positives can be obtained. This is because the corpus luteum regresses shortly after embryo death. Thus, a cow with a dying embryo would have PAG but low progesterone. Because the progesterone is an absolute requirement for establishing pregnancy, a cow with low serum progesterone cannot maintain pregnancy.

A. Estrus and Ovulation

Dairy cows come into estrus once every 21 days. Cows display characteristic behaviors during estrus. Farmers can identify cows in estrus by these characteristic behaviors. Cows ovulate an egg about 28 hours after the onset of estrus. Most dairy cows are inseminated artificially about 12 hours after the onset of estrus so that sperm are in the reproductive tract when the cow ovulates.

B. Efficiency of Reproduction in Dairy Cows

Lactating dairy cows are watched for estrus. They are inseminated when they come into estrus so that they can become pregnant and have another calf. The efficiency with which cows are detected in estrus is low. Only about 50% of cows in estrus are actually detected by farmers. Of the cows detected in estrus and inseminated, only about 30% will become pregnant. Thus, only about 15% (50%×30%) of ovulations result in a pregnancy. Dairy reproduction is inefficient because cows in estrus are not always seen and those inseminated don't always get pregnant. Although most cows could be inseminated once every 21 days (assuming they do not get pregnant), the true insemination interval on farms is once every 40 to 60 days. The lost time results in frustration because farmers want their cows pregnant as soon as possible. There are also economic implications to the delay. The efficiency of reproduction has worsened since 1985 because of consolidation of the dairy industry (larger farms, less human-cow contact, labor shortages, etc.). Dairymen are very concerned about reproduction. Most dairy cows are culled because they do not get pregnant.

C. Corpus Luteum and Progesterone After a cow ovulates a corpus luteum (CL) is formed on the ovary that secretes a hormone called progesterone. Progesterone can be detected in the blood of the mother. Progesterone is needed to maintain the pregnancy. If the egg is fertilized and the embryo grows and survives then the corpus luteum will be maintained until the end of gestation (280 days). If the egg is not fertilized or the embryo dies then the corpus luteum will regress. The cow comes back into estrus after the corpus luteum regresses and can be inseminated again if seen in estrus.

D. PAG and Pregnancy Testing

The developing embryo produces PAGs. These can be detected in the blood of the mother at about 25 days of pregnancy. The PAG pregnancy test is designed to detect PAGs in the blood of the mother. A pregnant cow will also have high progesterone in blood because she will have a corpus luteum. Thus, pregnant cows will have PAG and progesterone in blood.

E. Pregnancy Testing in Dairy

The problem with reproductive management in dairy cattle is that pregnancy detection has previously typically been done 35 to 60 days after breeding. Furthermore, most nonpregnant cows are simply injected with PGF because the status of the corpus luteum is not known. However, the pregnancy tests of the current invention can be done 10 to 35 days sooner than these traditional pregnancy testing and only cows with a CL can be injected with PGF. Cows that do not have a CL (and will not respond to PGF) can be injected with GnRH and then treated with PGF at the appropriate time. By implementing this plan, farmers will know which cows are pregnant and also inseminate nonpregnant cows within about 30 days of their first insemination. The 25-day interval from breeding to pregnancy detection is shorter than current methods and the 30-day interval from first breeding to second breeding for nonpregnant cows is much shorter than the industry average.

Pregnancy testing in dairy cows has usually been done by manually feeling for an embryo in the uterus. The manual test is typically done 35 to 60 days after breeding. On large dairies, a single veterinarian may be employed 100% time to do manual pregnancy testing. The only alternative to manual testing is ultrasound testing. This can be done at 28 days after breeding. Ultrasound testing is not routine because the equipment is expensive and the test takes longer than the manual test.

F. Drugs Used to Manipulate Reproductive Cycles in Dairy

Dairy cows can be injected with prostaglandin $F_{2\alpha}$ (PGF) to regress the corpus luteum and cause estrus. PGF only works if the cow has a corpus luteum. Cows that do not have a corpus luteum will not respond to PGF. Dairy cows without a corpus luteum can be injected with gonadotropin-releasing hormone (GnRH) to cause ovulation and the formation of a corpus luteum. One typical way to manage dairy cows without a corpus luteum is to inject GnRH, wait 7 days (allows CL to form), inject PGF and await the cow's next estrus. Both PGF and GnRH are inexpensive and are commonly used in dairy herds (either alone or in combination). Another approach is to inject GnRH, wait seven days and inject PGF, and then wait two days and inject GnRH. This protocol (Ovsynch protocol) is popular because cows can be inseminated after the second GNRH without the need for estrus detection.

G. Implementation of Improved Pregnancy Tests in Breeding Programs

Using the new assays, there are four possible outcomes with respect to the PAG and progesterone results: +/+, +/−, −/+ and −/−. Based on the results, various steps will be desired for implementation of breeding programs. The different possibilities and the likely desired course of action are set forth below in Table 1.

TABLE 1

Reproductive plan implemented 25 days after breeding

| PAG Test Result | Progesterone Test Result | Pregnancy outcome | Farmer action |
| --- | --- | --- | --- |
| Positive | Positive | Cow is pregnant | No action needed. Farmer is happy. |
| Positive | Negative | The embryo underwent early embryonic death and the cow is not pregnant. | Cow does not have a CL (based on low progesterone). Inject GnRH (cause ovulation), wait seven days, inject PGF (regress CL). The farmer can breed at estrus or an alternative would be to give another injection of GnRH at 48 hours after PGF to induce ovulation and breed. These are common reproductive management treatments in dairy. |
| Negative | Positive | Cow is not pregnant | Cow has a CL but does not have an embryo. Inject PGF to regress the CL. The farmer can breed at estrus or an alternative would be give another injection of GnRH at 48 hours after PGF to induce ovulation and breed. These are common reproductive management treatments in dairy |

TABLE 1-continued

Reproductive plan implemented 25 days after breeding

| PAG Test Result | Progesterone Test Result | Pregnancy outcome | Farmer action |
|---|---|---|---|
| Negative | Negative | Cow is not pregnant | Cow does not have a CL and does not have an embryo. Inject GnRH, wait seven days, inject PGF. The farmer can breed at estrus or an alternative would be give another injection of GnRH at 48 hours after PGF to induce ovulation and breed. These are common reproductive management treatments in dairy. |

II. Pregnancy Associated Glycoproteins

The placenta is the hallmark of the eutherian mammal. Rather than being the most anatomically conserved mammalian organ, however, it arguably is the most diverse (Haig, 1993). Placentation ranges from the invasive hemochorial type, as in the human, where the trophoblast surface is in direct contact with maternal blood, to the epitheliochorial (e.g., pig), where the uterine epithelium is not eroded (Amoroso, 1952). Not only is placental structure highly variable, the polypeptide hormones the placenta produces also vary between species (Haig, 1993; Roberts et al., 1996). For example, no group of mammals other than higher primates possesses a chorionic gonadotrophin homologous to hCG for luteal support in early pregnancy, and only the ruminant ungulates are known to produce Type I interferon as an antilyteolytic hormone (Roberts et al., 1996).

Placentation in ruminants, such as cattle and sheep, is superficial, relatively noninvasive, and known as synepitheliochorial cotyledonary (Wooding, 1992). 'Synepitheliochorial' describes the fetal-maternal syncytium formed by the fusion of trophoblast binucleate cells and uterine epithelial cells, whereas, 'cotyledonary' describes the gross structure of the placenta and specifically the tufts of villous trophoblast (cotyledons) that insinuate themselves into the crypts of the maternal caruncles. These regions of interdigitated and partially fused fetal cotyledonary and maternal caruncles are the placentomes and are the main sites for nutrient and gas exchange in the placenta. The binucleate cells, which compose about 20% of the surface epithelium (trophectoderm) migrate and fuse with maternal uterine epithelial cells and deliver their secretory products directly to the maternal system. Among the products are the placental lactogens (Wooding, 1981) and the pregnancy-associated glycoproteins (Zoli et al., 1992a.)

Bovine pregnancy-associated glycoproteins (boPAGs), also known under a variety of other names including pregnancy-specific protein-B (Butler et al., 1982), were discovered in attempts to develop pregnancy tests for livestock (Sasser et al., 1986; Zoli et al., 1991; Zoli et al., 1992a). Rabbits were injected with extracts of placental cotyledons, and antibodies not directed against placental antigens were removed by adsorption with tissue extracts from nonpregnant animals. The resulting antisera provided the basis of an accurate pregnancy test for cattle and sheep as early as one month post-insemination.

Xie et al. (1991) used an antiserum directed against purified boPAGs from cattle and from sheep to screen cDNA libraries from late placental tissue. The fill-length cDNAs shared 86% nucleotide sequence identities with each other and a surprising 60% sequence identity to pepsinogens. The boPAGs had mutations in and around their active sites that would render them inactive as proteinases (Xie et al., 1991; Guruprasad et al., 1996). The similarities to pepsin A (~50% amino acid identity) and chymosin (~45%) in primary structure has allowed atomic models of ovine (ov)PAG1 and boPAG1 to be built (Guruprasad et al., 1996). Both molecules have the bilobed structure typical of all known eukaryotic aspartic proteinases and possess a cleft between the two lobes capable of accommodating peptides up to 7 amino acids long. Modeling strongly suggested that both ovPAG1 and boPAG1 can bind the pepsin inhibitor pepstatin, a prediction that has been validated.

Even in initial studies (Butler et al., 1982; Zoli et al., 1991; Xie et al., 1991; Xie et al., 1994; Xie et al., 1996), it was clear that the boPAGs were heterogenous in molecular weight and charge, and as more isoforms have been purified it has become evident that they differ in their amino terminal sequences (Atkinson et al., 1993; Xie et al., 1997a). Further library screening has revealed additional transcripts in ruminants (Xie et al., 1994; Xie et al., 1995; Xie et al., 1997b) and the existence of PAGs in non-ruminant species such as the pig (Szafranska et al., 1995), and the horse (Guruprasad et al., 1996).

Despite their apparent lack of proteolytic activity, all of the PAGs whose amino terminal sequences have been determined are proteolytically processed in a manner typical of other aspartic proteases such as pepsin (Davies, 1990). For example, a pro-peptide of most PAGs, which constitutes the first 38 amino acids of the secreted form and which normally folds into the active site region, has been cleaved from the secreted forms of PAG. Thus, the calculated molecular weight of the mature, non-glycosylated PAG, i.e. with signal sequence propeptide removed would be ~36,000 daltons and the circulating antigen in serum would also lack this segment. The observed molecular weight of secreted PAG, however, is much larger ranging from 45,000 daltons to 90,000 daltons (Xie et al., 1991; Sasser et al., 1989; Xie et al., 1996), probably due to extensive glycosylation (Holdsworth et al., 1982). Multiple boPAG genes in the bovine genome have most likely contributed to the triphasic alterations of PAG concentrations in maternal serum.

A. BoPAG1

Bovine (bo) PAG1 was initially identified as a unique placental antigen by raising antisera to total bovine placental extracts (Zoli et al., 1991). It is a product of binucleate trophoblast cells (Xie et al., 1991; Zoli et al., 1992b) which constitute the invasive component of the placenta (Wooding, 1992; Guillomot, 1995). In 1991, cDNA for both boPAG1 and ovine PAG1 was identified (ovPAG1) (Xie et al., 1991). Surprisingly, the PAG1 belong to the aspartic proteinase (AP) gene family, a grouping that includes pepsin, chymosin, renin, and cathepsin D and E (Guruprasad et al., 1996). Unlike other members of the AP family, both ovPAG1 and boPAG1 appear to be enzymatically inactive, since the catalytic domain in the active site region is mutated (Xie et al., 1991; Guruprasad et al., 1996).

BoPAG1 gene contains 9 exons and 8 introns (Xie et al., 1996), an identical organization to that of other mammalian aspartic genes. Southern genomic blotting with a probe encompassing exon 7 and exon 8, which represent the most conserved region of PAG relative to other AP, indicated that there were probably many PAG genes. In addition, when a bovine genomic library was probed with boPAG1 cDNA, 0.06% positive phage plaques were identified, suggesting that there may be 100 or more PAG genes in the bovine genome (Xie et al., 1995). This approximation has recently been confirmed by a variety of other approaches (Xie et al., 1997b).

Levels of boPAG1 or related molecules that cross-react with a boPAG-1 antiserum are very low around day 21 to day 27 (Warnick et al., 1995; Beal et al., 1992; Cameron and Malmo, 1993; Butler et al., 1982), are maintained at a higher, but still low concentration until about day 100 of the pregnancy and then rise quickly to ~100 ng/ml. The concentrations then remain relatively constant until the last quarter of pregnancy when they peak at 1 µg/ml of serum or greater right before parturition. One explanation for the triphasic profile of boPAG1 immunoreactivity is that expression of boPAG1 is very low in early pregnancy, rises considerably at mid gestation and peaks before parturition (Sasser et al., 1986; Zoli et al., 1992a; Patel et al., 1995). Alternatively, the presence of immunoreactive antigen in very early pregnancy may be due to the production of other boPAGs. The rise in the second trimester may reflect production of yet a different class of boPAG or possibly the initiation of low PAG1 expression. The exponential rise of boPAGs just prior to parturition could represent a sudden increase in the synthesis of one or more boPAG1 related molecules or increased "escape" across a leakier utero-placental junction.

Immunocytochemistry and in situ hybridization analyses have shown that boPAG1 and ovPAG1, and their close relatives (since neither the antisera nor the probes are expected to be monospecific) are localized to binucleate cells (Xie et al., 1991; Zoli et al., 1992b) In contrast, the antigenically distinct boPAG2 is expressed in predominantly mononucleate cells of the trophectoderm (Xie et al., 1994). In the ruminants, binucleate cells are the invasive components of the trophoblast and do not appear until about day 13 in sheep and day 17 in cattle (Wooding, 1992). They then quickly increase in number. By day 21 in cattle they constitute up to 20% of cells in the trophectoderm, and a high percentage are actively fusing with maternal uterine epithelial cells (Wooding, 1992; King et al., 1980; Guillomot, 1995). Binucleate cell granules, which contain PAG1 (Zoli et al., 1992b), are discharged from the fusion cell towards the maternal stroma and its network of capillaries. Therefore, the binucleate cell products have ready access to the maternal circulation.

B. Novel OvPAG and BoPAG Species cDNA for a series of novel boPAGs have been identified and cloned. A similar large family of ovine (ov) PAGs have been identified from sheep placenta (Xie et al., 1991; Xie et al., 1997a; Xie et al., 1997b). Certain of the boPAGs are useful in detection of early pregnancy in cattle. These molecules are homologous to, but different from, boPAG1 (Xie et al., 1991). Apparently, PAGs constitute a polymorphic group (Xie et al., 1994; Xie et al., 1995; Xie et al., 1997a; Xie et al., 1997b), whose members either show variable degrees of immunocrossreactivity or do not cross-react at all with the antisera that have been developed. Some of the cloned PAGs are only expressed in binucleate cells of the placental. These cells are known to have an endocrine function (Wooding, 1992). They produce placental lactogen and steroids, for example. However, the functions of the PAG family members are unknown, although they enter the maternal circulation.

One important aspect of the present invention is that PAGs are not expressed uniformly throughout pregnancy. Some are found early in pregnancy, while are others are expressed in later stages. For example, PAGs that are expressed most strongly in the invasive binucleate cells at implantation are not dominant in late pregnancy. Conversely, boPAG1 (PSP-B) (Xie et al., 1991; Butler et al., 1982; Sasser et al., 1986) primarily is a product of binucleate cells of the late placenta, and antiserum raised against it fails to recognize the dominant PAG produced by binucleate cells in early pregnancy. Therefore, the test developed by the other groups and based on boPAG1/PSP-B/PSP60 (Butler et al., 1982; Sasser et al., 1986; Zoli et al., 1992a; Mialon et al., 1993; Kiracofe et al., 1994 ) is only marginally useful early in pregnancy because the antigen is produced in extremely small amounts, if at all, at that time. The expression pattern of boPAG1 also helps explain the concentration profile of the antigen measured in serum. At term, levels can exceed 5 µg/ml, while at day 40, when the development of the placenta in terms of size is almost complete, concentrations are around 10 ng/ml, i.e., 500-fold lower.

Certain of the novel boPAGs disclosed in this invention (boPAG 4, 5, 6, 7, and 9), having the sequences of SEQ ID NO:27, SEQ ID NO:28, SEQ ID NO:29, SEQ ID NO:30, and SEQ ID NO:32 are present at day 25 of pregnancy. These PAGs are expressed in invasive binucleate cells which release their secretory granules into maternal uterine capillary bed. Of these five, boPAG4 appears to cross react with the late pregnancy PAG, boPAG1, which has been the basis of the earlier pregnancy test. By virtue of their early expression, these PAGs can be detected by conventional immunological techniques in physiological fluids of heifers or cows (especially in serum, urine, and milk) to detect the presence of a fetus or fetuses in the uterus prior to day 30 of pregnancy. Thus, the presence of these antigens provide a diagnostic test of early pregnancy in cattle.

Similar observations on the diversity of PAGs, the localization of different PAGs to either mononucleated and binucleated cells, and the likely varied timing of PAG expression have been noted in sheep (Xie et al., 1991; Xie et al., 1997a; Xie et al., 1997b). Because of the large number of genes noted in other species, these observations are likely also to hold for other Artiodactyla, as well.

C. Purification of the Proteins

It will be desirable to purify the various PAGs. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number" (i.e., 2-fold, 5-fold, 10-fold, 50-fold, 100-fold, 1000-fold, etc.). The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat or acid pH denaturation of contaminating proteins, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE and according to how extensively it is glycosylated (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of min, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat gern; D-galactosamine has been used in obtaining lectins from clams and L-fucose will bind to lectins from lotus. PAG antigens can be purified by using a pepstatin agarose affinity matrix, e.g., as described by Avalle et al. (2001)

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

D. Antigen Compositions

The present invention provides for the use of PAGs or peptides as antigens for the generation of polyclonal antisera and monoclonal antibodies for use in the detection of pregnancy. It is envisioned that some variant of a PAG, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers such as keyhole limpet hemocyannin (KLH) or glutathione-S-transferase.

In order to formulate PAGs for immunization, one will generally desire to employ appropriate salts and buffers to render the polypeptides stable. Aqueous compositions of the present invention comprise an effective amount of the PAG antigen to the host animal, dissolved or dispersed in a pharmaceutically acceptable carrier or aqueous medium. Such compositions may be referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The PAGs also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It should be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the PAGs in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, preparations should meet applicable sterility, pyrogenicity, general safety and purity standards.

III. Generating Antibodies Reactive with PAGs and Progesterone

In another aspect, the present invention contemplates an antibody that is immunoreactive with a PAG molecule or progesterone of the present invention, or any portion thereof. An antibody can be a polyclonal or a monoclonal antibody composition, both of which are preferred embodiments of the present invention. Means for preparing and characterizing antibodies are well known in the art (see, e.g., Harlow and Lane, 1988).

Briefly, a polyclonal antibody is prepared by immunizing an animal with an immunogen comprising a peptide or polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention.

Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to PAG-related antigen epitopes. Additionally, it is proposed that monoclonal antibodies specific to the particular PAG of different species may be utilized in other useful applications.

In general, both polyclonal and monoclonal antibodies against PAG or progesterone may be used in a variety of embodiments. For example, they may be employed in antibody cloning. protocols to obtain cDNAs or genes encoding antibodies to PAG(s) and progesterone. They may also be used in inhibition studies to analyze the effects of PAG or progesterone related peptides in cells or animals. Anti-PAG or antibodies to progesterone pathway enzymes will also be useful in immunolocalization studies to analyze the distribution of PAGs or enzymes that participate in progesterone biosynthesis or metabolism during various cellular events, for example, to determine the cellular or tissue-specific distribution of PAGs or progesterone biosynthesis or metabolism under different points in the cell cycle. A particularly useful application of such antibodies is in purifying native or recombinant PAG, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed Mycobacterium tuberculosis), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g. a purified or partially purified PAG or progesterone. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

IV. Assays for PAG and Progesterone Expression for the Detection of Pregnancy

According to the present invention, the present inventors have determined that PAGs in combination with progesterone can be used advantageously expressed in early stages of pregnancy and, therefore, can be used as markers in the detection of pregnancy at an early stage. In cattle, the BoPAGs may be used individually or in combination to provide a diagnostic evaluation of pregnancy. According to the present invention, these boPAGs include BoPAGs1 through 21. Other boPAGs, and PAGs from other species, may prove useful, alone or in combination, for similar purposes.

A. Immunologic Detection of BoPAGs and Progesterone

The present invention entails the use of antibodies in the immunologic detection of PAGs or progesterone. Various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs) and radioimmunoassays (RIA). Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes. Preferred samples, according to the present invention, are fluids, such as milk, urine, blood, serum or saliva.

Contacting the chosen biological sample with the protein, peptide or antibody under conditions effective and for a period of time sufficient to allow the formation of immune complexes (primary immune complexes) is generally a matter of simply adding the composition. to the sample and incubating the mixture for a period of time long enough for the antibodies to form immune complexes with PAGs or progesterone. After this time, the PAG- or progesterone antibody mixture will be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Usually, the primary immune complexes may be detected by means of a second binding ligand that has binding affinity for the PAG- or progesterone-specific first antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the PAG or progesterone antibody is used to form secondary immune complexes, as described above. The second binding ligand contains an enzyme capable of processing a substrate to a detectable product and, hence, amplifying signal over time. After washing, the secondary immune complexes are contacted with substrate, permitting detection.

Progesterone can also be detected in accordance with the invention using various commercially available detection kits. For example, the Coat-a-Count™ progesterone kit used by the inventors, which is available from Diagnostics Products Corporation (Los Angeles, Calif.). Examples of other assays that have been described include the immunoenzymatic technique described, for example, by Stefanakis et al., (1994) and by Stanley et al. (1986); and salivary progesterone level assays described, for example, by Lu et al., (1997) and Vienravi et al., 1994.

B. ELISA

As a part of the practice of the present invention, the principles of an enzyme-linked immunoassay (ELISA) may be used. ELISA was first introduced by Engvall and Perlmann (1971) and has become a powerful analytical tool using a variety of protocols (Engvall, 1980; Engvall, 1976; Engvall, 1977; Gripenberg et al., 1978; Sarngadharan et al., 1984). ELISA allows for substances to be passively adsorbed to solid supports such as plastic to enable facile handling under laboratory conditions. For a comprehensive treatise on ELISA the skilled artisan is referred to "ELISA; Theory and Practise" (Crowther, 1995 incorporated herein by reference).

The sensitivity of ELISA methods is dependent on the turnover of the enzyme used and the ease of detection of the product of the enzyme reaction. Enhancement of the sensitivity of these assay systems can be achieved by the use of fluorescent and radioactive substrates for the enzymes. Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

In a preferred embodiment, the invention comprises a "sandwich" ELISA, where anti-PAG antibodies are immobilized onto a selected surface, such as a well in a polystyrene microtiter plate or a dipstick. Then, a test composition suspected of containing PAGs, e.g., a clinical sample, is contacted with the surface. After binding and washing to remove non-specifically bound immunocomplexes, the bound antigen may be detected by a second antibody to the PAG.

In another exemplary ELISA, polypeptides from the sample are immobilized onto a surface and then contacted with the anti-PAG antibodies. After binding and washing to remove non-specifically bound immune complexes, the bound antibody is detected. Where the initial antibodies are linked to a detectable label, the primary immune complexes may be detected directly. Alternatively, the immune complexes may be detected using a second antibody that has binding affinity for the first antibody, with the second antibody being linked to a detectable label.

Another ELISA in which the PAGs are immobilized involves the use of antibody competition in the detection. In this ELISA, labeled antibodies are added to the wells, allowed to bind to the PAG, and detected by means of their label. The amount of PAG in a sample is determined by mixing the sample with the labeled antibodies before or during incubation with coated wells. The presence of PAG in the sample acts to reduce the amount of antibody available for binding to the well, and thus reduces the ultimate signal.

Irrespective of the format employed, ELISAs have certain features in common, such as coating, incubating or binding, washing to remove non-specifically bound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human cancer and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG), evaporated or powdered milk, and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 h to 2 h to 4 h, at temperatures preferably on the order of 25° C. to 27° C., or may be overnight at about 4° C. or so.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immunecomplex formation (e.g. incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

A variant of ELISA is the enzyme-linked coagulation assay, or ELCA (U.S. Pat. No. 4,668,621), which uses the coagulation cascade combined with the labeling enzyme RVV-XA as a universal detection system. The advantage of this system for the current invention, is that the coagulation reactions can be performed at physiological pH in the presence of a wide variety of buffers. It is therefore possible to retain the integrity of complex analytes.

C. Nucleic Acid Detection

In a variety of embodiments, it will be desirable to detect nucleic acids (mRNAs or cDNAs) for BoPAGs and/or progesterone and determine the levels of the corresponding proteins. Such methods include Northern assays and RT-PCR. The following describe methods relevant to the detection and quantification of such nucleic acids.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more. complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific MRNA transcripts. It is generally appreciated that conditions can be rendered more stringent by the addition of increasing amounts of formamide.

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 MM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843, 663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to BoPAGs1-21 or progesterone are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemilluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al, 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which maybe used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands, under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Kits

All the essential materials and/or reagents required for detecting BoPAGS1-21 or progesterone in a sample may be assembled together in a kit. This generally will comprise a probe or primers designed to hybridize specifically to individual nucleic acids of interest in the practice of the present invention. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Study #1: Design and Results

Due to high levels of false positive results obtained using a PAG assay only, a new assay format analyzing both progesterone and PAG levels was designed. A series of designated PAG and progesterone cutoff levels for pregnancy determination based on given concentrations of PAGs and progesterone were formulated for analysis as set forth below:

| | |
|---|---|
| Day 16 | 5 ng/ml PAG + 3 ng Progesterone/ml |
| Day 16 | 10 ng/ml PAG + 3 ng Progesterone/ml |
| Day 20 | 5 ng/ml PAG + 3 ng Progesterone/ml |
| Day 20 | 10 ng/ml PAG + 3 ng Progesterone/ml |
| Day 25 | 10 ng/ml PAG + 2 ng Progesterone/ml |
| Day 28 | 10 ng/ml PAG + 2 ng Progesterone/ml |
| Day 30 | 10 ng/ml PAG + 2 ng Progesterone/ml |

Assays were carried out as described below. The results of the assays are set forth below in Table 2. As can be seen, the new assay formats had a markedly higher accuracy or pregnancy detection at day 25 relative to progesterone or PAG analysis alone.

Example 2

Study #1: Assay Format and Integration of Progesterone Assay

Serum levels of progesterone were obtained using the Coat-a-Count™ progesterone kit (Diagnostics Products Corporation, Los Angeles, Calif.). The results of PAG and progesterone serum measurements were compared with cow pregnancy history beyond day 45 (i.e. pregnancy information around day 100) to assess pregnancy diagnosis. As indicated above, serum PAG and progesterone assay results and pregnancy data collected for 74 cows were used for assessing pregnancy diagnosis.

The results are summarized in Table 2. The cutoff range used for PAG was 10 ng/ml. This range was selected based on following criteria: a) the pregnancy history of the cow and b) the trend of PAG levels in the serum. If a cow is pregnant, the PAG levels tend to increase from day 16 to day 45. A lower cutoff range of 5 ng/ml was also used for day 16 and day 20 because this is very early stage of PAG secretion by the conceptus.

Two cutoff ranges (3 ng/ml and 2 ng/ml) for progesterone were used for Progesterone. The cutoff ranges were selected based on: a) pregnancy history of the cows, b) Progesterone levels during estrus cycle and pregnancy in cows. For analysis of false positive results, the cow was not pregnant while the test was positive for PAG or Progesterone or PAG+Prog with levels above the indicated cutoff range. For false negatives, the cow was pregnant while the test is negative for PAG or Progesterone or PAG+Progesterone with levels below the indicated cutoff range.

The results were analyzed for PAG only, Progesterone only and the combination of PAG and Progesterone and compared to pregnancy history. As shown in Table 3, testing at day 25 for either PAG or Progesterone only has low false negative

TABLE 2

Results of Bovine Pregnancy Test Evaluation Study #1

| Day of Pregnancy Testing | Cut off Range for PAG | Cut off Range for Progesterone | No. of Cows Pregnant | No. of Cows Open | No. of cows false positive (%) | N. of cows false negative (%) |
|---|---|---|---|---|---|---|
| Pregnancy Record | — | — | 54 | 20 | — | — |
| Day 45 Palpation | — | — | 53 | 19 | 1 (1.4%) | 1 (1.4%) |
| PAG Assay Only | | | | | | |
| Day 20 | 10 ng/ml | — | 30 | 44 | 7 (9.5%) | 31 (41.9%) |
| Day 25 | 10 ng/ml | — | 58 | 16 | 6 (8.1%) | 2 (2.7%) |
| Day 30 | 10 ng/ml | — | 58 | 16 | 5 (6.8%) | 1 (1.4%) |
| Progesterone Only | | | | | | |
| Day 20 | — | 3 ng/ml | 56 | 18 | 5 (6.8%) | 3 (4%) |
| Day 25 | — | 2 ng/ml | 59 | 15 | 5 (6.8%) | 0 (0%) |
| Day 30 | — | 2 ng/ml | 61 | 13 | 9 (12.2%) | 2 (2.7%) |
| PAG & Progesterone | | | | | | |
| Day 16 | 5 ng/ml | 3 ng/ml | 40 | 34 | 6 (8.1%) | 20 (27%) |
| Day 20 | 5 ng/ml | 3 ng/ml | 42 | 32 | 4 (5.4%) | 16 (21.6%) |
| Day 20 | 10 ng/ml | 3 ng/ml | 27 | 47 | 3 (4.0%) | 30 (41%) |
| Day 20 | 10 ng/ml | 2 ng/ml | 28 | 46 | 3 (4.0%) | 29 (39%) |
| Day 25 | 10 ng/ml | 3 ng/ml | 51 | 23 | 2 (2.7%) | 4 (5.4%) |
| Day 25 | 10 ng/ml | 2 ng/ml | 54 | 20 | 2 (2.7%) | 2 (2.7%) |
| Day 30 | 10 ng/ml | 3 ng/ml | 52 | 22 | 2 (2.7%) | 5 (6.8%) |
| Day 30 | 10 ng/ml | 2 ng/ml | 53 | 21 | 2 (2.7%) | 3 (4%) | results (range from 0% to 2.7%). However, the false positive results (range from 6.8% to 8.1%). The combination of PAG and progesterone lowers the false positive results to below 3% showing an increased accuracy of pregnancy diagnosis by combining these two measurements. Further, use of the 2 ng cutoff for progesterone rather than 3 ng results in substantially decreased false negatives on days 25 through 30.

These results establish that a combination of PAG and progesterone measurements can be used for detecting pregnancy from day 25 and beyond in cows with low false positive and false negative results. The low false-positive and false-negative results of the combined assay for day 25 and beyond also offer a feasibility of developing a reliable pregnancy test for cattle.

In addition, the PAG assay used did not detect any PAG in the serum of postpartum cows beyond day 45 after calving (data not shown). This is an added advantage over the existing PAG1 assay (developed by Sasser et al) since PAG1 remains detectable in day 100 postpartum cows.

The results of the study showed that a combination of PAG and Progesterone measurements allows accurate early detecting of pregnancy in cattle with very low false positive and false negative results. The assay results showed that the pregnancy status could be detected successfully by day 25 and beyond in cattle.

Example 3

Sample Collection Study

A sample collection study was performed for evaluating the accuracy of pregnancy diagnosis using the PAG assay. The study design was to collect serum, milk and urine samples at days 0, 16, 20, 25 and 30 following artificial insemination of 120 cows. The herd veterinarian palpated the cows at day 45 for pregnancy confirmation. All breeding records and pregnancy data for the cows were also obtained. Data collected from several cows were removed from the study due to re-breeding, pregnancy loss and other problems and not included in the analysis. PAG assay results for the 74 cows with complete records of breeding and pregnancy status were used evaluating pregnancy test. The serum samples from these 74 cows were used for assaying PAG and progesterone concentration.

Example 4

Polyclonal PAG Assay Development

The following section describes the polyclonal antibody based assay development for PAGs. The assay was standardized with an early PAG enriched fraction as antigen and affinity purified rabbit polyclonal antibodies. This assay was used to determine the feasibility of detecting PAG during early pregnancy.

Antigen proteins were isolated using day 75-85 placenta. PAGs were fractionated based on their partitioning into acidic, neutral and basic isoelectric pH after binding to pepstatin affinity chromatography. The PAG eluted from the column at neutral pH were defined as neutral PAG (M3) and the PAG isolated from the column at acidic pH as acidic PAG (M4). Acidic PAG (M4) fraction was used as antigen in the assay.

Antibodies were generated in rabbits according to the standard protocol-using day 75-85 acidic and neutral PAG. Two rabbits were immunized with acidic PAG and two were immunized with neutral PAG in Freunds complete adjuvant. After a two-week interval these rabbits were boosted with corresponding antigen with incomplete adjuvant. The rabbits were boosted every two weeks until sufficient antisera were collected and stored at −70° C. Polyclonal antibodies were affinity purified using protein A chromatography and dialyzed in PBS. Purified antibodies were aliquoted and stored at −70° C.

Example 5

Assay Procedure

Two sandwich type immunoassays were developed to evaluate the early pregnancy by using acidic (M4) and neutral (M3) PAG specific polyclonal antibodies. Immobilized M4 antibodies were reacted with serum samples and a biotin labeled M4 antibodies were added as secondary antibody. Captured biotin label antibodies were reacted with streptavidin-HRP to generate a color reaction. Neutral PAG (M3) specific antibodies were not stable in solution and precipitated upon storage. This assay was discontinued after assay reproducibility failed due to the precipitation problem. The current working assay is the M4 antigen assay, which correspond to early PAG. The calibration range for this assay was from 2 to 64 ng/ml. This assay was optimized to obtain the best sensitivity and low cross reactivity to the non-pregnant serum samples.

Example 6

Study #2: Resynchronization of Dairy Cows and Heifers after PAG/Progesterone Pregnancy Diagnosis The inventors designed a second study to test efficacy of a method for rebreeding cows and heifers that are diagnosed as not pregnant after a PAG/progesterone test. Generally, cattle are tested for PAG/progesterone 28 to 30 days after breeding and are diagnosed pregnant or non-pregnant. The resynchronization method is implemented on non-pregnant cows 0 to 2 days after the PAG/progesterone test. Animals are treated in the following sequence: (i) inject prostaglandin $F_{2\alpha}$ ($PGF_{2\alpha}$; a hormone causing regression of the corpus luteum); (ii) wait two days, inject gonadotropin releasing hormone (GnRH; a hormone causing ovulation); (iii) wait 0 to 8 hours, (iv) inseminate artificially.

Methods. Dairy cows and heifers were tested for PAG 28 to 30 days after first AI. Cattle diagnosed not pregnant were treated with 5 mL Lutalyse (25 mg $PGF_{2\alpha}$), two days later were treated with 2 mL Cystorelin (100 μg GnRH), and were inseminated 0 to 8 hours after GnRH. The resynchronization treatment was administered 0 to 2 days after the PAG test (30 days after first insemination). Pregnancy was determined 30 to 60 days after insemination.

Results. Table 3 shows the conception rate for cows and heifers. Data are separated according to concentrations of progesterone. Two ng/mL is the cut-off for PAG/Progesterone testing. A cow or heifer with greater than 2 ng/mL progesterone would be predicted to have a corpus luteum that will respond to $PGF_{2\alpha}$ (more-likely to become pregnant after resynchronization). A cow or heifer with progesterone less than 2 ng/mL would be predicted to have a corpus luteum that may not respond to $PGF_{2\alpha}$ (less-likely to become pregnant after resynchronization).

TABLE 3

Conception Rate

| Location | Type | P4 < 2 ng/mL | P4 ≧ 2 ng/mL | Total |
|---|---|---|---|---|
| Foremost (UMC) | Cow | 2/15 (13) | 9/20 (45) | 11/35 (31) |
| Foremost (UMC) | Heifer | 3/3 (100) | 2/4 (50) | 5/7 (71) |
| Private dairy | Cow | 1/3 (33) | 4/12 (33) | 5/15 (33) |
| ALL Locations | | 6/21 (29) | 15/36 (42) | 21/57 (37) |

Conception rate is defined as "no. pregnant/no. inseminated (%)" for cows and heifers that were PAG negative (nonpregnant) with progesterone (P4) either less than or greater than 2 ng/mL.

Discussion. The resynchronization method yielded conception rates that were similar to first insemination. Thus, the method appears to be a sound approach for handling cows that are not pregnant after first insemination.

Example 7

Study #3: Measurement of PAG and Progesterone Levels for Accurate Pregnancy Diagnosis in Cattle In study #1, the inventors presented data from 79 cows showing that a combination of PAG values above or equal to 10 ng/ml, and progesterone values above or equal to 2 ng/ml, would predict pregnancy status of cows with 97% sensitivity and 97% specificity from 25 days following AI. In this follow-up study, the inventors used 270 cows to evaluate combined testing for PAG and progesterone for pregnancy diagnosis, as compared to ultrasound and palpation results at day 30 and 45 post AI.

Study description and design. The objective of the study was to evaluate the accuracy, sensitivity (ability to detect pregnant cows) and specificity (ability to detect open cows) of PAG and progesterone assays in determining pregnancy status in dairy cows. The study was conducted in 3 commercial dairies. About 300 cows were available at the start of the study. The study began on day 0 (day of insemination). Blood samples were collected daily from day 20 to 30 days post-insemination and again on day 45 (palpation day). Pregnancy status of the cows was determined on days 25-29 by transrectal ultrasonography. A second pregnancy exam by rectal palpation was performed at day 45. A small number of cows were removed from the study due to health problems. Samples from 270 cows were available at the end of the study. Serum PAG levels were determined by PAG ELISA with M4 antiserum. The progesterone levels were measured by using a commercially available radioimmunoassay kit.

Results. The results of the analysis are shown in Tables 4 and 5. As in study #1, the inventors used several cut-off ranges to assess pregnancy status and, instead of presenting the data as percentages of false-positives and false-negatives diagnosed, the percentages of sensitivity and specificity of pregnancy diagnosis are presented.

Table 4 shows the results for PAG, progesterone, PAG and progesterone tests with observed sensitivity and specificity compared to pregnancy status of the cows determined by ultrasonography and palpation. These data show that combined PAG and P4 test increased the specificity (ability to identify open cows or reducing the false-positives) by more than 20% in every cut-off ranges examined. In addition, these data also support the claim that PAG and progesterone combined test will increase the accuracy of pregnancy detection.

In Table 5, the highlighted cut-off values give a minimum of 94% sensitivity and 90% specificity. Again, as in study #1, the inventors used several cut-off ranges to assess pregnancy status and the percentages of sensitivity and specificity of pregnancy diagnosis are presented. The present data shows that it would able to identify 96% of pregnant cows (i.e., 4% false-negatives) and 91.2% of open cows (8.8% false-positives) on day 25 with 10 ng/ml PAG and 2 ng/ml P4 cut-off range. The data also shows that increasing the PAG cut-off range. up to 26 ng/ml and P4 cut-off at 2 ng/ml consistently improved the specificity of the test (reducing the false-positive diagnosis).

The variability in the PAG cut-off ranges may be due to different set of reagents (assay standard, dilution serum used for standard) used for PAG ELISA. In spite of using the same batch of PAG antibody and PAG antibody conjugate reagents, a change in the standard curve linearity was noted in this study. This would have influenced the absolute values of PAG measured in the serum samples. The progesterone radioimmunoassay used in the study was an identical commercial kit used in study #1 and no shift in the standard curve linearity was noted in this assay.

TABLE 4

On days 25, 27, 29 and 45, a cut-off value for PAG and progesterone were individually selected. The values chosen forced sensitivity as close to 98% as possible and then the corresponding specificity was determined. The selected cut-offs for the individual days were then combined (right-hand side) to determine how the test might be improved using the two analytes. Note however, the values change each test day.

| | | Individual Tests | | | Combined PAG + Prog | | |
|---|---|---|---|---|---|---|---|
| Sample Day | Model | Cut-off (ng/ml) | Sensitivity (%) | Specificity (%) | Cut-off (ng/ml) | Sensitivity (%) | Specificity (%) |
| 25 | PAG | 6.7 | 98.0 | 76.0 | | | |
| (n = 270) | Prog | 3.8 | 95.0 | 72.5 | 6.7-3.8 | 92.9 | 91.8 |
| | | 3.4 | 98.0 | 70.0 | 6.7-3.4 | 96.0 | 91.8 |
| | | 3.0 | 100.0 | 66.7 | 6.7-3.0 | 97.0 | 90.6 |
| | | 2.0 | 100.0 | 59.9 | 6.7-2.0 | 98.0 | 89.5 |
| | | 1.0 | 100.0 | 49.9 | 6.7-1.0 | 98.0 | 88.3 |
| 27 | PAG | 15.0 | 98.0 | 82.4 | | | |
| (n = 263) | Prog | 3.9 | 95.0 | 71.7 | 15.0-3.9 | 92.9 | 93.3 |
| | | 3.5 | 98.0 | 68.1 | 15.0-3.5 | 94.9 | 92.1 |
| | | 2.7 | 100.0 | 61.4 | 15.0-2.7 | 98.0 | 91.5 |
| | | 2.0 | 100.0 | 54.2 | 15.0-2.0 | 98.0 | 90.3 |
| | | 1.0 | 100.0 | 38.0 | 15.0-1.0 | 98.0 | 87.3 |

TABLE 4-continued

On days 25, 27, 29 and 45, a cut-off value for PAG and progesterone were individually selected. The values chosen forced sensitivity as close to 98% as possible and then the corresponding specificity was determined. The selected cut-offs for the individual days were then combined (right-hand side) to determine how the test might be improved using the two analytes. Note however, the values change each test day.

| | | Individual Tests | | | Combined PAG + Prog | | |
|---|---|---|---|---|---|---|---|
| Sample Day | Model | Cut-off (ng/ml) | Sensitivity (%) | Specificity (%) | Cut-off (ng/ml) | Sensitivity (%) | Specificity (%) |
| 29 (n = 261) | PAG | 28.4 | 98.0 | 91.4 | | | |
| | Prog | 3.8 | 95.0 | 64.3 | 28.4-3.8 | 92.9 | 94.5 |
| | | 3.5 | 98.0 | 60.7 | 28.4-3.5 | 94.9 | 94.5 |
| | | 3.1 | 100.0 | 52.7 | 28.4-3.1 | 98.0 | 94.5 |
| | | 2.0 | 100.0 | 40.5 | 28.4-2.0 | 98.0 | 93.2 |
| | | 1.0 | 100.0 | 30.1 | 28.4-1.0 | 98.0 | 93.2 |
| 45 (n = 267) | PAG | 9.9 | 97.9 | 88.8 | | | |
| | Prog | 4.5 | 95.0 | 70.2 | 9.9-4.5 | 93.8 | 98.2 |
| | | 4.3 | 98.0 | 69.3 | 9.9-4.3 | 96.9 | 98.2 |
| | | 3.5 | 100.0 | 57.0 | 9.9-3.5 | 97.9 | 96.5 |
| | | 2.0 | 100.0 | 43.3 | 9.9-2.0 | 97.9 | 94.7 |
| | | 1.0 | 100.0 | 34.2 | 9.9-1.0 | 97.9 | 93.5 |

TABLE 5

A set cut-off value for PAG was evaluated over days 25 to 29 to determine how flexible the test might be. The selected PAG value was then combined with various cut-off for progesterone to determine if test specificity could be adequately improved. Note, the values are constant across all test days. (Highlighted cut-offs give a minimum of 94% Sensitivity and 90% specificity on at least days 27, 28 and 29 post AI.)

| PAGs (ng/ml) | Prog. (ng/ml) | Sensitivity | | | Specificity | | |
|---|---|---|---|---|---|---|---|
| | | Day 25 | Day 27 | Day 29 | Day 25 | Day 27 | Day 29 |
| 10 | 0.0 | 96.0 | 100.0 | 100.0 | 78.9 | 76.4 | 80.4 |
| 10 | 1.0 | 96.0 | 100.0 | 100.0 | 90.1 | 83.6 | 85.3 |
| 10 | 2.0 | 96.0 | 100.0 | 100.0 | 91.2 | 86.7 | 85.9 |
| 10 | 3.0 | 94.9 | 99.0 | 100.0 | 92.4 | 87.9 | 89.0 |
| 10 | 4.0 | 88.9 | 93.9 | 94.9 | 94.2 | 90.3 | 91.4 |
| 12 | 0.0 | 92.9 | 99.0 | 100.0 | 80.1 | 78.2 | 81.6 |
| 12 | 1.0 | 92.9 | 99.0 | 100.0 | 90.1 | 84.8 | 85.9 |
| 12 | 2.0 | 92.9 | 99.0 | 100.0 | 91.2 | 87.9 | 86.5 |
| 12 | 3.0 | 91.9 | 98.0 | 100.0 | 92.4 | 89.1 | 89.6 |
| 12 | 4.0 | 85.9 | 92.9 | 94.9 | 94.2 | 91.5 | 91.4 |
| 14 | 0.0 | 89.9 | 99.0 | 99.0 | 82.5 | 81.2 | 84.7 |
| 14 | 1.0 | 89.9 | 99.0 | 99.0 | 91.2 | 86.7 | 87.7 |
| 14 | 2.0 | 89.9 | 99.0 | 99.0 | 91.8 | 89.7 | 87.7 |
| 14 | 3.0 | 88.9 | 98.0 | 99.0 | 93.0 | 90.9 | 90.8 |
| 14 | 4.0 | 82.8 | 92.9 | 93.9 | 94.7 | 93.3 | 92.6 |
| 16 | 0.0 | 85.9 | 98.0 | 99.0 | 85.4 | 84.2 | 85.3 |
| 16 | 1.0 | 85.9 | 98.0 | 99.0 | 91.8 | 88.5 | 87.7 |
| 16 | 2.0 | 85.9 | 98.0 | 99.0 | 92.4 | 90.9 | 87.7 |
| 16 | 3.0 | 84.8 | 96.9 | 99.0 | 93.6 | 92.1 | 90.8 |
| 16 | 4.0 | 78.8 | 91.8 | 93.9 | 95.3 | 93.9 | 92.6 |
| 18 | 0.0 | 80.8 | 98.0 | 99.0 | 86.5 | 85.5 | 85.9 |
| 18 | 1.0 | 80.8 | 98.0 | 99.0 | 93.0 | 89.1 | 88.3 |
| 18 | 2.0 | 80.8 | 98.0 | 99.0 | 93.6 | 91.5 | 88.3 |
| 18 | 3.0 | 79.8 | 96.9 | 99.0 | 94.2 | 92.7 | 91.4 |
| 18 | 4.0 | 73.7 | 91.8 | 93.9 | 95.9 | 94.5 | 93.3 |
| 20 | 0.0 | 77.8 | 98.0 | 99.0 | 88.3 | 86.7 | 89.0 |
| 20 | 1.0 | 77.8 | 98.0 | 99.0 | 94.2 | 90.3 | 91.4 |
| 20 | 2.0 | 77.8 | 98.0 | 99.0 | 94.2 | 92.1 | 91.4 |
| 20 | 3.0 | 76.8 | 96.9 | 99.0 | 94.2 | 92.7 | 93.3 |
| 20 | 4.0 | 71.7 | 91.8 | 93.9 | 95.9 | 94.5 | 93.3 |
| 22 | 0.0 | 76.8 | 98.0 | 99.0 | 88.9 | 86.7 | 89.6 |
| 22 | 1.0 | 76.8 | 98.0 | 99.0 | 94.7 | 90.9 | 92.0 |
| 22 | 2.0 | 76.8 | 98.0 | 99.0 | 94.7 | 92.1 | 92.0 |
| 22 | 3.0 | 75.8 | 96.9 | 99.0 | 94.7 | 92.7 | 93.3 |
| 22 | 4.0 | 70.7 | 91.8 | 93.9 | 95.9 | 94.5 | 93.9 |
| 24 | 0.0 | 74.7 | 98.0 | 99.0 | 90.6 | 87.3 | 89.6 |
| 24 | 1.0 | 74.7 | 98.0 | 99.0 | 95.3 | 90.3 | 92.0 |
| 24 | 2.0 | 74.7 | 98.0 | 99.0 | 95.3 | 92.7 | 92.0 |
| 24 | 3.0 | 73.7 | 96.9 | 99.0 | 95.3 | 93.3 | 93.3 |
| 24 | 4.0 | 68.7 | 91.8 | 93.9 | 95.9 | 94.5 | 93.9 |
| 26 | 0.0 | 72.7 | 95.9 | 99.0 | 91.8 | 88.5 | 90.8 |
| 26 | 1.0 | 72.7 | 95.9 | 99.0 | 95.9 | 92.1 | 93.3 |
| 26 | 2.0 | 72.7 | 95.9 | 99.0 | 95.9 | 93.3 | 93.3 |
| 26 | 3.0 | 71.7 | 94.9 | 99.0 | 95.9 | 93.9 | 94.5 |
| 26 | 4.0 | 66.7 | 89.8 | 93.9 | 95.9 | 95.2 | 94.5 |

In summary, the results of study #3 support the utility of the claimed invention. Combined testing of PAG and progesterone considerably reduces the false-positive and false-negative results and improves the accuracy of pregnancy diagnosis in cows.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,367,110
U.S. Pat. No. 4,452,901
U.S. Pat. No. 4,668,621
U.S. Pat. No. 4,683,195
U.S. Pat. No. 4,683,202
U.S. Pat. No. 4,800,159
U.S. Pat. No. 4,883,750
U.S. Pat. No. 5,279,721
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. application Ser. No. 09/273,164

Amoroso, *In: Marshall's Physiology of Reproduction*, Parkes (Ed.), Little Brown and Co., Boston, 2:127-311, 952, 1952.
Atkinson et al., *J. Biol. Chem.*, 268(35):26679-26685, 1993.
Beal et al., *J. Anim. Sci.*, 70:924-929, 1992.
Bellus, *J. Macromol Sci. Pure Appl. Chem.*, A31(1): 1355-1376, 1994.
Butler et al., *Biol. Reprod.*, 26:925-933, 1982.
Cameron and Malmo, *Austr. Vet. J.*, 70:109-111, 1993.
Campbell et al., *J. Mol. Biol.*, 180:1-19, 1984.
Capaldi et al., *Biochem. Biophys. Res. Comm.*, 76:425, 1977.
Crowther, *In: Methods in Molecule Biology*, Vol. 42, Humana Press; New Jersey, 1995.
Davies, *Ann. Rev. Bioiphys. Chem.*, 19:189-215, 1990.
Engvall and Perlmann, *Immunochem.*, 8:871-873, 1971.
Engvall, *Lancet*, 2(8000):1410, 1976.
Engvall, *Med Biol.*, 55(4):193-200, 1977.
Engvall, *Methods Enzymol*, 70(A):419-39, 1980.
European App. 329 822
European App. 320 308
Frohman, *In: PCR Protocols: A Guide To Methods And Applications*, Academic Press, N.Y., 1990.
GB App. 2 202 328
Gefter et al., *Somatic Cell Genet.*, 3:231-236, 1977.
Goding, *In: Monoclonal Antibodies: Principles and Practice*, 2d ed., Academic Press, Orlando, Fla., pp 60-61, 71-74, 1986.
Gripenberg et al., *Scand J Immunol.*, 7(2):151-7, 1978.
Guillomot, *J. Reprod. Fertil.*, 49(Suppl):39-51, 1995.
Guruprasad et al., *Protein Engin.*, 9:949-856, 1996.
Haig, *Rev. Biol.*, 68:495-532, 1993.
Harlow and Lane, *In: Antibodies, a Laboratory Manual*, Cold Spring Harbor Laboratory, pp 139-281, 1988.
Hatzidakis et al., *J. Reprod. Fertil.*, 98:235-240, 1993.
Holdsworth et al., *J. Endocrin.*, 95:7-12, 1982.
Humblot et al., *Theriogenol.*, 30:257-268, 1988.
King et al., *J. Reprod. Fertil.*, 59:95-100, 1980.
Kiracofe et al., *J. Anim. Sci.*, 71:2199-2205, 1993.
Kohler and Milstein, *Eur. J. Immunol*, 6:511-519, 1976.
Kohler and Milstein, *Nature*, 256:495-497, 1975.
Kwoh et al., *Proc. Nat. Acad. Sci. USA*, 86: 1173, 1989.
Markusfeld et al., *Br. Vet. J.*, 146: 504-508, 1990.
Mialon et al., *Reprod. Nutr. Dev.*, 33:269-282, 1993.
Mialon et al., *Reprod. Nutr. Dev.*, 34:65-72, 1994.
Nakamura et al., *In: Handbook of Experimental Immunology* (4$^{th}$ Ed.), Weir et al. (Eds.), Blackwell Scientific Publ., Oxford, 1:27, 1987.
Ohara et al., *Proc. Natl. Acad. Sci.* USA, 86:5673-5677, 1989.
Oltenacu et al., *J. Dairy Sci.*, 73:2826-2831, 1990.
Patel et al., *Theriogenol.*, 44:827-833, 1995.
PCT App. PCT/US87/00880
PCT App. PCT/US89/01025
PCT App. PCT/US90/07641

PCT App. WO 88/10315
PCT App. WO 89/06700
*Remington's Pharmaceutical Sciences,* 15th ed., pp 1035-1038 and 1570-1580.
Rippe et al., *Mol. Cell Biol.,* 10:689-695, 1990.
Roberts et al., *Biol. Reprod.,* 54:294-302, 1996.
Roberts et al., *Prog. Nucl. Acid Res. Mol. Biol.,* 56:287-326, 1996.
Sambrook et al., *In: Cold Spring Harbor Laboratory Press,* 2nd Ed., 1989.
Sarngadharan et al., *Princess Takamatsu Symp.,* 15:301-8, 1984.
Sasser et al., *Biol. Reprod.* 35:936-942, 1986.
Sasser et al., *J. Reprod. Fertil.,* 37(Suppl):109-113, 1989.
Stanley et al., *Veterinarian Record,* 664-667, 1986.
Stefanakis et al., *Bull. Hellenic Vet. Med. Soc.,* 45:37-43, 1994.
Streenan and Diskin, *In: Embryonic Mortality in Farm Animals,* Sreenan and Diskin (Eds.), Martinus Nijhoff Publishers, 1-11, 1986.
Szafranska et al., *Biol. Reprod.,* 53:21-28, 1995.
Tur-Kaspa et al., *Mol. Cell Biol.,* 6:716-718, 1986.
Vienravi et al., *J. Med. Assoc. Thai.,* 77(3):138-47, 1994.
Walker et al., *Proc. Natl. Acad. Sci. USA,* 89:392-396 1992.
Warnick et al., *Theriogenol.,* 44:811-825, 1995.
Wooding et al., *Placenta,* 13:101-113, 1992.
Wooding, *J. Reprod. Fertil.,* 62:15-19, 1981.
Xie et al., *Biol. Reprod.,* 51:1145-1153, 1994.
Xie et al., *Biol. Reprod.,* 54: 122-129, 1996.
Xie et al., *Biol. Reprod.,* 57:1384-1393, 1997a.
Xie et al., *Gene,* 159:193-197, 1995.
Xie et al., *Proc. Natl. Acad. Sci. USA,* 94:12809-12816, 1997b.
Xie et al., *Proc. Natl. Acad. Sci. USA,* 88:10247-10251, 1991.
Zoli et al., *Biol. Reprod.,* 45:1-10, 1991.
Zoli et al., *Biol. Reprod.,* 46:623-629, 1992b.
Zoli et al., *Biol. Reprod.,* 46:83-92, 1992a.

The invention claimed is:

1. A method for the early detection of pregnancy in a bovine animal comprising:
   (a) obtaining a sample from said bovine animal;
   (b) measuring the level of at least one bovine pregnancy associated glycoprotein (BoPAG) in said sample; and
   (c) measuring the level of progesterone in said sample,
wherein the sample is obtained at days 16 to 30 post-insemination and wherein elevated levels of BoPAG and progesterone relative to non-pregnant animals indicate that said bovine animal is pregnant and wherein said BoPAG is selected from the group consisting of BoPAG4, BoPAG5, BoPAG6, BoPAG7 or BoPAG9.

2. The method of claim 1, wherein said sample is saliva, serum, blood, milk or urine.

3. The method claim 2, wherein elevated level of total BoPAG is from about 5 to about 10 ng/ml of serum.

4. The method of claim 3, wherein elevated level of total BoPAG is about 5 ng/ml.

5. The method of claim 3, wherein elevated level of total BoPAG is about 10 ng/ml.

6. The method claim 2, wherein elevated level of progesterone is about 2 ng/ml of serum.

7. The method of claim 1, wherein said sample is obtained from said animal at day 20, 21, 22, 23, 24, 25, 26, 27 or 28 post-insemination.

8. The method of claim 1, further comprising measuring the level of more that one BoPAG.

9. The method of claim 1, wherein said BoPAG is present in early pregnancy.

10. The method of claim 1, wherein said BoPAG is present throughout pregnancy.

11. The method of claim 1, wherein said BoPAG is present in early pregnancy and absent at about two months postpartum.

12. The method of claim 1, wherein said measuring BoPAG levels comprises immunologic detection.

13. The method of claim 12, wherein said immunologic detection comprises detecting a plurality of BoPAGs with polyclonal antisera.

14. The method of claim 13, wherein said polyclonal antisera lack substantial binding activity to BoPAG1.

15. The method of claim 13, wherein said polyclonal antisera is prepared against acidic fraction of day 60-85 BoPAG.

16. The method of claim 13, wherein said polyclonal antisera is prepared against neutral fraction of day 60-85 BoPAG.

17. The method of claim 12, wherein said immunologic detection comprises detecting a single BoPAG with a monoclonal antibody preparation.

18. The method of claim 12, wherein said immunologic detection comprises detection of multiple BoPAGs with a monoclonal antibody preparation.

19. The method of claim 12, wherein said immunologic detection comprises a method selected from the group consisting of ELISA, RIA and Western blot.

20. The method of claim 19, wherein said ELISA is a sandwich ELISA comprising binding of a BoPAG to a first antibody preparation fixed to a substrate and a second antibody preparation labeled with an enzyme.

21. The method of claim 20, wherein said enzyme is alkaline phosphatase or horseradish peroxidase.

22. The method of claim 1, wherein measuring BoPAG levels comprises nucleic acid hybridization.

23. The method of claim 22, wherein nucleic acid hybridization comprises a method selected from the group consisting of Northern blotting, amplification and RT-PCR.

24. The method of claim 1, wherein measuring progesterone levels comprises immunologic detection.

25. The method of claim 24, wherein said immunologic detection comprises detecting progesterone with polyclonal antisera.

26. The method of claim 24, wherein said immunologic detection comprises detecting progesterone with a monoclonal antibody preparation.

27. The method of claim 24, wherein said immunologic detection comprises a method selected from the group consisting of ELISA, RIA and Western blot.

28. The method of claim 27, wherein said ELISA is a sandwich ELISA comprising binding of progesterone to a first antibody preparation fixed to a substrate and a second antibody preparation labeled with an enzyme.

29. The method of claim 28, wherein said enzyme is alkaline phosphatase or horseradish peroxidase.

30. The method of claim 1, wherein measuring progesterone levels comprises measuring progesterone biosynthesis pathway enzyme levels by nucleic acid hybridization, immunologic detection or enzyme activity measurement.

31. The method of claim 30, wherein nucleic acid hybridization comprises a method selected from the group consisting of Northern blotting, amplification and RT-PCR.

32. The method of claim 1, wherein said sample is obtained at day 25 post-insemination, and the elevated levels of BoPAG and progesterone are 10 ng/ml and 2 ng/ml, respectively.

33. The method of claim 1, further comprising a positive control sample from a pregnant bovine animal.

34. The method of claim 1, further comprising a negative control sample from a non-pregnant bovine animal.

35. The method of claim 1, further comprising measuring BoPAG and progesterone levels from a second sample from said bovine animal at a second point in time.

36. A method of making a breeding decision for a bovine animal comprising:
   (a) obtaining a sample from said bovine animal, wherein said bovine animal is suspected of being pregnant;
   (b) measuring the level of at least one bovine pregnancy associated antigen (BoPAG) in said sample; and
   (c) measuring the level of progesterone in said sample, wherein the sample is obtained at days 16 to 30 post-insemination and wherein:
      (i) elevated levels of BoPAG and progesterone indicate that said bovine animal is pregnant, and no further steps need be taken;

(ii) non-elevated levels of BoPAG and progesterone indicate that said bovine animal is not pregnant, and should be injected with gonadotropin-releasing hormone (GnRH), and about seven days later, injected with prostaglandin $F_{2\alpha}$ (PGF), followed by re-insemination;

(iii) elevated levels of BoPAG and non-elevated levels of progesterone indicate that said bovine animal is not pregnant due to early embryo death and should be injected with GnRH, and about seven days later, injected with PGF, followed by re-insemination; or (iv) non-elevated levels of BoPAG and elevated levels of progesterone indicate that said bovine animal is not pregnant, and should be injected with PGF, followed by re-insemination, wherein levels of BoPAG and progesterone are relative to non-pregnant animals and wherein said BoPAG is selected from the group consisting of BoPAG4, BoPAG5, BoPAG6, BoPAG7 or BoPAG9.

37. The method of claim 36, further comprising in steps (ii), (iii) and (iv), about 48 hours after PGF injection and before re-insemination, administering a second injection of GnRH.

38. The method of claim 36, further comprising, prior to step (a), inseminating said bovine animal.

39. The method of claim 36, wherein said PGF injection is administered at day 28 post-insemination and wherein said re-insemination is carried out at day 31 post-insemination.

* * * * *

UNITED STATES PATENT AND TRADEMARK OFFICE
CERTIFICATE OF CORRECTION

PATENT NO. : 7,575,861 B2  Page 1 of 1
APPLICATION NO. : 10/496164
DATED : August 18, 2009
INVENTOR(S) : Lucy et al.

It is certified that error appears in the above-identified patent and that said Letters Patent is hereby corrected as shown below:

Title page, item [54] and col. 1 in the title, delete "METHOD" and insert --METHODS--.

Title page, in Foreign Patent Documents delete "00/06038" and insert --99/06038--.

In claim 8, column 117, line 37, delete "that" and insert --than--.

Signed and Sealed this

Twenty-seventh Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,575,861 B2  
APPLICATION NO. : 10/496164  
DATED : August 18, 2009  
INVENTOR(S) : Lucy et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 365 days Delete the phrase "by 365 days" and insert -- by 925 days --

Signed and Sealed this

Thirteenth Day of April, 2010

David J. Kappos  
*Director of the United States Patent and Trademark Office*

UNITED STATES PATENT AND TRADEMARK OFFICE
CERTIFICATE OF CORRECTION

PATENT NO.      : 7,575,861 B2                              Page 1 of 1
APPLICATION NO. : 10/496164
DATED           : August 18, 2009
INVENTOR(S)     : Lucy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1485 days.

Signed and Sealed this

Seventh Day of September, 2010

David J. Kappos
*Director of the United States Patent and Trademark Office*

SEQUENCE LISTING

<160> NUMBER OF SEQ ID NOS: 56

<210> SEQ ID NO 1
<211> LENGTH: 1295
<212> TYPE: DNA
<213> ORGANISM: bovidae

<400> SEQUENCE: 1

```
cttggatcca ggaaataaac atgaagtggc ttgtgctcct cgggctggtg gccttctcag      60
agtgcatagt caaaatacct ctaaggagac tgaagaccat gagaaatgtc gtcagtggaa     120
aaaacatgct gaacaatttt ctgaaggagc atgcttacag tctgtcccag atttcttttc     180
gtggctcaaa tctaactact cacccgctga gaaacatcaa ggatttggtc tacatgggta     240
acatcaccat tggaacaccc cctcaggaat tccaggttgt ctttgacaca gcctcatctg     300
acttgtgggt gccctccgac ttttgcacta gtccagcctg ttctacacac gttaggttca     360
gacatcttca gtcttccact ttccggctta ccaataagac cttcaggatc acctatggat     420
ctgggagaat gaaaggagtt gttgttcatg acacagttcg gattgggaac cttgtaagta     480
ctgaccagcc atttggtcta agcattgagg aatacgggtt tgagggcaga atttatgatg     540
gtgtcttggg cttgaactac cccaacatat ccttctctgg agccatcccc atctttgaca     600
agctgaagaa tcaacgtgcc atttctgagc ctgttttttgc cttctacttg agcaaagatg     660
agcgggaggg cagtgtggtg atgtttggtg gggtggacca ccgctattat gagggagagc     720
tcaactgggt accectgate caagcaggcg actggagtgt acacatggac cgcatctcca     780
ttgaaagaaa gattattgct tgttctgatg gctgcaaggc ccttgtggac accgggacat     840
cagatatcgt aggtccaaga agactggtca ataacatcca taggctcatc ggtgccatac     900
cacggggttc cgagcactac gttccatgtt ctgaggtcaa tacctgccc tctattgtct     960 tcaccatcaa cggcatcaac tacccagtgc caggtcgagc ctacatcctc aaggatgata    1020
gaggccgctg ctataccacc tttcaagaga accgagtgag ttcatctaca gagacctggt    1080
acctgggtga cgtcttcctg agactgtatt tctcggtctt tgatcgagga aatgacagaa    1140
ttggcctggc acgggcagtg taaatgctta gagtggttca ggaatcagta aggccactcc    1200
```

```
taacacacac tcactcacac tttggcactc ctgcccagaa tgctggtgaa ctgtatttgg   1260
tggtcttcac actctattct tagtaaagaa taaag                              1295

<210> SEQ ID NO 2
<211> LENGTH: 1258
<212> TYPE: DNA
<213> ORGANISM: bovidae

<400> SEQUENCE: 2
gaaagaagca tgaagtggct tgtgctcctc gggctggtgg ccctctcaga gtgcatagtc     60
attttgcctc taaagaaaat gaagaccttg cgagaaaccc tgagggaaaa aaacttgctg    120
aacaatttcc tggaggaaca agcttacaga ctgtccaaga atgactccaa ataactatt    180 cacccgctga ggaactatct ggatactgcc tacgtgggta acatcaccat tggaacaccc    240
cctcaggagt tccgggtcgt cttttgacaca ggctcagcta acttgtgggt gccctgcatc    300
acctgtacca gtccagcctg ttatacacac aaaaccttca atcctcaaaa ttcttcaagc    360
ttccgggaag taggctcgcc tatcaccatc ttctatggat ctgggataat tcagggattt    420
cttggctctg acaccgttcg gatcgggaac cttgttagcc ctgaacagtc gtttggccta    480
agcctggagg aatacgggtt tgattctcta ccctttgatg gtatcctggg cttggctttt    540
cccgccatgg gcatcgaaga taccatcccc atctttgaca acttgtggtc acacggtgcc    600
ttttctgagc ctgtcttcgc cttctacttg aacacaaaca gccagaggg cagtgtggtg    660 atgtttggtg gggtggacca ccgctactac aaggagagc tcaactggat accagtgtcc    720
caaactagcc attggcagat aagcatgaac aacatcagca tgaatgggac tgtgactgct    780
tgttcttgtg gatgtgaggc ccttttggac accgggacta caatgatcta cggcccaaca    840
aaactggtca ccaacatcca aagctcatg aacgccaggc ttgagaattc tgagtatgtg    900
gtttcatgtg atgctgtcaa gaccctgcct cctgtcatct tcaacatcaa tggcatcgac    960
tatccactgc gccctcaagc ctacatcatc aagattcaaa acagctgccg cagcgtcttt   1020
caaggaggca cagaaaatag ctctctaaac acctggatcc ttggtgatat cttcctgagg   1080
cagtacttct cggttttga tcgtaaaaat agaaggattg gcctggctcc ggcagtgtaa   1140
atgcttggac tatcagcaag catttgacta aatcagtcag gctgctccta acacacactc   1200
gctcacacta ggcactcctg ccagcgatgc tggtgaattg tgtttggtgc tgcaaacc     1258

<210> SEQ ID NO 3
<211> LENGTH: 1266
<212> TYPE: DNA
<213> ORGANISM: bovidae

<400> SEQUENCE: 3
ggcttgtgct cctcgggctg gtggccttct cagagtgcat agtcaaaata cctctaagga     60
gagtgaagac catgagaaat accgtcagtg gaaaaaacat actgaacaat atcctgaagg    120 agcatgtttta cagactgtcc cagatttctt ttcgtggctc aaatctaact actcacccgc    180
tgagaaacat caaggatttg atatacgtgg gtaacatcac cattggaaca ccccctcagg    240
aattccaggt tgtctttgac acaggctcat ctgacttttg ggtgccctct gacttttgca    300
ctagtcgagc ctgttctaca cacgttaggt tcagacatct tcagtcttcc accttccggc    360
tcaccaataa gaccttcagg atcacctatg gatctgggag aatgaaagga gttgttgctc    420
atgacacagt tcggattggg gaccttgtaa gtactgacca accgtttggt ctaagtgtgg    480
aggaatatgg gtttgagggc agagcttatt atgatggtgt cttgggcttg aactaccccca    540
```

-continued

```
acatatcctt ctctggagcc atccccatct ttgacaacct gaagaatcaa ggtgccattt      600
ctgagcctgt ttttgccatt ctactgagca aagacgagca ggagggcagt gtggtgatgt      660
ttggtggggt ggaccaccgc tactataggg gagagctcaa ctgggtacca ttgattgaag      720
cgggtgactg gattatacac atggaccgca tctccatgaa aagaaagatt attgcttgtt      780
ctggcagctg cgaggccatt gttgacactg ggacatcagc aatagaaggc caagaaaac      840 tggtaaataa gatacacaag ctcatcggcg ccaggccacg gcattccaag tactacattt      900
catgttctgc ggtcaatacc ctgccttcta ttatcttcac catcaacggc atcaactacc      960
catgtccagg tcgagcctac gtgctcaagg attctagagg ccgctgctat tccatgtttc     1020
aagagaacaa agtgagttca tctacagaga cctggatcct gggcgatgtc tttctgaggg     1080
tgtatttctc agtctttgat cgaggaaatg acaggattgg cctggcacga gcagtgtaaa     1140
tgcttggagt ggttcaggaa tcagtaaggc cgctcctaac acacactcac tcacactagg     1200
cactcctgcc caggatggtg gtgaactgta tttggtggtc gtacaccct attctctcgt     1260 gccgtt                                                                1266

<210> SEQ ID NO 4
<211> LENGTH: 1359
<212> TYPE: DNA
<213> ORGANISM: bovidae

<400> SEQUENCE: 4
acaaaaaccc tcagtggaaa aaacatgctg aacaatttcg tgaaggagca tgcttacaga       60
ctgtcccaga tttcttttcg tggctcaaat ctaactattc acccgctgag aaacatcagg      120 gatttttct atgtgggtaa catcaccatt gggacacccc tcaggaatt ccaggttatc       180 tttgacacag gctcatctga gttgtgggtg ccctccatct tttgcaacag ctcaacctgt      240
tctaaacacg ataggttcag acatcttgag tcttctacct tccggcttag caggaggacc      300
ttcagcatca cctatggatc tgggagaatt gaagcacttg ttgttcatga cacagttcgg      360
attggggacc ttgtaagtac tgatcagcag ttcggtctat gcctagaaga atctgggttt      420
gagggcatga gatttgatgg cgtcttgggc ttgagctata ccaacatatc cccctctgga      480
gccatcccca tcttttacaa gctgaagaat gaaggtgcca tttctgaacc tgttttgcc      540 ttctacttga gcaaagatga gcgggagggc agtgtggtga tgtttggtgg ggcggaccac      600
cgctactaca agggagagct caactggata ccattgatga aagcaggcga ctggagtgta      660
cacatggacc gcatctccat gaaaagaaag gttattgctt gctctggcgg ctgcaaggcc      720
cttgtggaca cggggtcatc agatatcgta ggcccaagta cactggtcaa taacatctgg      780
aagctcatcg gtgccacgcc acagggttct gagcactacg tttcatgttc tgcggtcaat      840
agcctaccct ctattatctt caccatcaaa agcaacaact accgagtgcc aggtcaagcc      900
tacatcctca aggattctag aggccgctgc tttactgcct ttaaagggca tcaacagagt      960
tcatctacag agatgtggat cctgggtgac gtctttctga ggctgtattt ctcagtcttt     1020
gatcgaagaa aggacagaat tggcctgcc accaaggtgt gaatgcttgg agtggttcag     1080
gaatcagtaa ggccactcct aacacacact cactcacact ttgggcactc ctgcccaagg     1140
aatgctggtg aactgtaatt tggtggtctg tacaccctat tctctgggaa gaaggcaatg     1200 gcacccccact ccagtactct tgcctggaaa atcacatgga cagaagcctg gtgggctcca     1260
gtccatgggg tttctaagag tcgggcaata actgagcacc ttcacttata ctttcacttt     1320
acaccctatt ctcaataaaa gataaatggt ttcactcttt                            1359
```

<210> SEQ ID NO 5
<211> LENGTH: 1317
<212> TYPE: DNA
<213> ORGANISM: bovidae

<400> SEQUENCE: 5

| | | | | | |
|---|---|---|---|---|---|
| ccctgagtac | ttggagccag | gaaagaagta | tgaagtggct | tgtgctcctt | gggctgctga | 60 |
| cctcctcaga | gtgcatagtc | atcctacctc | taacaaaagt | gaagaccatg | agaaaaaccc | 120 |
| tcagtgaaaa | aaacatgctg | aacaatttcc | tgaaggaaca | ggcttacaga | ctgtcccaga | 180 |
| tttcttctcg | tggctcaaat | ataactattc | atccctgag | aacatcatg | gatatggtct | 240 |
| atgtgggtaa | atcaccatt | ggaacacccc | ctcaggaatt | ccaggttgtc | tttgacacag | 300 |
| gctcatctga | gttgtgggtg | ccctccgtct | tttgccccag | ttcagcctgt | tctactcaca | 360 |
| ttaggttcag | acatcttgag | tcttccactt | ccggcctaac | ccaaaagacc | ttcagcatca | 420 |
| cctatggatc | tgggagcacg | aagggatttc | ttgcttatga | caccgttcgg | attggggacc | 480 |
| ttctaagtac | tgatcaggaa | ttcggactaa | gcatggaaga | acacgggttt | gaggatctac | 540 |
| cttttgatgg | cgtcttgggc | ttgaactacc | ctgacatgtc | cttcataaca | accatcccca | 600 |
| tctttgacaa | cctcaagaat | caaggtgcct | tttctgagcc | tgttttgcc | ttctacttgg | 660 |
| gcaaggtgaa | gggcagtgtg | gtgatgtttg | gtggggtgga | ccacacctac | tacaagggag | 720 |
| agctcaactg | ggtgccattg | atccaggcag | gtgagtggag | tctacacatg | gaccgcatct | 780 |
| ccatgaaaag | aaaggttatt | gcttgttctg | gtggctgcga | ggccttctat | gacactggaa | 840 |
| catcactgat | ccttggccca | agaagactgg | tcaataacat | ccagaagctc | atcggtgcca | 900 |
| cgccacaggg | ttccgagcac | tacatttcat | gttttgctgt | catatccctg | ccctctatta | 960 |
| tcttcaccat | caacggcatc | aacatcccag | tgccagctcg | agcctacatc | cacaaggatt | 1020 |
| ctagaggcca | ctgctatccc | acctttaaag | agaacacagt | gagtacatcc | acagagacct | 1080 |
| ggatcctggg | tgacgtcttc | ctgaggctct | atttctcagt | ttttgatcga | ggaaatgaca | 1140 |
| ggattggcct | ggcacaggtg | taaatgcttg | gagtggttca | ggaatcagta | aggccgctcc | 1200 |
| taacacacac | tcactcacac | tttgagactc | ctgcccagga | tgctggtgaa | ctgtatttgg | 1260 |
| tggtctgcac | accctattct | caggaaagaa | taaagggttt | cactcttaat | ggtgctg | 1317 |

<210> SEQ ID NO 6
<211> LENGTH: 1322
<212> TYPE: DNA
<213> ORGANISM: bovidae

<400> SEQUENCE: 6

| | | | | | |
|---|---|---|---|---|---|
| ggagccagaa | aatcacatga | agtggcttgt | gctcctcggg | ctggtggcct | tctcagagtg | 60 |
| catagtcaaa | ataccctcaa | ggagagtgaa | gacaatgaga | aatgctatca | gtggaaaaaa | 120 |
| cacgctgaac | aatatcctga | aggagcatgc | ttacagactg | ccccagattt | cttttcgtgg | 180 |
| ctcaaatcta | actcacccac | tgagaaacat | cagggatttg | ttctacgtgg | gtaacatcac | 240 |
| cattgggaca | ccccctcagg | aattccaggt | tatctttgac | acaggctcat | ctgacttgtg | 300 |
| ggtggcctcc | atcttttgca | acagctcatc | ctgtgctgca | cacgttaggt | tcagacatca | 360 |
| tcagtcttcc | accttccggc | ctaccaataa | gaccttcagg | atcacctatg | gatctgggag | 420 |
| aatgaaagga | gttgttgttc | atgacacagt | tcggattggg | gaccttgtaa | gtactgacca | 480 |
| gccattcggt | ctatgcctga | aagactctgg | gtttaagggc | atacctttg | atggcatctt | 540 |
| gggcttgagc | taccccaaca | aaaccttctc | tggagccttc | cccatctttg | acaagctgaa | 600 |

-continued

| | |
|---|---|
| gaatgaaggt gccatttctg agcctgtttt tgccttctac ttgagcaaag acaagcagga | 660 |
| gggcagtgtg gtgatgtttg gtggggtgga ccaccgctac tacaagggggg agctcaactg | 720 |
| ggtaccattg atccaagtgg gtgactggtt tgtacacatg gaccgcacta ccatgaaaag | 780 |
| aaaggttatt gcttgttctg atggctgcaa ggcccttgtg gacaccggga catcagatat | 840 |
| cgtaggccca agtacactgg tcaataacat ctggaagctc atccgtgcca ggccactggg | 900 |
| tcctcagtac ttcgtttcat gttctgcggt caatacactg ccctctatta tcttcaccat | 960 |
| caacggcatc aactaccgac tgccagctcg agcctacatc acaaggatt ctagaggccg | 1020 |
| ctgctatacc gcctttaaag agcaccgatt cagttcacct atagagacct ggctcctggg | 1080 |
| tgacgtcttc ctgaggcggt atttctcagt ctttgatcga ggaaatgaca ggattggcct | 1140 |
| ggcacgggca gtgtaaatgc ttagagtggc tcaggaatca gtaaggccgt tcctaacaca | 1200 |
| ccttaactca cactttgggc actcttgcct aggatgctgg tgaactgtat ttggtgctcg | 1260 |
| tacacccatt ctagtaaaga ataaagggtt tcacttaacg ggtgctgaaa aaaaaaaaa | 1320 |
| aa | 1322 |

<210> SEQ ID NO 7
<211> LENGTH: 1211
<212> TYPE: DNA
<213> ORGANISM: bovidae

<400> SEQUENCE: 7

| | |
|---|---|
| acaccaaaac ttccctgagt acttggaacc aggaaagaag catgaagtgg cttgtgctcc | 60 |
| tcgggctggt ggccttctca gagtgcatag tcaaaatacc tctaaggaga gtgaagacca | 120 |
| tgagaaaaac tctcagtgga aaaaacatgc tgaacaattt cttgaaggag gatccttaca | 180 |
| gactgtccca catttctttt cgtggctcaa atctaactat tcacccgctg agaaacatca | 240 |
| gagatatctt ctatgtcgga aacatcacca ttggaacacc ccctcaggaa ttccaggtta | 300 |
| tctttgacac aggctcatct gacttgtggg tgccctcgat cgattgcaac agtacatcct | 360 |
| gtgctacaca tgttaggttc agacatcttc agtcttccac cttccggcct accaataaga | 420 |
| ccttcaggat catctatgga tctgggagaa tgaacggagt tattgcttat gacacagttc | 480 |
| ggattgggga ccttgtaagt accgaccagc catttggtct aagcgtggag gaatatgggt | 540 |
| ttgcgcacaa aagatttgat ggcatcttgg gcttgaacta ctggaaccta tcctggtcta | 600 |
| aggccatgcc catctttgac aagctgaaga tgaaggtgc catttctgag cctgttttg | 660 |
| ccttctactt gagcaacatc accatgaaca gagaggttat tgcttgttct gaaggctgtg | 720 |
| cggcccttgt ggacactggg tcatcaaata tccaaggccc aggaagactg attgataaca | 780 |
| tacagaggat catcggcgcc acgccacggg gttccaagta ctacgtttca tgttctgcgg | 840 |
| tcaatatcct gccctctatt atcttcacca tcaacgcgt caactaccca gtgccacctc | 900 |
| gagcttacat cctcaaggat tctagaggcc actgctatac caccttttaaa gagaaaagag | 960 |
| tgaggagatc tacagagagc tgggtcctgg gtgaagtctt cctgaggctg tatttctcag | 1020 |
| tctttgatcg aggaaatgac aggattggcc tggcacggcg agtgtaaatg cttggtctgg | 1080 |
| ctcaagaatc attaaggcca ctcctaacac acactcactc cactttggg cactgctgcc | 1140 |
| aggatgctgg tgaactgtat ttgtgttctg tacacccat tctcagtaaa gaataaaggg | 1200 |
| tttcagctct t | 1211 |

<210> SEQ ID NO 8
<211> LENGTH: 1340
<212> TYPE: DNA
<213> ORGANISM: bovidae

<400> SEQUENCE: 8

```
caggaattcg cggccgcgtc gacggaaaga agcatgaagt ggcttgtgct tctcgggctg      60
gtggccctct cagagtgcat agtcaaaatc cctctaacga agatgaagac catgcaagaa     120
gccatcaggg aaaaacaatt gctggaagat ttcttggatg aacaacctca cagcctgtcc     180
cagcattctg atcctgacaa gaaattctct tctcaccaac tgaagaattt ccagaatgct     240
gtctactttg gtacgatcac cattggaaca cctcctcaag agttccaggt caactttgac     300
accggctcat ctgacttgtg ggtgccctct gtcgactgcc aaagtccctc ctgctctaaa     360
cataagagat cgaccctca gaagtccacc accttccagc ctttgaacca gaaaattgaa     420
ctcgtctacg gctctgggac catgaaaggg gttcttggct ctgacaccat tcagatcggg     480
aaccttgtca tcgtgaacca gattttttggc ttgagccaga atcagtccag tggcgtcctg     540
gaacaagtac cttatgatgg catcctgggc ttggcctacc ccagcctcgc catccagggg     600
accaccccag tcttcgacaa cctgaagaat cgagaagtca tttctgagcc agtctttgcc     660
ttctacttga gctcccggcc agaaaacatc agcacggtga tgtttggcgg ggtggaccac     720
acctaccaca agggaaaact ccagtggatc ccagtgaccc aagcccgctt ctggcaggta     780
gccatgagca gcatgaccat gaacgggaat gtggtcggtt gttcccaagg atgtcaggcc     840
gttgtggata ctgggacctc gttgctggtt ggccaactc acctggtcac tgacatcctg     900
aagctcatca accctaatcc tatcctgaat gacgagcaaa tgctttcatg tgatgccatc     960
aatagcctgc ctacgctcct cctcaccatc aacggcatcg tctaccctgt gcccctgac    1020
tactacatcc agaggttttc tgaaaggatc tgctttatca gctttcaagg gggcacagag    1080
atcttgaaaa atttgggaac ctcggagacc tggatcctgg gtgatgtctt cctgaggctg    1140
tatttttcag tttatgaccg aggaaataac aggattggcc tggctcctgc agcataaatt    1200
cgggctgcta caggaatcaa tcagggccag acaaacacac actcactcac atgcagggcc    1260
atcccaccca gggatgctgg tgaactatgc ctgatgctct gcaaagccgt attctcagta    1320
aagaataaaa gattcatttc                                               1340
```

<210> SEQ ID NO 9
<211> LENGTH: 1311
<212> TYPE: DNA
<213> ORGANISM: bovidae

<400> SEQUENCE: 9

```
acccccaaact tccctgagta cctggagcca gtaaagaagc atgaagtgga ttgtgctcct      60
cgggctggtg gccttctcag agtgcatagt caaatacct ctaaggcaag tgaagaccat     120
gagaaaaacc ctcagtggaa aaacatgct gaagaatttc ttgaaggagc atccttacag     180
actgtcccag atttctttc gtggctcaaa tctaactatt caccgctga ggaacatcat     240
gaatttggtc tacgtgggta acatcaccat tggaacaccc cctcaggaat tccaggttgt     300
ctttgacaca ggctcatctg acttgtgggt gccctccttt tgtaccatgc cagcatgctc     360
tgcaccggtt tggttcagac aacttcagtc ttccaccttc cagcctacca ataagacctt     420
caccatcacc tatggatctg ggagcatgaa gggattcttt gcttatgaca cagttcggat     480
tggggacctt gtaagtactg atcagccgtt cggtctaagc gtggtggaat atgggttgga     540
```

-continued

```
gggcagaaat tatgatggtg tcttgggctt gaactacccc aacatatcct tctctggagc      600
catccccatc tttgacaacc tgaagaatca aggtgccatt tctgagcctg tttttgcctt      660
ctacttgagc aaaaacaagc aggagggcag tgtggtgatg tttggtgggg tggaccacca      720
gtactacaag ggagagctca actggatacc actgattgaa gcaggcgaat ggagagtaca      780
catggaccgc atctccatga aaagaacggt tattgcttgt tctgatggct gtgaggccct      840
tgtgcacact gggacatcac atatcgaagg cccaggaaga ctggtgaata acatacacag      900
gctcatccgc accaggccat tgattccaa gcactacgtt tcatgttttg ccaccaaata       960
cctgccctct attactttca tcatcaacgg catcaagtac ccaatgacag ctcgagccta     1020
catctttaag gattctagag ccgctgcta ttccgctttt aaagagaaca cagtgagaac      1080
atctagagag acctggatcc tcggtgatgc cttcctgagg cggtatttct cagtctttga     1140
tcgaggaaat gacaggattg gcctggcacg ggcagtgtaa atgcttagag tggttcagga     1200
atcagtaagg ccgttcctaa cacacactaa ctcacacttt gggcactctt gcctaggatg     1260
ctggtgaacc tgtctttggt ggtcttgtac caccctattc tcagtaaaga a              1311

<210> SEQ ID NO 10
<211> LENGTH: 1328
<212> TYPE: DNA
<213> ORGANISM: bovidae

<400> SEQUENCE: 10
tccgactctg tcttgagcac ttcagtggag gacaaaagca tgaagtggct tggacttctc       60
gggctggtag ctctctcaga gtgcatggtc ataatccctc ttaggcaaat gaagaccatg      120
cgagaaaccc taagggaaag acatttgctg acaaatttct ctgaggaaca cccttacaac      180
ctgtcccaga aagctgctaa tgatcaaaac ataatttatc atcatccctt gaggagctat      240
aaggattttt cctacatcgg caacatcaac attggaacac cccctcagga gttccaggtc      300
ctctttgaca ccggctcatc tagcttgtgg gtgccctcca tatactgcca gagttccagc      360
tgctataaac acaatagctt cgtcccttgt aactcctcca ccttcaaggc cacgaacaag      420
atcttcaata ccaactacac cgctacatcg ataaagggat atcttgtcta tgacactgtt      480
cggatcggga accttgttag tgtggcccag ccatttggcc taagcctgaa ggagtttggg      540
tttgacgatg taccatttga tggcatcctg ggactaggtt acccacgccg cactatcaca      600
ggggccaacc cgatcttcga caacctgtgg aaacaaggag tcatttctga gcctgtcttt      660
gccttctact tgagcagtca gaaagagaac ggcagcgtgg tgatgtttgg agggggtgaac      720 cgtgcctact ataagggaga actcaactgg gtaccagtgt cccaagtggg cagctggcat      780
ataaacatag acagcatctc catgaatggg acagtggttg cttgtaaacg tggctgccag      840
gcctcttgga tacggggacg cctttctgcg tggcccaaga ggatcgtcag caaaatccag      900
aaactcatcc atgccaggcc catcgatcgt gagcacgtgg tttcctgcca agccatcggg      960
acactgcctc ctgctgtctt cactatcaat gggatagact atccagtacc cgcccaagct     1020
tacatccaaa gtttgtcggg ctactgcttc agcaactttc ttgtgcgccc acagcgtgtg     1080
aacgagtcgg agacctggat cctgggtgac gtcttcctga ggctgtattt ctcagttttc     1140
gatcgaggaa acaacaggat tggcctggct cccgcagtgt aaatgctggg ctacttcagg     1200
aatcaatcag gcccactcca aacacatact catgtgaggg caccctgggt ggggccaggg     1260
atgctggtga actctgtttg ttgcgctgca aagccctact ctctatagag aataaaggat     1320
ttcatctc                                                            1328
```

<210> SEQ ID NO 11
<211> LENGTH: 1285
<212> TYPE: DNA
<213> ORGANISM: bovidae

<400> SEQUENCE: 11

| | | |
|---|---|---|
| gagatgaagt ggcttgtgtt ccttgggctg gtggccttct cagagtgcat agtcataatg | 60 |
| cttctaacta aaacgaagac aatgcgagaa atctggaggg aaaaaaaatt gctgaacagt | 120 |
| ttcctggagg aacaagccaa tagaatgtcc gatgattctg ctagtgaccc caaattatct | 180 |
| actcaccccc tgaggaacgc tctggatatg gcctatgtgg gtaacatcac cattggaaca | 240 |
| cccctaagg agttccgggt tgtctttgac acgggctcat ctgacttgtg ggtgccctcc | 300 |
| atcaagtgca tcagtcctgc ctgtcataca catattacct tcgaccatca caaatcttcc | 360 |
| accttccggc ttacgcgcag gcccttccac atcctctacg gatctgggat gatgaacgga | 420 |
| gttcttgcct atgacactgt tcggatcggg aaacttgtca gcactgacca gccgtttggc | 480 |
| ctaagcctgc agcaattcgg gtttgataat gcacccttg atggtgtcct gggcttgtcc | 540 |
| taccccagcc tcgctgtccc aggaaccatc cccatctttg acaagctgaa gcaacaaggt | 600 |
| gccatttctg aacctatctt tgccttctac ttgagcaccc gcaaggagaa tggcagtgtg | 660 |
| ttgatgttag gtggggtgga ccactcctac cacaagggaa agctcaactg gataccagtg | 720 |
| tcccaaacca aaagctggct aataactgtg gaccgcatct ccatgaatgg gagagtgatt | 780 |
| ggctgtgaac acggctgcga ggctcttgtg gataccggga catcactgat ccatggccca | 840 |
| gcaagaccag tcaccaacat ccaaaagttc atccacgcta tgccctacgg ttccgagtac | 900 |
| atggttttgt gtcctgtcat cagtatcctg cctcctgtca tcttcaccat caatggcatc | 960 |
| gattactcag tgcctcgtga agcctacatc caaaagattt ctaatagctt atgccttagc | 1020 |
| acctttcatg gggacgacac agaccaatgg atcctgggtg acgtcttcct gaggctgtat | 1080 |
| ttctcagttt atgaccgagg aaataacagg attggcctgg ctcctgctgt gtaaatgctt | 1140 |
| ggacttgttc aggaatcatt caggccagtc ctaacacaca cttgctcaca ctttagactc | 1200 |
| ctgcccagga tgctggtaaa ctgtgtttgg tgctctgaaa gtcatattct cactgaaaaa | 1260 |
| taaaaggttt cactcttaac atctt | 1285 |

<210> SEQ ID NO 12
<211> LENGTH: 1130
<212> TYPE: DNA
<213> ORGANISM: bovidae

<400> SEQUENCE: 12

| | | |
|---|---|---|
| atgaagtggc ttgtgctcct cgggctggtg gccctctcag agtgcatagt cattttgcct | 60 |
| ctaaggaaaa tgaagacctt gcgagaaacc tgagggaaa aaacttgct gaacaatttc | 120 |
| ctggaagaac gagcttacag actgtccaag aaagactcca aataactat tcaccccctt | 180 |
| aaaactatct ggatatggcc tacgtgggta atatcaccat tggaacaccc cctcaggaat | 240 |
| tccgggtcgt ctttgacaca ggctcagctg acttgtgggt gccttccatc agctgtgtca | 300 |
| gtccagcctg ttatacacac aaaaccttca atcttcacaa ttcttccagc ttcgggcaaa | 360 |
| cacaccagcc tattagcatc tcctatggac ctgggataat tcaggatttt cttggctctg | 420 |
| acaccgttcg gatcgggaac cttgttagcc ttaaacagtc gtttggccta agccaggagg | 480 |
| aatatggggtt tgatggtgca ccctttgatg gcgtcctggg cttggcctac ccctccatca | 540 |
| gcatcaaagg tatcatcccc atctttgaca acttgtggtc gcaaggtgcc ttttctgaac | 600 |

```
ctgtctttgc cttctacttg aacacatgcc agccggaagg cagtgtggtg atgtttggtg      660
gagtggacca ccgctactac aagggagagc tcaactggat accagtgtcc caaactcgct      720
actggcagat aagcatgaac cgcatcagca tgaacgggaa tgttactgct tgttctcgtg      780
gatgtcaggc ccttttggac accgggacat caatgatcca tggcccaaca agactgatca      840
ccaacatcca caagctcatg aacgccaggc caggggttc ggagtatgtg gtttcatgtg      900
atgccgtcaa gaccctgcct cctgtcatct tcaacatcaa tggcatcgac tatccactgc      960
cccctcaagc ctacatcacc aaggctcaaa acttctgcct tagcatcttt catggggca      1020 cagaaactag ctctccagag acctggatcc tgggtggcgt cttcctgaga cagtacttct      1080 cagttttga tcgaagaaat gacagtattg gcctggcaca ggtgtaaatg      1130
```

`<210>` SEQ ID NO 13
`<211>` LENGTH: 1173
`<212>` TYPE: DNA
`<213>` ORGANISM: bovidae

`<400>` SEQUENCE: 13

```
cccaagctta tgaagtggct tgtgctcctc gggctggtgg ccctctcaga gtgcatagtc       60
attttgcctc taagaaaat gaagaccttg cgagaaaccc tgagggaaaa aaacttgctg      120
aacaatttcc tggaggaaca agcttacaga ctgtccaaga atgactccaa ataactatt      180 caccccctga ggaactatct ggatactgcc tacgtgggta acatcaccat ggaacaccc      240 cctcaggagt tccgggtcgt ctttgacaca ggctcagcta acttgtgggt gccctgcatc      300
acctgtacca gtccagcctg ttatacacac aaaaccttca atcctcaaaa ttcttcaagc      360
ttccgggaag taggctcgcc tatcaccatc ttctatggat ctgggataat tcagggattt      420
cttggctctg acaccgttcg gatcgggaac cttgttagcc ttaaacagtc gtttggccta      480
agccaggagg aatatgggtt tgatggtgca cccttttgatg gcgtcctggg cttggcctac      540
ccctccatca gcatcaaagg tatcatcccc atctttgaca acttgtggtc gcacggtgcc      600
ttttctgagc ctgtcttcgc cttctacttg aacacaaaca agccagaggg cagtgtggtg      660
atgtttggtg gggtggacca ccgctactac aagggagagc tcaactggat accagtgtcc      720
caaactagcc attggcagat aagcatgaac aacatcagca tgaatgggac tgtgacggct      780
tgttcttgtg gatgtgaggc ccttttggac accgggacat caatgatcta cggcccaaca      840
aaactggtca ccaacatcca caagctcatg aacgccaggc ttgagaattc tgagtatgtg      900
gtttcatgtg atgctgtcaa gaccctgcct cctgtcatct tcaacatcaa tggcatcgac      960
tatccactgc ccctcaagc ctacatcatc aagattcaaa acaactgccg cagcgtctt      1020 caaggaggca cagaaaatag ctctctaaac acctggatcc ttggtgatat cttcctgagg      1080
cagtacttct cggttttga tcgtaaaaat agaaggattt gctggcacag gtgggtaccg      1140
actacaagga cgacgatgac aagtaagctt ccg      1173
```

`<210>` SEQ ID NO 14
`<211>` LENGTH: 1176
`<212>` TYPE: DNA
`<213>` ORGANISM: bovidae

`<400>` SEQUENCE: 14

```
cccaagctta tgaagtggct tgtgctcctt gcgctggtgg ccttctcaga gtgcataatc       60
aaaataccct caaggagagt gaagaccatg agcaataccg ccagtggaaa aaacatgctg      120
aacaatttcc tgaagaagca tccttacaga ttgtcccaga tttcttttcg tggctcaaat      180
```

-continued

| | |
|---|---|
| ctcactactc acccactgat gaacatctgg gatttgctct acctgggtaa catcaccatt | 240 |
| ggaacacccc ctcaggaatt ccaggttctc tttgacacag gctcatctga cttgtgggtc | 300 |
| ccctctctct tgtgcaacag ctcaacctgt gctaaacacg ttatgttcag acatcgtctg | 360 |
| tcttccacct accggcctac aataagacc ttcatgatct tctatgcagt tgggaaaatt | 420 |
| gaaggagttg ttgttcgtga cacagttcgg attgggacc ttgtaagtgc ggaccagacg | 480 |
| tttggtctaa gcattgcaga aactgggttt gagaacacaa ctcttgatgg catcttgggc | 540 |
| ttgagctacc ccaacacatc ctgctttgga accatcccca tctttgacaa gctgaagaat | 600 |
| gaaggtgcca tttctgagcc tgtactacat agtgtgagac gcaaagatga gcaggagggc | 660 |
| agtgtagtga tgtttggtgg tgtggaccac agttactaca agggagagct caactgggta | 720 |
| ccattgatca aagcaggcga ctggagtgta cgtgtgaca gcatcaccat gaaaagagag | 780 |
| gttattgctt gttctgacgg ctgcagggcc ctggtggaca ccggttcatc acatatccaa | 840 |
| ggcccaggaa gactgatcga taacgtacag aagctgatag gcaccatgcc acagggatcc | 900 |
| atgcactatg ttccatgttc tgcggtcaat accctgccct ctattatctt caccatcaac | 960 |
| agcatcagct acacagtgcc agctcaagcc tacatcctca agggttctag ggccgctgc | 1020 |
| tattccacct ttcaagggca cactatgagt tcatctacag agacctggat cctgggtgat | 1080 |
| gtcttcctga gtcagtattt ctcggtcttt gatcgaggaa atgacaggat tggcctggca | 1140 |
| caggtgggta ccgactacaa ggacgacgat gaaagt | 1176 |

<210> SEQ ID NO 15
<211> LENGTH: 1360
<212> TYPE: DNA
<213> ORGANISM: Felis domestica

<400> SEQUENCE: 15

| | |
|---|---|
| aggaaagaag catgaagtgg ctttgggtcc ttgggctggt ggccctctca gagtgcttag | 60 |
| tcacaatccc tctgacgagg gtcaagtcca tgcgagaaaa cctcagggag aaagacaggc | 120 |
| tgaaggattt cctggagaac catccttaca acctggccta caagtttgtt gactctgtaa | 180 |
| atctggacct ggggatatat tttgaaccga tgaggaacta cctggatctg gcctacgttg | 240 |
| gcaccatcag cattggaacg cccccccagg agttcaaggt catctttgac accggctcat | 300 |
| ctgacttgtg ggtgccctcc atctactgct ctagccctgc ctgcgctaat cacaacgtct | 360 |
| tcaaccctct gcggtcctcc accttccgga tctcgggccg gcccatccac ctccagtacg | 420 |
| gctccgggac gatgtcagga tttctggcct acgacaccgt tcggttcggg ggcctcgttg | 480 |
| acgtggccca gcgtttggc ctgagcctga gggagcccgg caagttcatg aatacgcag | 540 |
| ttttcgacgg catcctgggc ctggcctacc ccagcctcag cctcagaggg accgtccctg | 600 |
| tcttcgacaa cctgtggaag cagggtctca tttctcagga gctctttgcc ttctacttga | 660 |
| gcaaaaagga cgaagaaggc agtgtggtga tgttcggcgg tgtggaccac tcctactaca | 720 |
| gcggagacct caactgggtg ccggtgtcca acggctgta ctggcagtta ccatggaca | 780 |
| gcatctccat gaacggggaa gtcattgctt gtgacggtgg ctgccaggcc atcattgata | 840 |
| caggaaccte gctgctgatt ggcccatctc acgttgtctt caacatccag atgatcatcg | 900 |
| gcgccaacca gtcctacagc ggcgagtacg tagttgactg cgatgccgcc aacaccctgc | 960 |
| ccgacatcgt cttcaccatc aacggcatcg actaccggt gccagccagt gcctacatcc | 1020 |
| aggagggtcc tcagggcacc tgctacagcg gctttgacga gagcggagac agcttgttgg | 1080 |
| tctcagactc ctggatcctg ggcgatgtct tcctgaggtt gtatttcacc gtcttcgacc | 1140 |

-continued

```
gagagaacaa caggattggc ctggccctgg cagtgtaaac actggggcca gctccaggaa    1200
gcaaccgtgc ccaccccaaa cccgcgcgcg cgtgtgcgca cacacacaca cacaccccc     1260 gcagtcaggg cattcctgcc caggggccgg cttgaactgt gtcttcggct ctgccaatcc    1320
cttctcccag tggagaataa aagacctcat cttccacggt                          1360
```

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:PCR primer

<400> SEQUENCE: 16

```
cccaagctta tgaagtggct tgtgctcct                                      29
```

<210> SEQ ID NO 17
<211> LENGTH: 69
<212> TYPE: DNA
<213> ORGANISM: Artificial Sequence
<220> FEATURE:
<223> OTHER INFORMATION: Description of Artificial Sequence:PCR primer

<400> SEQUENCE: 17

```
gggaagctta cttgtcatcg tcgtccttgt agtcggtacc cacctgtgcc aggccaatcc    60
tgtcatttc                                                            69
```

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 18

```
cctcttttgc cttctacttg a                                              21
```

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:PCR primer

<400> SEQUENCE: 19

```
gcgctcgagt tacactgccc gtgccaggc                                      29
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 20

```
tgggtaacat caccattgga a                                              21
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:PCR primer

```
<400> SEQUENCE: 21
tttctgagcc tgtttttgcc                                                   20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 22
tgggtaacat caccattgga ac                                                22

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 23
caaacatcac cacactgccc tcc                                               23

<210> SEQ ID NO 24
<211> LENGTH: 380
<212> TYPE: PRT
<213> ORGANISM: bovidae

<400> SEQUENCE: 24
```

| Met | Lys | Trp | Leu | Val | Leu | Leu | Gly | Leu | Val | Ala | Phe | Ser | Glu | Cys | Ile |
|---|---|---|---|---|---|---|---|---|---|---|---|---|---|---|---|
| 1 | | | | 5 | | | | | 10 | | | | | 15 | |

| Val | Lys | Ile | Pro | Leu | Arg | Arg | Leu | Lys | Thr | Met | Arg | Asn | Val | Val | Ser |
|---|---|---|---|---|---|---|---|---|---|---|---|---|---|---|---|
| | | | 20 | | | | | 25 | | | | | 30 | | |

| Gly | Lys | Asn | Met | Leu | Asn | Asn | Phe | Leu | Lys | Glu | His | Ala | Tyr | Ser | Leu |
|---|---|---|---|---|---|---|---|---|---|---|---|---|---|---|---|
| | | 35 | | | | | 40 | | | | | 45 | | | |

| Ser | Gln | Ile | Ser | Phe | Arg | Gly | Ser | Asn | Leu | Thr | Thr | His | Pro | Leu | Arg |
|---|---|---|---|---|---|---|---|---|---|---|---|---|---|---|---|
| | 50 | | | | | 55 | | | | | 60 | | | | |

| Asn | Ile | Lys | Asp | Leu | Val | Tyr | Met | Gly | Asn | Ile | Thr | Ile | Gly | Thr | Pro |
|---|---|---|---|---|---|---|---|---|---|---|---|---|---|---|---|
| 65 | | | | | 70 | | | | | 75 | | | | | 80 |

| Pro | Gln | Glu | Phe | Gln | Val | Val | Phe | Asp | Thr | Ala | Ser | Ser | Asp | Leu | Trp |
|---|---|---|---|---|---|---|---|---|---|---|---|---|---|---|---|
| | | | | 85 | | | | | 90 | | | | | 95 | |

| Val | Pro | Ser | Asp | Phe | Cys | Thr | Ser | Pro | Ala | Cys | Ser | Thr | His | Val | Arg |
|---|---|---|---|---|---|---|---|---|---|---|---|---|---|---|---|
| | | | 100 | | | | | 105 | | | | | 110 | | |

| Phe | Arg | His | Leu | Gln | Ser | Ser | Thr | Phe | Arg | Leu | Thr | Asn | Lys | Thr | Phe |
|---|---|---|---|---|---|---|---|---|---|---|---|---|---|---|---|
| | | 115 | | | | | 120 | | | | | 125 | | | |

| Arg | Ile | Thr | Tyr | Gly | Ser | Gly | Arg | Met | Lys | Gly | Val | Val | His | Asp |
|---|---|---|---|---|---|---|---|---|---|---|---|---|---|---|
| | 130 | | | | | 135 | | | | | 140 | | | |

| Thr | Val | Arg | Ile | Gly | Asn | Leu | Val | Ser | Thr | Asp | Gln | Pro | Phe | Gly | Leu |
|---|---|---|---|---|---|---|---|---|---|---|---|---|---|---|---|
| 145 | | | | | 150 | | | | | 155 | | | | | 160 |

| Ser | Ile | Glu | Glu | Tyr | Gly | Phe | Glu | Gly | Arg | Ile | Tyr | Asp | Gly | Val | Leu |
|---|---|---|---|---|---|---|---|---|---|---|---|---|---|---|---|
| | | | | 165 | | | | | 170 | | | | | 175 | |

| Gly | Leu | Asn | Tyr | Pro | Asn | Ile | Ser | Phe | Ser | Gly | Ala | Ile | Pro | Ile | Phe |
|---|---|---|---|---|---|---|---|---|---|---|---|---|---|---|---|
| | | | 180 | | | | | 185 | | | | | 190 | | |

| Asp | Lys | Leu | Lys | Asn | Gln | Arg | Ala | Ile | Ser | Glu | Pro | Val | Phe | Ala | Phe |
|---|---|---|---|---|---|---|---|---|---|---|---|---|---|---|---|
| | | 195 | | | | | 200 | | | | | 205 | | | |

| Tyr | Leu | Ser | Lys | Asp | Glu | Arg | Glu | Gly | Ser | Val | Val | Met | Phe | Gly | Gly |
|---|---|---|---|---|---|---|---|---|---|---|---|---|---|---|---|
| | 210 | | | | | 215 | | | | | 220 | | | | |

```
Val Asp His Arg Tyr Tyr Glu Gly Glu Leu Asn Trp Val Pro Leu Ile
225                 230                 235                 240

Gln Ala Gly Asp Trp Ser Val His Met Asp Arg Ile Ser Ile Glu Arg
            245                 250                 255

Lys Ile Ile Ala Cys Ser Asp Gly Cys Lys Ala Leu Val Asp Thr Gly
                260                 265                 270

Thr Ser Asp Ile Val Gly Pro Arg Arg Leu Val Asn Asn Ile His Arg
        275                 280                 285

Leu Ile Gly Ala Ile Pro Arg Gly Ser Glu His Tyr Val Pro Cys Ser
    290                 295                 300

Glu Val Asn Thr Leu Pro Ser Ile Val Phe Thr Ile Asn Gly Ile Asn
305                 310                 315                 320

Tyr Pro Val Pro Gly Arg Ala Tyr Ile Leu Lys Asp Asp Arg Gly Arg
                325                 330                 335

Cys Tyr Thr Thr Phe Gln Glu Asn Arg Val Ser Ser Ser Thr Glu Thr
                340                 345                 350

Trp Tyr Leu Gly Asp Val Phe Leu Arg Leu Tyr Phe Ser Val Phe Asp
        355                 360                 365

Arg Gly Asn Asp Arg Ile Gly Leu Ala Arg Ala Val
    370                 375                 380

<210> SEQ ID NO 25
<211> LENGTH: 376
<212> TYPE: PRT
<213> ORGANISM: bovidae

<400> SEQUENCE: 25

Met Lys Trp Leu Val Leu Leu Gly Leu Val Ala Leu Ser Glu Cys Ile
1               5                   10                  15

Val Ile Leu Pro Leu Lys Lys Met Lys Thr Leu Arg Glu Thr Leu Arg
            20                  25                  30

Glu Lys Asn Leu Leu Asn Asn Phe Leu Glu Glu Gln Ala Tyr Arg Leu
        35                  40                  45

Ser Lys Asn Asp Ser Lys Ile Thr Ile His Pro Leu Arg Asn Tyr Leu
    50                  55                  60

Asp Thr Ala Tyr Val Gly Asn Ile Thr Ile Gly Thr Pro Pro Gln Glu
65                  70                  75                  80

Phe Arg Val Val Phe Asp Thr Gly Ser Ala Asn Leu Trp Val Pro Cys
                85                  90                  95

Ile Thr Cys Thr Ser Pro Ala Cys Tyr Thr His Lys Thr Phe Asn Pro
                100                 105                 110

Gln Asn Ser Ser Ser Phe Arg Glu Val Gly Ser Pro Ile Thr Ile Phe
            115                 120                 125

Tyr Gly Ser Gly Ile Ile Gln Gly Phe Leu Gly Ser Asp Thr Val Arg
    130                 135                 140

Ile Gly Asn Leu Val Ser Pro Glu Gln Ser Phe Gly Leu Ser Leu Glu
145                 150                 155                 160

Glu Tyr Gly Phe Asp Ser Leu Pro Phe Asp Gly Ile Leu Gly Leu Ala
                165                 170                 175

Phe Pro Ala Met Gly Ile Glu Asp Thr Ile Pro Ile Phe Asp Asn Leu
                180                 185                 190

Trp Ser His Gly Ala Phe Ser Glu Pro Val Phe Ala Phe Tyr Leu Asn
            195                 200                 205

Thr Asn Lys Pro Glu Gly Ser Val Val Met Phe Gly Gly Val Asp His
    210                 215                 220
```

```
Arg Tyr Tyr Lys Gly Glu Leu Asn Trp Ile Pro Val Ser Gln Thr Ser
225                 230                 235                 240

His Trp Gln Ile Ser Met Asn Asn Ile Ser Met Asn Gly Thr Val Thr
            245                 250                 255

Ala Cys Ser Cys Gly Cys Glu Ala Leu Leu Asp Thr Gly Thr Ser Met
        260                 265                 270

Ile Tyr Gly Pro Thr Lys Leu Val Thr Asn Ile His Lys Leu Met Asn
    275                 280                 285

Ala Arg Leu Glu Asn Ser Glu Tyr Val Val Ser Cys Asp Ala Val Lys
290                 295                 300

Thr Leu Pro Pro Val Ile Phe Asn Ile Asn Gly Ile Asp Tyr Pro Leu
305                 310                 315                 320

Arg Pro Gln Ala Tyr Ile Ile Lys Ile Gln Asn Ser Cys Arg Ser Val
                325                 330                 335

Phe Gln Gly Gly Thr Glu Asn Ser Ser Leu Asn Thr Trp Ile Leu Gly
            340                 345                 350

Asp Ile Phe Leu Arg Gln Tyr Phe Ser Val Phe Asp Arg Lys Asn Arg
        355                 360                 365

Arg Ile Gly Leu Ala Pro Ala Val
    370                 375

<210> SEQ ID NO 26
<211> LENGTH: 381
<212> TYPE: PRT
<213> ORGANISM: bovidae

<400> SEQUENCE: 26

Met Asp Asp Leu Val Leu Leu Gly Leu Val Ala Phe Ser Glu Cys Ile
1               5                   10                  15

Val Lys Ile Pro Leu Arg Arg Val Lys Thr Met Arg Asn Thr Val Ser
                20                  25                  30

Gly Lys Asn Ile Leu Asn Asn Ile Leu Lys Glu His Val Tyr Arg Leu
            35                  40                  45

Ser Gln Ile Ser Phe Arg Gly Ser Asn Leu Thr Thr His Pro Leu Arg
        50                  55                  60

Asn Ile Lys Asp Leu Ile Tyr Val Gly Asn Ile Thr Ile Gly Thr Pro
65                  70                  75                  80

Pro Gln Glu Phe Gln Val Val Phe Asp Thr Gly Ser Ser Asp Phe Trp
                85                  90                  95

Val Pro Ser Asp Phe Cys Thr Ser Arg Ala Cys Ser Thr His Val Arg
                100                 105                 110

Phe Arg His Leu Gln Ser Ser Thr Phe Arg Leu Thr Asn Lys Thr Phe
            115                 120                 125

Arg Ile Thr Tyr Gly Ser Gly Arg Met Lys Gly Val Val Ala His Asp
130                 135                 140

Thr Val Arg Ile Gly Asp Leu Val Ser Thr Asp Gln Pro Phe Gly Leu
145                 150                 155                 160

Ser Val Glu Glu Tyr Gly Phe Glu Gly Arg Ala Tyr Tyr Asp Gly Val
                165                 170                 175

Leu Gly Leu Asn Tyr Pro Asn Ile Ser Phe Ser Gly Ala Ile Pro Ile
            180                 185                 190

Phe Asp Asn Leu Lys Asn Gln Gly Ala Ile Ser Glu Pro Val Phe Ala
        195                 200                 205

Ile Leu Leu Ser Lys Asp Glu Gln Glu Gly Ser Val Val Met Phe Gly
210                 215                 220
```

Gly Val Asp His Arg Tyr Tyr Glu Gly Glu Leu Asn Trp Val Pro Leu
225                 230                 235                 240

Ile Glu Ala Gly Asp Trp Ile Ile His Met Asp Arg Ile Ser Met Lys
            245                 250                 255

Arg Lys Ile Ile Ala Cys Ser Gly Ser Cys Glu Ala Ile Val Asp Thr
                260                 265                 270

Gly Thr Ser Ala Ile Glu Gly Pro Arg Lys Leu Val Asn Lys Ile His
            275                 280                 285

Lys Leu Ile Gly Ala Arg Pro Arg His Ser Lys Tyr Tyr Ile Ser Cys
        290                 295                 300

Ser Ala Val Asn Thr Leu Pro Ser Ile Ile Phe Thr Ile Asn Gly Ile
305                 310                 315                 320

Asn Tyr Pro Cys Pro Gly Arg Ala Tyr Val Leu Lys Asp Ser Arg Gly
                325                 330                 335

Arg Cys Tyr Ser Met Phe Gln Glu Asn Lys Val Ser Ser Ser Thr Glu
                340                 345                 350

Thr Trp Ile Leu Gly Asp Val Phe Leu Arg Val Tyr Phe Ser Val Phe
            355                 360                 365

Asp Arg Gly Asn Asp Arg Ile Gly Leu Ala Arg Ala Val
        370                 375                 380

<210> SEQ ID NO 27
<211> LENGTH: 380
<212> TYPE: PRT
<213> ORGANISM: bovidae

<400> SEQUENCE: 27

Met Lys Trp Leu Val Leu Leu Gly Leu Ala Phe Ser Glu Cys Ile
1               5                   10                  15

Val Lys Ile Pro Leu Arg Arg Val Lys Thr Met Thr Lys Thr Leu Ser
                20                  25                  30

Gly Lys Asn Met Leu Asn Asn Phe Val Lys Glu His Ala Tyr Arg Leu
            35                  40                  45

Ser Gln Ile Ser Phe Arg Gly Ser Asn Leu Thr Ile His Pro Leu Arg
        50                  55                  60

Asn Ile Arg Asp Phe Phe Tyr Val Gly Asn Ile Thr Ile Gly Thr Pro
65                  70                  75                  80

Pro Gln Glu Phe Gln Val Ile Phe Asp Thr Gly Ser Ser Glu Leu Trp
                85                  90                  95

Val Pro Ser Ile Phe Cys Asn Ser Thr Cys Ser Lys His Asp Arg
                100                 105                 110

Phe Arg His Leu Glu Ser Ser Thr Phe Arg Leu Ser Arg Arg Thr Phe
            115                 120                 125

Ser Ile Thr Tyr Gly Ser Gly Arg Ile Glu Ala Leu Val Val His Asp
        130                 135                 140

Thr Val Arg Ile Gly Asp Leu Val Ser Thr Asp Gln Gln Phe Gly Leu
145                 150                 155                 160

Cys Leu Glu Glu Ser Gly Phe Glu Gly Met Arg Phe Asp Gly Val Leu
                165                 170                 175

Gly Leu Ser Tyr Thr Asn Ile Ser Pro Ser Gly Ala Ile Pro Ile Phe
            180                 185                 190

Tyr Lys Leu Lys Asn Glu Gly Ala Ile Ser Glu Pro Val Phe Ala Phe
        195                 200                 205

Tyr Leu Ser Lys Asp Glu Arg Glu Gly Ser Val Val Met Phe Gly Gly
210                 215                 220

```
Ala Asp His Arg Tyr Tyr Lys Gly Glu Leu Asn Trp Ile Pro Leu Met
225                 230                 235                 240

Lys Ala Gly Asp Trp Ser Val His Met Asp Arg Ile Ser Met Lys Arg
            245                 250                 255

Lys Val Ile Ala Cys Ser Gly Cys Lys Ala Leu Val Asp Thr Gly
        260                 265                 270

Ser Ser Asp Ile Val Gly Pro Ser Thr Leu Val Asn Asn Ile Trp Lys
    275                 280                 285

Leu Ile Gly Ala Thr Pro Gln Gly Ser Glu His Tyr Val Ser Cys Ser
290                 295                 300

Ala Val Asn Ser Leu Pro Ser Ile Ile Phe Thr Ile Lys Ser Asn Asn
305                 310                 315                 320

Tyr Arg Val Pro Gly Gln Ala Tyr Ile Leu Lys Asp Ser Arg Gly Arg
                325                 330                 335

Cys Phe Thr Ala Phe Lys Gly His Gln Gln Ser Ser Ser Thr Glu Met
            340                 345                 350

Trp Ile Leu Gly Asp Val Phe Leu Arg Leu Tyr Phe Ser Val Phe Asp
        355                 360                 365

Arg Arg Lys Asp Arg Ile Gly Leu Ala Thr Lys Val
370                 375                 380

<210> SEQ ID NO 28
<211> LENGTH: 377
<212> TYPE: PRT
<213> ORGANISM: bovidae

<400> SEQUENCE: 28

Met Lys Trp Leu Val Leu Leu Gly Leu Leu Thr Ser Ser Glu Cys Ile
1               5                   10                  15

Val Ile Leu Pro Leu Thr Lys Val Lys Thr Met Arg Lys Thr Leu Ser
            20                  25                  30

Glu Lys Asn Met Leu Asn Asn Phe Leu Lys Glu Gln Ala Tyr Arg Leu
        35                  40                  45

Ser Gln Ile Ser Ser Arg Gly Ser Asn Ile Thr Ile His Pro Leu Arg
    50                  55                  60

Asn Ile Met Asp Met Val Tyr Val Gly Lys Ile Thr Ile Gly Thr Pro
65                  70                  75                  80

Pro Gln Glu Phe Gln Val Val Phe Asp Thr Gly Ser Ser Glu Leu Trp
                85                  90                  95

Val Pro Ser Val Phe Cys Pro Ser Ser Ala Cys Ser Thr His Ile Arg
            100                 105                 110

Phe Arg His Leu Glu Ser Ser Thr Ser Gly Leu Thr Gln Lys Thr Phe
        115                 120                 125

Ser Ile Thr Tyr Gly Ser Gly Ser Thr Lys Gly Phe Leu Ala Tyr Asp
    130                 135                 140

Thr Val Arg Ile Gly Asp Leu Leu Ser Thr Asp Gln Glu Phe Gly Leu
145                 150                 155                 160

Ser Met Glu Glu His Gly Phe Glu Asp Leu Pro Phe Asp Gly Val Leu
                165                 170                 175

Gly Leu Asn Tyr Pro Asp Met Ser Phe Ile Thr Thr Ile Pro Ile Phe
            180                 185                 190

Asp Asn Leu Lys Asn Gln Gly Ala Phe Ser Glu Pro Val Phe Ala Phe
        195                 200                 205

Tyr Leu Gly Lys Val Lys Gly Ser Val Val Met Phe Gly Gly Val Asp
    210                 215                 220
```

```
His Thr Tyr Tyr Lys Gly Glu Leu Asn Trp Val Pro Leu Ile Gln Ala
225                 230                 235                 240

Gly Glu Trp Ser Leu His Met Asp Arg Ile Ser Met Lys Arg Lys Val
            245                 250                 255

Ile Ala Cys Ser Gly Gly Cys Glu Ala Phe Tyr Asp Thr Gly Thr Ser
        260                 265                 270

Leu Ile Leu Gly Pro Arg Arg Leu Val Asn Asn Ile Gln Lys Leu Ile
    275                 280                 285

Gly Ala Thr Pro Gln Gly Ser Glu His Tyr Ile Ser Cys Phe Ala Val
290                 295                 300

Ile Ser Leu Pro Ser Ile Ile Phe Thr Ile Asn Gly Ile Asn Ile Pro
305                 310                 315                 320

Val Pro Ala Arg Ala Tyr Ile His Lys Asp Ser Arg Gly His Cys Tyr
            325                 330                 335

Pro Thr Phe Lys Glu Asn Thr Val Ser Thr Ser Thr Glu Thr Trp Ile
        340                 345                 350

Leu Gly Asp Val Phe Leu Arg Leu Tyr Phe Ser Val Phe Asp Arg Gly
    355                 360                 365

Asn Asp Arg Ile Gly Leu Ala Gln Val
370                 375

<210> SEQ ID NO 29
<211> LENGTH: 379
<212> TYPE: PRT
<213> ORGANISM: bovidae

<400> SEQUENCE: 29

Met Lys Trp Leu Val Leu Leu Gly Leu Val Ala Phe Ser Glu Cys Ile
1               5                   10                  15

Val Lys Ile Pro Leu Arg Arg Val Lys Thr Met Arg Asn Ala Ile Ser
            20                  25                  30

Gly Lys Asn Thr Leu Asn Asn Ile Leu Lys Glu His Ala Tyr Arg Leu
        35                  40                  45

Pro Gln Ile Ser Phe Arg Gly Ser Asn Leu Thr His Pro Leu Arg Asn
    50                  55                  60

Ile Arg Asp Leu Phe Tyr Val Gly Asn Ile Thr Ile Gly Thr Pro Pro
65                  70                  75                  80

Gln Glu Phe Gln Val Ile Phe Asp Thr Gly Ser Ser Asp Leu Trp Val
            85                  90                  95

Ala Ser Ile Phe Cys Asn Ser Ser Cys Ala Ala His Val Arg Phe
        100                 105                 110

Arg His His Gln Ser Ser Thr Phe Arg Pro Thr Asn Lys Thr Phe Arg
        115                 120                 125

Ile Thr Tyr Gly Ser Gly Arg Met Lys Gly Val Val His Asp Thr
    130                 135                 140

Val Arg Ile Gly Asp Leu Val Ser Thr Asp Gln Pro Phe Gly Leu Cys
145                 150                 155                 160

Leu Lys Asp Ser Gly Phe Lys Gly Ile Pro Phe Asp Gly Ile Leu Gly
            165                 170                 175

Leu Ser Tyr Pro Asn Lys Thr Phe Ser Gly Ala Phe Pro Ile Phe Asp
        180                 185                 190

Lys Leu Lys Asn Glu Gly Ala Ile Ser Glu Pro Val Phe Ala Phe Tyr
    195                 200                 205

Leu Ser Lys Asp Lys Gln Glu Gly Ser Val Val Met Phe Gly Gly Val
210                 215                 220
```

```
Asp His Arg Tyr Tyr Lys Gly Glu Leu Asn Trp Val Pro Leu Ile Gln
225                 230                 235                 240

Val Gly Asp Trp Phe Val His Met Asp Arg Thr Thr Met Lys Arg Lys
            245                 250                 255

Val Ile Ala Cys Ser Asp Gly Cys Lys Ala Leu Val Asp Thr Gly Thr
        260                 265                 270

Ser Asp Ile Val Gly Pro Ser Thr Leu Val Asn Asn Ile Trp Lys Leu
    275                 280                 285

Ile Arg Ala Arg Pro Leu Gly Pro Gln Tyr Phe Val Ser Cys Ser Ala
290                 295                 300

Val Asn Thr Leu Pro Ser Ile Ile Phe Thr Ile Asn Gly Ile Asn Tyr
305                 310                 315                 320

Arg Leu Pro Ala Arg Ala Tyr Ile His Lys Asp Ser Arg Gly Arg Cys
            325                 330                 335

Tyr Thr Ala Phe Lys Glu His Arg Phe Ser Ser Pro Ile Glu Thr Trp
        340                 345                 350

Leu Leu Gly Asp Val Phe Leu Arg Arg Tyr Phe Ser Val Phe Asp Arg
    355                 360                 365

Gly Asn Asp Arg Ile Gly Leu Ala Arg Ala Val
370                 375

<210> SEQ ID NO 30
<211> LENGTH: 341
<212> TYPE: PRT
<213> ORGANISM: bovidae

<400> SEQUENCE: 30

Met Lys Trp Leu Val Leu Leu Gly Leu Val Ala Phe Ser Glu Cys Ile
1               5                   10                  15

Val Lys Ile Pro Leu Arg Arg Val Lys Thr Met Arg Lys Thr Leu Ser
            20                  25                  30

Gly Lys Asn Met Leu Asn Asn Phe Leu Lys Glu Asp Pro Tyr Arg Leu
        35                  40                  45

Ser His Ile Ser Phe Arg Gly Ser Asn Leu Thr Ile His Pro Leu Arg
    50                  55                  60

Asn Ile Arg Asp Ile Phe Tyr Val Gly Asn Ile Thr Ile Gly Thr Pro
65                  70                  75                  80

Pro Gln Glu Phe Gln Val Ile Phe Asp Thr Gly Ser Ser Asp Leu Trp
                85                  90                  95

Val Pro Ser Ile Asp Cys Asn Ser Thr Ser Cys Ala Thr His Val Arg
            100                 105                 110

Phe Arg His Leu Gln Ser Ser Thr Phe Arg Pro Thr Asn Lys Thr Phe
        115                 120                 125

Arg Ile Ile Tyr Gly Ser Gly Arg Met Asn Gly Val Ile Ala Tyr Asp
130                 135                 140

Thr Val Arg Ile Gly Asp Leu Val Ser Thr Asp Gln Pro Phe Gly Leu
145                 150                 155                 160

Ser Val Glu Glu Tyr Gly Phe Ala His Lys Arg Phe Asp Gly Ile Leu
                165                 170                 175

Gly Leu Asn Tyr Trp Asn Leu Ser Trp Ser Lys Ala Met Pro Ile Phe
            180                 185                 190

Asp Lys Leu Lys Asn Glu Gly Ala Ile Ser Glu Pro Val Phe Ala Phe
        195                 200                 205

Tyr Leu Ser Asn Ile Thr Met Asn Arg Glu Val Ile Ala Cys Ser Glu
    210                 215                 220
```

```
Gly Cys Ala Ala Leu Val Asp Thr Gly Ser Ser Asn Ile Gln Gly Pro
225                 230                 235                 240

Gly Arg Leu Ile Asp Asn Ile Gln Arg Ile Ile Gly Ala Thr Pro Arg
            245                 250                 255

Gly Ser Lys Tyr Tyr Val Ser Cys Ser Ala Val Asn Ile Leu Pro Ser
            260                 265                 270

Ile Ile Phe Thr Ile Asn Gly Val Asn Tyr Pro Val Pro Pro Arg Ala
        275                 280                 285

Tyr Ile Leu Lys Asp Ser Arg Gly His Cys Tyr Thr Thr Phe Lys Glu
    290                 295                 300

Lys Arg Val Arg Ser Thr Glu Ser Trp Val Leu Gly Glu Val Phe
305                 310                 315                 320

Leu Arg Leu Tyr Phe Ser Val Phe Asp Arg Gly Asn Asp Arg Ile Gly
                325                 330                 335

Leu Ala Arg Arg Val
            340

<210> SEQ ID NO 31
<211> LENGTH: 387
<212> TYPE: PRT
<213> ORGANISM: bovidae

<400> SEQUENCE: 31

Met Lys Trp Leu Val Leu Gly Leu Val Ala Leu Ser Glu Cys Ile
1               5                   10                  15

Val Lys Ile Pro Leu Thr Lys Met Lys Thr Met Gln Glu Ala Ile Arg
            20                  25                  30

Glu Lys Gln Leu Leu Glu Asp Phe Leu Asp Glu Gln Pro His Ser Leu
        35                  40                  45

Ser Gln His Ser Asp Pro Asp Lys Lys Phe Ser Ser His Gln Leu Lys
    50                  55                  60

Asn Phe Gln Asn Ala Val Tyr Phe Gly Thr Ile Thr Ile Gly Thr Pro
65                  70                  75                  80

Pro Gln Glu Phe Gln Val Asn Phe Asp Thr Gly Ser Ser Asp Leu Trp
                85                  90                  95

Val Pro Ser Val Asp Cys Gln Ser Pro Ser Cys Ser Lys His Lys Arg
            100                 105                 110

Phe Asp Pro Gln Lys Ser Thr Thr Phe Gln Pro Leu Asn Gln Lys Ile
        115                 120                 125

Glu Leu Val Tyr Gly Ser Gly Thr Met Lys Gly Val Leu Gly Ser Asp
    130                 135                 140

Thr Ile Gln Ile Gly Asn Leu Val Ile Val Asn Gln Ile Phe Gly Leu
145                 150                 155                 160

Ser Gln Asn Gln Ser Ser Gly Val Leu Glu Gln Val Pro Tyr Asp Gly
                165                 170                 175

Ile Leu Gly Leu Ala Tyr Pro Ser Leu Ala Ile Gln Gly Thr Thr Pro
            180                 185                 190

Val Phe Asp Asn Leu Lys Asn Arg Glu Val Ile Ser Glu Pro Val Phe
        195                 200                 205

Ala Phe Tyr Leu Ser Ser Arg Pro Glu Asn Ile Ser Thr Val Met Phe
    210                 215                 220

Gly Gly Val Asp His Thr Tyr His Lys Gly Lys Leu Gln Trp Ile Pro
225                 230                 235                 240

Val Thr Gln Ala Arg Phe Trp Gln Val Ala Met Ser Ser Met Thr Met
                245                 250                 255
```

```
Asn Gly Asn Val Val Gly Cys Ser Gln Gly Cys Gln Ala Val Val Asp
            260                 265                 270

Thr Gly Thr Ser Leu Leu Val Gly Pro Thr His Leu Val Thr Asp Ile
        275                 280                 285

Leu Lys Leu Ile Asn Pro Asn Pro Ile Leu Asn Asp Glu Gln Met Leu
    290                 295                 300

Ser Cys Asp Ala Ile Asn Ser Leu Pro Thr Leu Leu Thr Ile Asn
305                 310                 315                 320

Gly Ile Val Tyr Pro Val Pro Pro Asp Tyr Tyr Ile Gln Arg Phe Ser
                325                 330                 335

Glu Arg Ile Cys Phe Ile Ser Phe Gln Gly Thr Glu Ile Leu Lys
                340                 345                 350

Asn Leu Gly Thr Ser Glu Thr Trp Ile Leu Gly Asp Val Phe Leu Arg
            355                 360                 365

Leu Tyr Phe Ser Val Tyr Asp Arg Gly Asn Asn Arg Ile Gly Leu Ala
        370                 375                 380

Pro Ala Ala
385

<210> SEQ ID NO 32
<211> LENGTH: 379
<212> TYPE: PRT
<213> ORGANISM: bovidae

<400> SEQUENCE: 32

Met Lys Trp Ile Val Leu Leu Gly Leu Val Ala Phe Ser Glu Cys Ile
1               5                   10                  15

Val Lys Ile Pro Leu Arg Gln Val Lys Thr Met Arg Lys Thr Leu Ser
            20                  25                  30

Gly Lys Asn Met Leu Lys Asn Phe Leu Lys Glu His Pro Tyr Arg Leu
        35                  40                  45

Ser Gln Ile Ser Phe Arg Gly Ser Asn Leu Thr Ile His Pro Leu Arg
    50                  55                  60

Asn Ile Met Asn Leu Val Tyr Val Gly Asn Ile Thr Ile Gly Thr Pro
65                  70                  75                  80

Pro Gln Glu Phe Gln Val Val Phe Asp Thr Gly Ser Ser Asp Leu Trp
                85                  90                  95

Val Pro Ser Phe Cys Thr Met Pro Ala Cys Ser Ala Pro Val Trp Phe
            100                 105                 110

Arg Gln Leu Gln Ser Ser Thr Phe Gln Pro Thr Asn Lys Thr Phe Thr
        115                 120                 125

Ile Thr Tyr Gly Ser Gly Ser Met Lys Gly Phe Leu Ala Tyr Asp Thr
    130                 135                 140

Val Arg Ile Gly Asp Leu Val Ser Thr Asp Gln Pro Phe Gly Leu Ser
145                 150                 155                 160

Val Val Glu Tyr Gly Leu Glu Gly Arg Asn Tyr Asp Gly Val Leu Gly
                165                 170                 175

Leu Asn Tyr Pro Asn Ile Ser Phe Ser Gly Ala Ile Pro Ile Phe Asp
            180                 185                 190

Asn Leu Lys Asn Gln Gly Ala Ile Ser Glu Pro Val Phe Ala Phe Tyr
        195                 200                 205

Leu Ser Lys Asn Lys Gln Glu Gly Ser Val Val Met Phe Gly Gly Val
    210                 215                 220

Asp His Gln Tyr Tyr Lys Gly Glu Leu Asn Trp Ile Pro Leu Ile Glu
225                 230                 235                 240
```

-continued

```
Ala Gly Glu Trp Arg Val His Met Asp Arg Ile Ser Met Lys Arg Thr
                245                 250                 255

Val Ile Ala Cys Ser Asp Gly Cys Glu Ala Leu Val His Thr Gly Thr
            260                 265                 270

Ser His Ile Glu Gly Pro Gly Arg Leu Val Asn Asn Ile His Arg Leu
        275                 280                 285

Ile Arg Thr Arg Pro Phe Asp Ser Lys His Tyr Val Ser Cys Phe Ala
    290                 295                 300

Thr Lys Tyr Leu Pro Ser Ile Thr Phe Ile Ile Asn Gly Ile Lys Tyr
305                 310                 315                 320

Pro Met Thr Ala Arg Ala Tyr Ile Phe Lys Asp Ser Arg Gly Arg Cys
                325                 330                 335

Tyr Ser Ala Phe Lys Glu Asn Thr Val Arg Thr Ser Arg Glu Thr Trp
            340                 345                 350

Ile Leu Gly Asp Ala Phe Leu Arg Arg Tyr Phe Ser Val Phe Asp Arg
        355                 360                 365

Gly Asn Asp Arg Ile Gly Leu Ala Arg Ala Val
    370                 375
```

<210> SEQ ID NO 33
<211> LENGTH: 380
<212> TYPE: PRT
<213> ORGANISM: bovidae

<400> SEQUENCE: 33

```
Met Lys Trp Leu Gly Leu Leu Gly Leu Val Ala Leu Ser Glu Cys Met
  1               5                  10                  15

Val Ile Ile Pro Leu Arg Gln Met Lys Thr Met Arg Glu Thr Leu Arg
             20                  25                  30

Glu Arg His Leu Leu Thr Asn Phe Ser Glu Glu His Pro Tyr Asn Leu
         35                  40                  45

Ser Gln Lys Ala Ala Asn Asp Gln Asn Ile Ile Tyr His His Pro Leu
     50                  55                  60

Arg Ser Tyr Lys Asp Phe Ser Tyr Ile Gly Asn Ile Asn Ile Gly Thr
 65                  70                  75                  80

Pro Pro Gln Glu Phe Gln Val Leu Phe Asp Thr Gly Ser Ser Ser Leu
                 85                  90                  95

Trp Val Pro Ser Ile Tyr Cys Gln Ser Ser Ser Cys Tyr Lys His Asn
            100                 105                 110

Ser Phe Val Pro Cys Asn Ser Ser Thr Phe Lys Ala Thr Asn Lys Ile
        115                 120                 125

Phe Asn Thr Asn Tyr Thr Ala Thr Ser Ile Lys Gly Tyr Leu Val Tyr
    130                 135                 140

Asp Thr Val Arg Ile Gly Asn Leu Val Ser Val Ala Gln Pro Phe Gly
145                 150                 155                 160

Leu Ser Leu Lys Glu Phe Gly Phe Asp Val Pro Phe Asp Gly Ile
                165                 170                 175

Leu Gly Leu Gly Tyr Pro Arg Arg Thr Ile Thr Gly Ala Asn Pro Ile
            180                 185                 190

Phe Asp Asn Leu Trp Lys Gln Gly Val Ile Ser Glu Pro Val Phe Ala
        195                 200                 205

Phe Tyr Leu Ser Ser Gln Lys Glu Asn Gly Ser Val Val Met Phe Gly
    210                 215                 220

Gly Val Asn Arg Ala Tyr Tyr Lys Gly Glu Leu Asn Trp Val Pro Val
225                 230                 235                 240
```

```
Ser Gln Val Gly Ser Trp His Ile Asn Ile Asp Ser Ile Ser Met Asn
            245                 250                 255

Gly Thr Val Val Ala Cys Lys Arg Gly Cys Gln Ala Ser Trp Ile Arg
                260                 265                 270

Gly Arg Leu Ser Ala Trp Pro Lys Arg Ile Val Ser Lys Ile Gln Lys
            275                 280                 285

Leu Ile His Ala Arg Pro Ile Asp Arg Glu His Val Val Ser Cys Gln
        290                 295                 300

Ala Ile Gly Thr Leu Pro Pro Ala Val Phe Thr Ile Asn Gly Ile Asp
305                 310                 315                 320

Tyr Pro Val Pro Ala Gln Ala Tyr Ile Gln Ser Leu Ser Gly Tyr Cys
                325                 330                 335

Phe Ser Asn Phe Leu Val Arg Pro Gln Arg Val Asn Glu Ser Glu Thr
            340                 345                 350

Trp Ile Leu Gly Asp Val Phe Leu Arg Leu Tyr Phe Ser Val Phe Asp
        355                 360                 365

Arg Gly Asn Asn Arg Ile Gly Leu Ala Pro Ala Val
            370                 375                 380

<210> SEQ ID NO 34
<211> LENGTH: 376
<212> TYPE: PRT
<213> ORGANISM: bovidae

<400> SEQUENCE: 34

Met Lys Trp Leu Val Phe Leu Gly Leu Val Ala Phe Ser Glu Cys Ile
1               5                   10                  15

Val Ile Met Leu Leu Thr Lys Thr Lys Thr Met Arg Glu Ile Trp Arg
            20                  25                  30

Glu Lys Lys Leu Leu Asn Ser Phe Leu Glu Glu Gln Ala Asn Arg Met
        35                  40                  45

Ser Asp Asp Ser Ala Ser Pro Lys Leu Ser Thr His Pro Leu Arg
    50                  55                  60

Asn Ala Leu Asp Met Ala Tyr Val Gly Asn Ile Thr Ile Gly Thr Pro
65                  70                  75                  80

Pro Lys Glu Phe Arg Val Val Phe Asp Thr Gly Ser Ser Asp Leu Trp
                85                  90                  95

Val Pro Ser Ile Lys Cys Ile Ser Pro Ala Cys His Thr His Ile Thr
            100                 105                 110

Phe Asp His His Lys Ser Ser Thr Phe Arg Leu Thr Arg Pro Phe
        115                 120                 125

His Ile Leu Tyr Gly Ser Gly Met Met Asn Gly Val Leu Ala Tyr Asp
    130                 135                 140

Thr Val Arg Ile Gly Lys Leu Val Ser Thr Asp Gln Pro Phe Gly Leu
145                 150                 155                 160

Ser Leu Gln Gln Phe Gly Phe Asp Asn Ala Pro Phe Asp Gly Val Leu
                165                 170                 175

Gly Leu Ser Tyr Pro Ser Leu Ala Val Pro Gly Thr Ile Pro Ile Phe
            180                 185                 190

Asp Lys Leu Lys Gln Gln Gly Ala Ile Ser Glu Pro Ile Phe Ala Phe
        195                 200                 205

Tyr Leu Ser Thr Arg Lys Glu Asn Gly Ser Val Leu Met Leu Gly Gly
    210                 215                 220

Val Asp His Ser Tyr His Lys Gly Lys Leu Asn Trp Ile Pro Val Ser
225                 230                 235                 240
```

```
Gln Thr Lys Ser Trp Leu Ile Thr Val Asp Arg Ile Ser Met Asn Gly
            245                 250                 255

Arg Val Ile Gly Cys Glu His Gly Cys Glu Ala Leu Val Asp Thr Gly
            260                 265                 270

Thr Ser Leu Ile His Gly Pro Ala Arg Pro Val Thr Asn Ile Gln Lys
            275                 280                 285

Phe Ile His Ala Met Pro Tyr Gly Ser Glu Tyr Met Val Leu Cys Pro
            290                 295                 300

Val Ile Ser Ile Leu Pro Pro Val Ile Phe Thr Ile Asn Gly Ile Asp
305                 310                 315                 320

Tyr Ser Val Pro Arg Glu Ala Tyr Ile Gln Lys Ile Ser Asn Ser Leu
                325                 330                 335

Cys Leu Ser Thr Phe His Gly Asp Asp Thr Asp Gln Trp Ile Leu Gly
                340                 345                 350

Asp Val Phe Leu Arg Leu Tyr Phe Ser Val Tyr Asp Arg Gly Asn Asn
                355                 360                 365

Arg Ile Gly Leu Ala Pro Ala Val
                370                 375

<210> SEQ ID NO 35
<211> LENGTH: 375
<212> TYPE: PRT
<213> ORGANISM: bovidae

<400> SEQUENCE: 35

Met Lys Trp Leu Val Leu Gly Leu Val Ala Leu Ser Glu Cys Ile
1               5                   10                  15

Val Ile Leu Pro Leu Arg Lys Met Lys Thr Leu Arg Glu Thr Leu Arg
                20                  25                  30

Glu Lys Asn Leu Leu Asn Asn Phe Leu Glu Glu Arg Ala Tyr Arg Leu
            35                  40                  45

Ser Lys Lys Asp Ser Lys Ile Thr Ile His Pro Leu Lys Asn Tyr Leu
    50                  55                  60

Asp Met Ala Tyr Val Gly Asn Ile Thr Ile Gly Thr Pro Pro Gln Glu
65                  70                  75                  80

Phe Arg Val Val Phe Asp Thr Gly Ser Ala Asp Leu Trp Val Pro Ser
                85                  90                  95

Ile Ser Cys Val Ser Pro Ala Cys Tyr Thr His Lys Thr Phe Asn Leu
                100                 105                 110

His Asn Ser Ser Ser Phe Gly Gln Thr His Gln Pro Ile Ser Ile Ser
            115                 120                 125

Tyr Gly Pro Gly Ile Ile Gln Gly Phe Leu Gly Ser Asp Thr Val Arg
    130                 135                 140

Ile Gly Asn Leu Val Ser Leu Lys Gln Ser Phe Gly Leu Ser Gln Glu
145                 150                 155                 160

Glu Tyr Gly Phe Asp Gly Ala Pro Phe Asp Gly Val Leu Gly Leu Ala
                165                 170                 175

Tyr Pro Ser Ile Ser Ile Lys Gly Ile Ile Pro Ile Phe Asp Asn Leu
                180                 185                 190

Trp Ser Gln Gly Ala Phe Ser Glu Pro Val Phe Ala Phe Tyr Leu Asn
            195                 200                 205

Thr Cys Gln Pro Glu Gly Ser Val Val Met Phe Gly Gly Val Asp His
    210                 215                 220

Arg Tyr Tyr Lys Gly Glu Leu Asn Trp Ile Pro Val Ser Gln Thr Arg
225                 230                 235                 240
```

Tyr Trp Gln Ile Ser Met Asn Arg Ile Ser Met Asn Gly Asn Val Thr
                245                 250                 255

Ala Cys Ser Arg Gly Cys Gln Ala Leu Leu Asp Thr Gly Thr Ser Met
            260                 265                 270

Ile His Gly Pro Thr Arg Leu Ile Thr Asn Ile His Lys Leu Met Asn
        275                 280                 285

Ala Arg His Gln Gly Ser Glu Tyr Val Val Ser Cys Asp Ala Val Lys
    290                 295                 300

Thr Leu Pro Pro Val Ile Phe Asn Ile Asn Gly Ile Asp Tyr Pro Leu
305                 310                 315                 320

Pro Pro Gln Ala Tyr Ile Thr Lys Ala Gln Asn Phe Cys Leu Ser Ile
                325                 330                 335

Phe His Gly Gly Thr Glu Thr Ser Ser Pro Glu Thr Trp Ile Leu Gly
            340                 345                 350

Gly Val Phe Leu Arg Gln Tyr Phe Ser Val Phe Asp Arg Arg Asn Asp
        355                 360                 365

Ser Ile Gly Leu Ala Gln Val
    370                 375

<210> SEQ ID NO 36
<211> LENGTH: 391
<212> TYPE: PRT
<213> ORGANISM: bovidae

<400> SEQUENCE: 36

Met Lys Trp Leu Val Leu Gly Leu Val Ala Leu Ser Glu Cys Ile
1               5                   10                  15

Val Ile Leu Pro Leu Lys Lys Met Lys Thr Leu Arg Glu Thr Leu Arg
            20                  25                  30

Glu Lys Asn Leu Leu Asn Asn Phe Leu Glu Glu Gln Ala Tyr Arg Leu
        35                  40                  45

Ser Lys Asn Asp Ser Lys Ile Thr Ile His Pro Leu Arg Asn Tyr Leu
    50                  55                  60

Asp Thr Ala Tyr Val Gly Asn Ile Thr Ile Gly Thr Pro Pro Gln Glu
65                  70                  75                  80

Phe Arg Val Val Phe Asp Thr Gly Ser Ala Asn Leu Trp Val Pro Cys
                85                  90                  95

Ile Thr Cys Thr Ser Pro Ala Cys Tyr Thr His Lys Thr Phe Asn Pro
            100                 105                 110

Gln Asn Ser Ser Ser Phe Arg Glu Val Gly Ser Pro Ile Thr Ile Phe
        115                 120                 125

Tyr Gly Ser Gly Ile Ile Gln Gly Phe Leu Gly Ser Asp Thr Val Arg
    130                 135                 140

Ile Gly Asn Leu Val Ser Leu Lys Gln Ser Phe Gly Leu Ser Gln Glu
145                 150                 155                 160

Glu Tyr Gly Phe Asp Gly Ala Pro Phe Asp Gly Val Leu Gly Leu Ala
                165                 170                 175

Tyr Pro Ser Ile Ser Ile Lys Gly Ile Ile Pro Ile Phe Asp Asn Leu
            180                 185                 190

Trp Ser His Gly Ala Phe Ser Glu Pro Val Phe Ala Phe Tyr Leu Asn
        195                 200                 205

Thr Asn Lys Pro Glu Gly Ser Val Val Met Phe Gly Val Asp His
    210                 215                 220

Arg Tyr Tyr Lys Gly Glu Leu Asn Trp Ile Pro Val Ser Gln Thr Ser
225                 230                 235                 240

```
His Trp Gln Ile Ser Met Asn Asn Ile Ser Met Asn Gly Thr Val Thr
                245                 250                 255

Ala Cys Ser Cys Gly Cys Glu Ala Leu Leu Asp Thr Gly Thr Ser Met
                260                 265                 270

Ile Tyr Gly Pro Thr Lys Leu Val Thr Asn Ile His Lys Leu Met Asn
                275                 280                 285

Ala Arg Leu Glu Asn Ser Glu Tyr Val Val Ser Cys Asp Ala Val Lys
                290                 295                 300

Thr Leu Pro Pro Val Ile Phe Asn Ile Asn Gly Ile Asp Tyr Pro Leu
305                 310                 315                 320

Arg Pro Gln Ala Tyr Ile Ile Lys Ile Gln Asn Asn Cys Arg Ser Val
                    325                 330                 335

Phe Gln Gly Gly Thr Glu Asn Ser Ser Leu Asn Thr Trp Ile Leu Gly
                340                 345                 350

Asp Ile Phe Leu Arg Gln Tyr Phe Ser Val Phe Asp Arg Lys Asn Arg
                355                 360                 365

Arg Ile Cys Trp His Arg Trp Val Pro Thr Thr Arg Thr Thr Met Thr
                370                 375                 380

Ser Lys Leu Pro Pro Lys Leu
385                 390

<210> SEQ ID NO 37
<211> LENGTH: 392
<212> TYPE: PRT
<213> ORGANISM: bovidae

<400> SEQUENCE: 37

Met Lys Trp Leu Val Leu Leu Ala Leu Val Ala Phe Ser Glu Cys Ile
1               5                   10                  15

Ile Lys Ile Pro Leu Arg Arg Val Lys Thr Met Ser Asn Thr Ala Ser
                20                  25                  30

Gly Lys Asn Met Leu Asn Asn Phe Leu Lys Lys His Pro Tyr Arg Leu
            35                  40                  45

Ser Gln Ile Ser Phe Arg Gly Ser Asn Leu Thr Thr His Pro Leu Met
        50                  55                  60

Asn Ile Trp Asp Leu Leu Tyr Leu Gly Asn Ile Thr Ile Gly Thr Pro
65                  70                  75                  80

Pro Gln Glu Phe Gln Val Leu Phe Asp Thr Gly Ser Ser Asp Leu Trp
                85                  90                  95

Val Pro Ser Leu Leu Cys Asn Ser Ser Thr Cys Ala Lys His Val Met
                100                 105                 110

Phe Arg His Arg Leu Ser Ser Thr Tyr Arg Pro Thr Asn Lys Thr Phe
            115                 120                 125

Met Ile Phe Tyr Ala Val Gly Lys Ile Glu Gly Val Val Arg Asp
        130                 135                 140

Thr Val Arg Ile Gly Asp Leu Val Ser Ala Asp Gln Thr Phe Gly Leu
145                 150                 155                 160

Ser Ile Ala Glu Thr Gly Phe Glu Asn Thr Thr Leu Asp Gly Ile Leu
                165                 170                 175

Gly Leu Ser Tyr Pro Asn Thr Ser Cys Phe Gly Thr Ile Pro Ile Phe
                180                 185                 190

Asp Lys Leu Lys Asn Glu Gly Ala Ile Ser Glu Pro Val Leu His Ser
            195                 200                 205

Val Arg Arg Lys Asp Glu Gln Glu Gly Ser Val Val Met Phe Gly Gly
210                 215                 220
```

```
Val Asp His Ser Tyr Tyr Lys Gly Glu Leu Asn Trp Val Pro Leu Ile
225                 230                 235                 240

Lys Ala Gly Asp Trp Ser Val Arg Val Asp Ser Ile Thr Met Lys Arg
            245                 250                 255

Glu Val Ile Ala Cys Ser Asp Gly Cys Arg Ala Leu Val Asp Thr Gly
        260                 265                 270

Ser Ser His Ile Gln Gly Pro Gly Arg Leu Ile Asp Asn Val Gln Lys
    275                 280                 285

Leu Ile Gly Thr Met Pro Gln Gly Ser Met His Tyr Val Pro Cys Ser
290                 295                 300

Ala Val Asn Thr Leu Pro Ser Ile Ile Phe Thr Ile Asn Ser Ile Ser
305                 310                 315                 320

Tyr Thr Val Pro Ala Gln Ala Tyr Ile Leu Lys Gly Ser Arg Gly Arg
                325                 330                 335

Cys Tyr Ser Thr Phe Gln Gly His Thr Met Ser Ser Thr Glu Thr
            340                 345                 350

Trp Ile Leu Gly Asp Val Phe Leu Ser Gln Tyr Phe Ser Val Phe Asp
        355                 360                 365

Arg Gly Asn Asp Arg Ile Gly Leu Ala Gln Val Gly Thr Asp Tyr Lys
    370                 375                 380

Asp Asp Asp Glu Ser Pro Lys Leu
385                 390

<210> SEQ ID NO 38
<211> LENGTH: 388
<212> TYPE: PRT
<213> ORGANISM: Felis domestica

<400> SEQUENCE: 38

Met Lys Trp Leu Trp Val Leu Gly Leu Val Ala Leu Ser Glu Cys Leu
1               5                   10                  15

Val Thr Ile Pro Leu Thr Arg Val Lys Ser Met Arg Glu Asn Leu Arg
            20                  25                  30

Glu Lys Asp Arg Leu Lys Asp Phe Leu Glu Asn His Pro Tyr Asn Leu
        35                  40                  45

Ala Tyr Lys Phe Val Asp Ser Val Asn Leu Asp Leu Gly Ile Tyr Phe
    50                  55                  60

Glu Pro Met Arg Asn Tyr Leu Asp Leu Ala Tyr Val Gly Thr Ile Ser
65                  70                  75                  80

Ile Gly Thr Pro Pro Gln Glu Phe Lys Val Ile Phe Asp Thr Gly Ser
                85                  90                  95

Ser Asp Leu Trp Val Pro Ser Ile Tyr Cys Ser Ser Pro Ala Cys Ala
            100                 105                 110

Asn His Asn Val Phe Asn Pro Leu Arg Ser Ser Thr Phe Arg Ile Ser
        115                 120                 125

Gly Arg Pro Ile His Leu Gln Tyr Gly Ser Gly Thr Met Ser Gly Phe
    130                 135                 140

Leu Ala Tyr Asp Thr Val Arg Phe Gly Gly Leu Val Asp Val Ala Gln
145                 150                 155                 160

Ala Phe Gly Leu Ser Leu Arg Glu Pro Gly Lys Phe Met Glu Tyr Ala
                165                 170                 175

Val Phe Asp Gly Ile Leu Gly Leu Ala Tyr Pro Ser Leu Ser Leu Arg
            180                 185                 190

Gly Thr Val Pro Val Phe Asp Asn Leu Trp Lys Gln Gly Leu Ile Ser
        195                 200                 205
```

```
Gln Glu Leu Phe Ala Phe Tyr Leu Ser Lys Lys Asp Glu Glu Gly Ser
        210                 215                 220

Val Val Met Phe Gly Gly Val Asp His Ser Tyr Tyr Ser Gly Asp Leu
225                 230                 235                 240

Asn Trp Val Pro Val Ser Lys Arg Leu Tyr Trp Gln Leu Ser Met Asp
                245                 250                 255

Ser Ile Ser Met Asn Gly Glu Val Ile Ala Cys Asp Gly Gly Cys Gln
            260                 265                 270

Ala Ile Ile Asp Thr Gly Thr Ser Leu Leu Ile Gly Pro Ser His Val
        275                 280                 285

Val Phe Asn Ile Gln Met Ile Ile Gly Ala Asn Gln Ser Tyr Ser Gly
    290                 295                 300

Glu Tyr Val Val Asp Cys Asp Ala Ala Asn Thr Leu Pro Asp Ile Val
305                 310                 315                 320

Phe Thr Ile Asn Gly Ile Asp Tyr Pro Val Pro Ala Ser Ala Tyr Ile
                325                 330                 335

Gln Glu Gly Pro Gln Gly Thr Cys Tyr Ser Gly Phe Asp Glu Ser Gly
            340                 345                 350

Asp Ser Leu Leu Val Ser Asp Ser Trp Ile Leu Gly Asp Val Phe Leu
        355                 360                 365

Arg Leu Tyr Phe Thr Val Phe Asp Arg Glu Asn Asn Arg Ile Gly Leu
    370                 375                 380

Ala Leu Ala Val
385

<210> SEQ ID NO 39
<211> LENGTH: 1158
<212> TYPE: DNA
<213> ORGANISM: bovidae

<400> SEQUENCE: 39
aggaaagaag catgaagtgg cttgtggtcc tcgggctggt ggccttctca gagtgcatag      60
tcaaatacc tctaaggaga gtgaagacca tgagaaaaac tctcagtgga aaaaacatgc     120
tgaacaattt cttgaaggag gatccttaca gactgtccca gatttctttt cgtggctcaa     180
atctaactat tcacccgctg agaaacatca gagatatctt ctatgtcgga acatcacca     240
ttggaacacc ccctcaggaa ttccaggtta tctttgacac aggctcatct gacttgtggg     300
tgccctcgat cgattgcaac agtacatcct gtgctacaca tgttaggttc agacatcttc     360
agtcttccac cttccggcct accaataaga ccttcaggat catctatgga tctgggagaa     420
tgaacggagt tattgcttat gacacagttc ggattgggga ccttgtaagt accgaccagc     480
catttggtct aagcgtggag gaatatgggt ttgcgcacaa agatttgat ggcatcttgg     540
gcttgaacta ctggaaccta tcctggtcta aggccatgcc catctttgac aagctgaaga     600
atgaaggcgc catttctgag cctgtttttg ccttctactt gagcaaagac aagcgggagg     660
gcagtgtggt gatgtttggt ggggtggacc accgctacta caagggagag ctcaagtggg     720
taccactgat ccaagcagtc gactggagtg tacacgtaga ccgcatcacc atgaacagag     780
aggttattgc ttgttctgaa ggctgtgcgg cccttgtgga cactgggtca tcaaatatcc     840
aaggcccaag aagactgatt gataacatac agaggatcat cggcgccacg ccacgggtt     900
ccaagtacta cgtttcatgt tctgcggtca atatcctgcc ctctattatc ttcaccatca     960
acggcgtcaa ctacccagtg ccactcgag cttacatcct caaggattct agaggccact    1020
gctataccac ctttaaagag aaaagagtga ggagatctac agagagctgg gtcctgggtg    1080
```

```
aagtcttcct gaggctgtat ttctcagtct ttgatcgagg aaatgacagg attggcctgg   1140
cacgggcagt gtaactcg                                                  1158
```

<210> SEQ ID NO 40
<211> LENGTH: 380
<212> TYPE: PRT
<213> ORGANISM: bovidae

<400> SEQUENCE: 40

```
Met Lys Trp Leu Val Val Leu Gly Leu Val Ala Phe Ser Glu Cys Ile
 1               5                  10                  15

Val Lys Ile Pro Leu Arg Arg Val Lys Thr Met Arg Lys Thr Leu Ser
             20                  25                  30

Gly Lys Asn Met Leu Asn Asn Phe Leu Lys Glu Asp Pro Tyr Arg Leu
         35                  40                  45

Ser Gln Ile Ser Phe Arg Gly Ser Asn Leu Thr Ile His Pro Leu Arg
     50                  55                  60

Asn Ile Arg Asp Ile Phe Tyr Val Gly Asn Ile Thr Ile Gly Thr Pro
 65                  70                  75                  80

Pro Gln Glu Phe Gln Val Ile Phe Asp Thr Gly Ser Ser Asp Leu Trp
                 85                  90                  95

Val Pro Ser Ile Asp Cys Asn Ser Thr Ser Cys Ala Thr His Val Arg
            100                 105                 110

Phe Arg His Leu Gln Ser Ser Thr Phe Arg Pro Thr Asn Lys Thr Phe
        115                 120                 125

Arg Ile Ile Tyr Gly Ser Gly Arg Met Asn Gly Val Ile Ala Tyr Asp
    130                 135                 140

Thr Val Arg Ile Gly Asp Leu Val Ser Thr Asp Gln Pro Phe Gly Leu
145                 150                 155                 160

Ser Val Glu Glu Tyr Gly Phe Ala His Lys Arg Phe Asp Gly Ile Leu
                165                 170                 175

Gly Leu Asn Tyr Trp Asn Leu Ser Trp Ser Lys Ala Met Pro Ile Phe
            180                 185                 190

Asp Lys Leu Lys Asn Glu Gly Ala Ile Ser Glu Pro Val Phe Ala Phe
        195                 200                 205

Tyr Leu Ser Lys Asp Lys Arg Glu Gly Ser Val Val Met Phe Gly Gly
    210                 215                 220

Val Asp His Arg Tyr Tyr Lys Gly Glu Leu Lys Trp Val Pro Leu Ile
225                 230                 235                 240

Gln Ala Val Asp Trp Ser Val His Val Asp Arg Ile Thr Met Asn Arg
                245                 250                 255

Glu Val Ile Ala Cys Ser Glu Gly Cys Ala Ala Leu Val Asp Thr Gly
            260                 265                 270

Ser Ser Asn Ile Gln Gly Pro Arg Arg Leu Ile Asp Asn Ile Gln Arg
        275                 280                 285

Ile Ile Gly Ala Thr Pro Arg Gly Ser Lys Tyr Tyr Val Ser Cys Ser
    290                 295                 300

Ala Val Asn Ile Leu Pro Ser Ile Ile Phe Thr Ile Asn Gly Val Asn
305                 310                 315                 320

Tyr Pro Val Pro Pro Arg Ala Tyr Ile Leu Lys Asp Ser Arg Gly His
                325                 330                 335

Cys Tyr Thr Thr Phe Lys Glu Lys Arg Val Arg Arg Ser Thr Glu Ser
            340                 345                 350
```

```
Trp Val Leu Gly Glu Val Phe Leu Arg Leu Tyr Phe Ser Val Phe Asp
        355                 360                 365
Arg Gly Asn Asp Arg Ile Gly Leu Ala Arg Ala Val
    370                 375                 380
```

<210> SEQ ID NO 41
<211> LENGTH: 1155
<212> TYPE: DNA
<213> ORGANISM: bovidae

<400> SEQUENCE: 41

```
aggaaagaag catgaagtgg attgtgctcc tcgggctgat ggccttctca gagtgcatag      60
tccaaatacc tctaaggcaa gtgaagacca tgagaaaaac cctcagtgga aaaaacatgc    120
tgaagaattt cttgaaggag catccttaca gactgtccca gatttctttt cgtggctcaa    180
atctaactat tcacccgctg aggaacatca tgaatttggt ctacgtgggt aacatcacca    240
ttggaacacc ccctcaggaa ttccaggttg tctttgacac aggctcatct gacttgtggg    300
tgccctcctt tgtaccatg ccagcatgct ctgcaccggt ttggttcaga caacttcagt     360
cttccacctt ccagcctacc aataagacct tcaccatcac ctatggatct gggagcatga    420
agggatttct tgcttatgac acagttcgga ttggggacct tgtaagtact gatcagccgt    480
tcggtctaag cgtggtggaa tatggggttgg agggcagaaa ttatgatggt gccttgggct   540
tgaactaccc caacatatcc ttctctggag ccatccccat cttttgacaac ctgaagaatc   600
aaggtgccat ttctgagcct gttttttgcct tctacttgag caaaaacaag caggagggca   660
gtgtggtgat gtttggtggg gtggaccacc agtactacaa gggagagctc aactggatac   720
cactgattga agcaggcgaa tggagagtac acatggaccg catctccatg aaaagaacgg   780
ttattgcttg ttctgatggc tgtgaggccc ttgtgcacac tgggacatca catatcgaag   840
gcccaggaag actggtgaat aacatacaca ggctcatccg caccaggcca tttgattcca   900
agcactacgt ttcatgtttt gccaccaata ccctgccctc tattactttc atcatcaacg   960
gcatcaagta cccaatgaca gctcgagcct acatctttaa ggattctaga ggccgctgct  1020
attccgcttt taagagaac acagtgagaa catctagaga gacctggatc ctcggtgatg  1080
ccttcctgag gcggtatttc tcagtctttg atcgaggaaa tgacaggatt ggcctggcac  1140
gggcagtgta actcg                                                   1155
```

<210> SEQ ID NO 42
<211> LENGTH: 379
<212> TYPE: PRT
<213> ORGANISM: bovidae

<400> SEQUENCE: 42

```
Met Lys Trp Ile Val Leu Leu Gly Leu Met Ala Phe Ser Glu Cys Ile
  1               5                  10                  15
Val Gln Ile Pro Leu Arg Gln Val Lys Thr Met Arg Lys Thr Leu Ser
             20                  25                  30
Gly Lys Asn Met Leu Lys Asn Phe Leu Lys Glu His Pro Tyr Arg Leu
         35                  40                  45
Ser Gln Ile Ser Phe Arg Gly Ser Asn Leu Thr Ile His Pro Leu Arg
     50                  55                  60
Asn Ile Met Asn Leu Val Tyr Val Gly Asn Ile Thr Ile Gly Thr Pro
 65                  70                  75                  80
Pro Gln Glu Phe Gln Val Val Phe Asp Thr Gly Ser Ser Asp Leu Trp
                 85                  90                  95
```

```
Val Pro Ser Phe Cys Thr Met Pro Ala Cys Ser Ala Pro Val Trp Phe
                100                 105                 110
Arg Gln Leu Gln Ser Ser Thr Phe Gln Pro Thr Asn Lys Thr Phe Thr
            115                 120                 125
Ile Thr Tyr Gly Ser Gly Ser Met Lys Gly Phe Leu Ala Tyr Asp Thr
        130                 135                 140
Val Arg Ile Gly Asp Leu Val Ser Thr Asp Gln Pro Phe Gly Leu Ser
145                 150                 155                 160
Val Val Glu Tyr Gly Leu Glu Gly Arg Asn Tyr Asp Gly Ala Leu Gly
                165                 170                 175
Leu Asn Tyr Pro Asn Ile Ser Phe Ser Gly Ala Ile Pro Ile Phe Asp
            180                 185                 190
Asn Leu Lys Asn Gln Gly Ala Ile Ser Glu Pro Val Phe Ala Phe Tyr
        195                 200                 205
Leu Ser Lys Asn Lys Gln Glu Gly Ser Val Val Met Phe Gly Gly Val
    210                 215                 220
Asp His Gln Tyr Tyr Lys Gly Glu Leu Asn Trp Ile Pro Leu Ile Glu
225                 230                 235                 240
Ala Gly Glu Trp Arg Val His Met Asp Arg Ile Ser Met Lys Arg Thr
                245                 250                 255
Val Ile Ala Cys Ser Asp Gly Cys Glu Ala Leu Val His Thr Gly Thr
            260                 265                 270
Ser His Ile Glu Gly Pro Gly Arg Leu Val Asn Asn Ile His Arg Leu
        275                 280                 285
Ile Arg Thr Arg Pro Phe Asp Ser Lys His Tyr Val Ser Cys Phe Ala
    290                 295                 300
Thr Asn Thr Leu Pro Ser Ile Thr Phe Ile Ile Asn Gly Ile Lys Tyr
305                 310                 315                 320
Pro Met Thr Ala Arg Ala Tyr Ile Phe Lys Asp Ser Arg Gly Arg Cys
                325                 330                 335
Tyr Ser Ala Phe Lys Glu Asn Thr Val Arg Thr Ser Arg Glu Thr Trp
            340                 345                 350
Ile Leu Gly Asp Ala Phe Leu Arg Arg Tyr Phe Ser Val Phe Asp Arg
        355                 360                 365
Gly Asn Asp Arg Ile Gly Leu Ala Arg Ala Val
    370                 375

<210> SEQ ID NO 43
<211> LENGTH: 1154
<212> TYPE: DNA
<213> ORGANISM: bovidae

<400> SEQUENCE: 43
aggaaagaag catgaagtgg cttgtgctcc tagggctggt ggccttctca gagtgcgtag      60
tcaaatacc tctaaggaga gtgaagacca tgacaaaaac cctcagtggg aaaaacatgc     120
tgaacaattt cctgaaggag catgcttaca gactgtccca gatttctttt catggctcaa     180
atctaactat tcaccgctg agaaacatca gggatttgtt ctacatgggt aacatcacca     240
ttggaacacc ccctcaggaa ttcctggttg tctttgacac aggctcatct gacttgtggg     300
ttccctccga cttttgcacc agtccagcct gttctaaaca ctttaggttc agacatcttc     360
agtcttccac attccggctt accaataaga ccttcagcat gaatacgga tctgggacaa     420
tggaaggaat gttgctcat gacacagttc ggattgggga ccttgtaagc actgaccagc     480
cgtttggtct aagcatgaca gaatccgggt ttgagggtat acctttgat ggcgtcttgg     540
```

-continued

```
gcttgaacta ccccaacata tccttctctg gagccatccc catctttgac aagctgaaga    600
atcaaggtgc catttctgag cctgtttttg ccttctattt gagcaaagac gagcaggagg    660
gcagtgtggt gatgtttggt ggggtggacc accgctacta caaggagag ctcaaatggg     720 taccattgat tgaagcgggt gactggattg tacacatgga ctgcatctcc atgagaagaa    780
aggttattgc ttgttctggc ggctgtgagg ccgttgttga caccgggta tcaatgatca     840 aaggcccaaa aacactggtt gataacatcc agaagctcat cggtgccact ctacggggtt    900
tcaagcacta cgtttcatgt tctgcagtcg ataccctgcc ctctattacc ttcaccataa    960
acggtatcaa ctaccgagtg ccagctcgag cctacatcct caaggattct agaggctgct   1020
gctatagcag ctttcaagag accactgtga gtccatctac agagacctgg atcctgggtg   1080
acgtcttcct gagactgtat ttctcagtct tgatcgagg aaatgacagg attgggctgg    1140
cacgggcagt gtaa                                                     1154
```

<210> SEQ ID NO 44
<211> LENGTH: 380
<212> TYPE: PRT
<213> ORGANISM: bovidae

<400> SEQUENCE: 44

```
Met Lys Trp Leu Val Leu Leu Gly Leu Val Ala Phe Ser Glu Cys Val
 1               5                  10                  15

Val Lys Ile Pro Leu Arg Arg Val Lys Thr Met Thr Lys Thr Leu Ser
             20                  25                  30

Gly Lys Asn Met Leu Asn Asn Phe Leu Lys Glu His Ala Tyr Arg Leu
         35                  40                  45

Ser Gln Ile Ser Phe His Gly Ser Asn Leu Thr Ile His Pro Leu Arg
     50                  55                  60

Asn Ile Arg Asp Leu Phe Tyr Met Gly Asn Ile Thr Ile Gly Thr Pro
 65                  70                  75                  80

Pro Gln Glu Phe Leu Val Val Phe Asp Thr Gly Ser Ser Asp Leu Trp
                 85                  90                  95

Val Pro Ser Asp Phe Cys Thr Ser Pro Ala Cys Ser Lys His Phe Arg
            100                 105                 110

Phe Arg His Leu Gln Ser Ser Thr Phe Arg Leu Thr Asn Lys Thr Phe
        115                 120                 125

Ser Ile Glu Tyr Gly Ser Gly Thr Met Glu Gly Ile Val Ala His Asp
    130                 135                 140

Thr Val Arg Ile Gly Asp Leu Val Ser Thr Asp Gln Pro Phe Gly Leu
145                 150                 155                 160

Ser Met Thr Glu Ser Gly Phe Glu Gly Ile Pro Phe Asp Gly Val Leu
                165                 170                 175

Gly Leu Asn Tyr Pro Asn Ile Ser Phe Ser Gly Ala Ile Pro Ile Phe
            180                 185                 190

Asp Lys Leu Lys Asn Gln Gly Ala Ile Ser Glu Pro Val Phe Ala Phe
        195                 200                 205

Tyr Leu Ser Lys Asp Glu Gln Glu Gly Ser Val Val Met Phe Gly Gly
    210                 215                 220

Val Asp His Arg Tyr Tyr Lys Gly Glu Leu Lys Trp Val Pro Leu Ile
225                 230                 235                 240

Glu Ala Gly Asp Trp Ile Val His Met Asp Cys Ile Ser Met Arg Arg
                245                 250                 255
```

```
Lys Val Ile Ala Cys Ser Gly Cys Glu Ala Val Val Asp Thr Gly
            260                 265                 270

Val Ser Met Ile Lys Gly Pro Lys Thr Leu Val Asp Asn Ile Gln Lys
        275                 280                 285

Leu Ile Gly Ala Thr Leu Arg Gly Phe Lys His Tyr Val Ser Cys Ser
        290                 295                 300

Ala Val Asp Thr Leu Pro Ser Ile Thr Phe Thr Ile Asn Gly Ile Asn
305                 310                 315                 320

Tyr Arg Val Pro Ala Arg Ala Tyr Ile Leu Lys Asp Ser Arg Gly Cys
                325                 330                 335

Cys Tyr Ser Ser Phe Gln Glu Thr Thr Val Ser Pro Ser Thr Glu Thr
                340                 345                 350

Trp Ile Leu Gly Asp Val Phe Leu Arg Leu Tyr Phe Ser Val Phe Asp
            355                 360                 365

Arg Gly Asn Asp Arg Ile Gly Leu Ala Arg Ala Val
        370                 375                 380

<210> SEQ ID NO 45
<211> LENGTH: 1168
<212> TYPE: DNA
<213> ORGANISM: bovidae

<400> SEQUENCE: 45
aggaaagaag catgaagtgg cttgtgctcc tcgggctggt ggccttctca gagtgcatag     60 tcaaatacc tctaaggaga gtgaagacca tgagaaaaac cctcagtgga aaaaacacgc    120
tgaacaattt cttgaaggag catccttaca gactgtccca tatttctttt cgtggctcaa    180
atctaactac tctgccgctg agaaacatca gagatatgct ctacgtgggt aacatcacca    240
ttggaacacc ccctcaagaa ttccaggttg tctttgacac aggttcatct gacttgtggg    300
tgccctctga cttttgcacc agtccagcct gttctacaca cgttaggttc agacattttc    360
agtcttccac cttccggcct accactaaga ccttcaggat catctatgga tctgggagaa    420
tgaaaggagt tgttgcgcat gacacagttc ggattgggaa ccttgtaagt actgaccagc    480
cgttcggcct aagcatggcg aatacgggt tggagagcag aagatttgat ggcatcttgg    540
gcttgaacta ccccaatcta tcctgctctg ggccattcc catctttgat aagctgaaga    600
atcaaggtgc catttctgat cctattttg ccttctactt gagcaaagac aagcgagagg    660
gcagtgtggt gatgtttggt ggggtggacc accgctacta caagggagag ctcaactggg    720
taccactgat tcgagcaggt gactggattg tacacgtaga ccgcatcacc atgaaaagag    780
aggttattgc ttgttctgat ggctgcgcgg cccttgtgga cactgggaca tcacttatcc    840
aaggcccagg aagagtgatc gataacatac acaagctcat tggtgccacg ccacggggtt    900
ccaagcatta cgtttcatgt tctgtggtca atactctgcc ctctattatc ttcaccatca    960
atggcatcaa ctacccagtg ccagctccag cctacatcct caaggattct agaggctact   1020
gctataccgc ctttaaagag caaagagtga ggagatctac agagagctgg ttactgggtg   1080
acgtcttcct gaggctgtat ttctcagtct ttgatcgagg aaatgacagg attggcctgg   1140
cacgggcagt gtaactcgaa tcactagt                                       1168

<210> SEQ ID NO 46
<211> LENGTH: 380
<212> TYPE: PRT
<213> ORGANISM: bovidae
```

<400> SEQUENCE: 46

```
Met Lys Trp Leu Val Leu Leu Gly Leu Val Ala Phe Ser Glu Cys Ile
  1               5                  10                  15
Val Lys Ile Pro Leu Arg Arg Val Lys Thr Met Arg Lys Thr Leu Ser
             20                  25                  30
Gly Lys Asn Thr Leu Asn Asn Phe Leu Lys Glu His Pro Tyr Arg Leu
         35                  40                  45
Ser His Ile Ser Phe Arg Gly Ser Asn Leu Thr Thr Leu Pro Leu Arg
     50                  55                  60
Asn Ile Arg Asp Met Leu Tyr Val Gly Asn Ile Thr Ile Gly Thr Pro
 65                  70                  75                  80
Pro Gln Glu Phe Gln Val Val Phe Asp Thr Gly Ser Ser Asp Leu Trp
                 85                  90                  95
Val Pro Ser Asp Phe Cys Thr Ser Pro Ala Cys Ser Thr His Val Arg
            100                 105                 110
Phe Arg His Phe Gln Ser Ser Thr Phe Arg Pro Thr Thr Lys Thr Phe
            115                 120                 125
Arg Ile Ile Tyr Gly Ser Gly Arg Met Lys Gly Val Val Ala His Asp
130                 135                 140
Thr Val Arg Ile Gly Asn Leu Val Ser Thr Asp Gln Pro Phe Gly Leu
145                 150                 155                 160
Ser Met Ala Glu Tyr Gly Leu Glu Ser Arg Arg Phe Asp Gly Ile Leu
                165                 170                 175
Gly Leu Asn Tyr Pro Asn Leu Ser Cys Ser Gly Ala Ile Pro Ile Phe
            180                 185                 190
Asp Lys Leu Lys Asn Gln Gly Ala Ile Ser Asp Pro Ile Phe Ala Phe
            195                 200                 205
Tyr Leu Ser Lys Asp Lys Arg Glu Gly Ser Val Val Met Phe Gly Gly
    210                 215                 220
Val Asp His Arg Tyr Tyr Lys Gly Glu Leu Asn Trp Val Pro Leu Ile
225                 230                 235                 240
Arg Ala Gly Asp Trp Ile Val His Val Asp Arg Ile Thr Met Lys Arg
                245                 250                 255
Glu Val Ile Ala Cys Ser Asp Gly Cys Ala Ala Leu Val Asp Thr Gly
            260                 265                 270
Thr Ser Leu Ile Gln Gly Pro Gly Arg Val Ile Asp Asn Ile His Lys
        275                 280                 285
Leu Ile Gly Ala Thr Pro Arg Gly Ser Lys His Tyr Val Ser Cys Ser
    290                 295                 300
Val Val Asn Thr Leu Pro Ser Ile Ile Phe Thr Ile Asn Gly Ile Asn
305                 310                 315                 320
Tyr Pro Val Pro Ala Pro Ala Tyr Ile Leu Lys Asp Ser Arg Gly Tyr
                325                 330                 335
Cys Tyr Thr Ala Phe Lys Glu Gln Arg Val Arg Arg Ser Thr Glu Ser
            340                 345                 350
Trp Leu Leu Gly Asp Val Phe Leu Arg Leu Tyr Phe Ser Val Phe Asp
        355                 360                 365
Arg Gly Asn Asp Arg Ile Gly Leu Ala Arg Ala Val
    370                 375                 380
```

<210> SEQ ID NO 47
<211> LENGTH: 1158
<212> TYPE: DNA
<213> ORGANISM: bovidae

<400> SEQUENCE: 47

```
aggaaagaag catgaagtgg cttgtgctcc tctggctagt ggccttctca gagtgtatag    60
tcaaaatacc tctaaggcaa gtgaagacca tgagaaaaac cctcagtgga aaaaacacgc   120
tgaacaattt cttgaaggaa catacttaca gtctgtccca gatttcttct cgtggttcaa   180
atctaactat tcacccactg agaaacatca tggatatgct ctacgtgggt aacatcacca   240
ttggaacacc ccctcaggaa ttccaggttg tctttgacac aggctcatct gacttgtggg   300
tgccctccgt cttttgccaa agtctagcct gtgctacaaa ggttatgttc atacatcttc   360
attcttccac cttccggcat acccaaaagg tcttcaacat caagtacaat actggaagga   420
tgaaaggact tcttgtttat gacactgttc ggattgggga ccttgtaagt actgaccagc   480
cattctgtat aagcctggca gaagttgggt ttgacggtat accttttgat ggtgtcttgg   540
gcttgaacta tccgaacatg tccttctctg gagccatccc catctttgac aacctgaaga   600
atgaaggtgc catttctgag cctgtttttg ccttctactt gagcaaagac aagcgggagg   660
gcagtgtggt gatgtttggt ggggtggacc accgctacta caagggagag ctcaactggg   720
tgccattgat ccaagcgggc ggctggactg tacacgtgga ccgcatctcc atgaaaagaa   780
agattattgc ttgttctgga ggctgcgagg cccttgtgga caccggaaca gcactgatca   840
aaggcccaag aagactggtc aataacatac agaagctcat cggcaccacg ccacggggtt   900
ccaagcacta cgtttcatgt tctgtggtca ataccctgcc ctctattatc ttcaccatca   960
acggcatcaa ctaccggtg ccagcacgag cctacatcct caaggattct gaaagcaact  1020
gctatacaac cttaaagag aacacagtga ggacgtctag agagacctgg atcctgggtg  1080
acgtcttccc gaggctgtat ttctcagtct tgatcgagg aaatgacagg attggcctgg  1140
cacgggcagt gtaactcg                                                1158
```

<210> SEQ ID NO 48
<211> LENGTH: 380
<212> TYPE: PRT
<213> ORGANISM: bovidae

<400> SEQUENCE: 48

```
Met Lys Trp Leu Val Leu Leu Trp Leu Val Ala Phe Ser Glu Cys Ile
  1               5                  10                  15

Val Lys Ile Pro Leu Arg Gln Val Lys Thr Met Arg Lys Thr Leu Ser
             20                  25                  30

Gly Lys Asn Thr Leu Asn Asn Phe Leu Lys Glu His Thr Tyr Ser Leu
         35                  40                  45

Ser Gln Ile Ser Ser Arg Gly Ser Asn Leu Thr Ile His Pro Leu Arg
     50                  55                  60

Asn Ile Met Asp Met Leu Tyr Val Gly Asn Ile Thr Ile Gly Thr Pro
 65                  70                  75                  80

Pro Gln Glu Phe Gln Val Val Phe Asp Thr Gly Ser Ser Asp Leu Trp
                 85                  90                  95

Val Pro Ser Val Phe Cys Gln Ser Leu Ala Cys Ala Thr Lys Val Met
            100                 105                 110

Phe Ile His Leu His Ser Ser Thr Phe Arg His Thr Gln Lys Val Phe
        115                 120                 125

Asn Ile Lys Tyr Asn Thr Gly Arg Met Lys Gly Leu Leu Val Tyr Asp
    130                 135                 140

Thr Val Arg Ile Gly Asp Leu Val Ser Thr Asp Gln Pro Phe Cys Ile
145                 150                 155                 160
```

```
Ser Leu Ala Glu Val Gly Phe Asp Gly Ile Pro Phe Asp Gly Val Leu
                165                 170                 175
Gly Leu Asn Tyr Pro Asn Met Ser Phe Ser Gly Ala Ile Pro Ile Phe
            180                 185                 190
Asp Asn Leu Lys Asn Glu Gly Ala Ile Ser Glu Pro Val Phe Ala Phe
        195                 200                 205
Tyr Leu Ser Lys Asp Lys Arg Glu Gly Ser Val Val Met Phe Gly Gly
    210                 215                 220
Val Asp His Arg Tyr Tyr Lys Gly Glu Leu Asn Trp Val Pro Leu Ile
225                 230                 235                 240
Gln Ala Gly Gly Trp Thr Val His Val Asp Arg Ile Ser Met Lys Arg
                245                 250                 255
Lys Ile Ile Ala Cys Ser Gly Gly Cys Glu Ala Leu Val Asp Thr Gly
            260                 265                 270
Thr Ala Leu Ile Lys Gly Pro Arg Arg Leu Val Asn Asn Ile Gln Lys
        275                 280                 285
Leu Ile Gly Thr Thr Pro Arg Gly Ser Lys His Tyr Val Ser Cys Ser
    290                 295                 300
Val Val Asn Thr Leu Pro Ser Ile Ile Phe Thr Ile Asn Gly Ile Asn
305                 310                 315                 320
Tyr Pro Val Pro Ala Arg Ala Tyr Ile Leu Lys Asp Ser Glu Ser Asn
                325                 330                 335
Cys Tyr Thr Thr Phe Lys Glu Asn Thr Val Arg Thr Ser Arg Glu Thr
            340                 345                 350
Trp Ile Leu Gly Asp Val Phe Pro Arg Leu Tyr Phe Ser Val Phe Asp
        355                 360                 365
Arg Gly Asn Asp Arg Ile Gly Leu Ala Arg Ala Val
    370                 375                 380

<210> SEQ ID NO 49
<211> LENGTH: 1158
<212> TYPE: DNA
<213> ORGANISM: bovidae

<400> SEQUENCE: 49
taggaaagaa gcatgaagtg gcttgtgctc ctcgggctgg tggccttctc agagtgcata     60
gtcaaaatac ctctaaggag agtgaagacc atgagaaaaa ccctcagtgg aaaaaacatc    120
ctgaacaatt tcctgaagga acatgcttac agactgtccc agatttcttc ttgtggctca    180
aatctaactt ttcaccccct tgagaaacat caaggatagg tctacgtggg taacatcacc    240
attggaacac cccctcaaga attccaggtt atctttgaca caggctcatc tgacttgtgg    300
gtgacctccg tcttttgcac cagcccaacc tgttctacac atgttatgtt cagacatttt    360
gattcttcca ccttccggcc taccaaaaag accttcagca tcaactacgg ttctggaagg    420
atgaaggag ttgttgttca tgacacagtt cggattgggg accttgtaag tactgaccag    480
ccatttggtc taagtgtggt ggaacttggg tttgatggta taccttttga tggcgtcatg    540
ggcttgaact accccaaact atccttctct ggagccattc ccatctttga caacctgagg    600
aatcaaggtg ccatttctga gcctgttttt gccttctact tgagcaaaga cgagcaggag    660
ggcagtgtgg tgatgtttgg tggggtggac caccgctact acaagggaga gctcaactgg    720
ataccactga tccaagcagg cgactggagt gtacacatgg acagcatctc catgaaaaga    780
aaggttattg cttgctctgg tggctgcaag gccgttgtgg acaccgggac atcactgatt    840
gaaggcccaa gaagactggt caataacata cagaagctca tcagagccat gccacggggt    900
```

```
tccgagtact acgtttcatg ttctgcggtc aatacccctgc cccctattat cttcaccatc    960
aaaggcatca actacccagt gccagctcaa gcctacatcc tcaaggattc tagaggccac   1020
tgctatacca cctttaaaga ggacagattg agtccaccat ctacagagac ctggatcctg   1080
ggtgacgtct tcctgaggcg gtatttctcg gtctttgatc gaggaaatga caggattggc   1140
ctggcacggg cagtgtaa                                                  1158
```

<210> SEQ ID NO 50
<211> LENGTH: 381
<212> TYPE: PRT
<213> ORGANISM: bovidae

<400> SEQUENCE: 50

```
Met Lys Trp Leu Val Leu Leu Gly Leu Val Ala Phe Ser Glu Cys Ile
  1               5                  10                  15

Val Lys Ile Pro Leu Arg Arg Val Lys Thr Met Arg Lys Thr Leu Ser
             20                  25                  30

Gly Lys Asn Ile Leu Asn Asn Phe Leu Lys Glu His Ala Tyr Arg Leu
         35                  40                  45

Ser Gln Ile Ser Ser Cys Gly Ser Asn Leu Thr Phe His Pro Leu Arg
     50                  55                  60

Asn Ile Lys Asp Arg Leu Tyr Val Gly Asn Ile Thr Ile Gly Thr Pro
 65                  70                  75                  80

Pro Gln Glu Phe Gln Val Ile Phe Asp Thr Gly Ser Ser Asp Leu Trp
                 85                  90                  95

Val Thr Ser Val Phe Cys Thr Ser Pro Thr Cys Ser Thr His Val Met
            100                 105                 110

Phe Arg His Phe Asp Ser Ser Thr Phe Arg Pro Thr Lys Lys Thr Phe
        115                 120                 125

Ser Ile Asn Tyr Gly Ser Gly Arg Met Lys Gly Val Val Val His Asp
    130                 135                 140

Thr Val Arg Ile Gly Asp Leu Val Ser Thr Asp Gln Pro Phe Gly Leu
145                 150                 155                 160

Ser Val Val Glu Leu Gly Phe Asp Gly Ile Pro Phe Asp Gly Val Met
                165                 170                 175

Gly Leu Asn Tyr Pro Lys Leu Ser Phe Ser Gly Ala Ile Pro Ile Phe
            180                 185                 190

Asp Asn Leu Arg Asn Gln Gly Ala Ile Ser Glu Pro Val Phe Ala Phe
        195                 200                 205

Tyr Leu Ser Lys Asp Glu Gln Glu Gly Ser Val Val Met Phe Gly Gly
    210                 215                 220

Val Asp His Arg Tyr Tyr Lys Gly Glu Leu Asn Trp Ile Pro Leu Ile
225                 230                 235                 240

Gln Ala Gly Asp Trp Ser Val His Met Asp Ser Ile Ser Met Lys Arg
                245                 250                 255

Lys Val Ile Ala Cys Ser Gly Gly Cys Lys Ala Val Val Asp Thr Gly
            260                 265                 270

Thr Ser Leu Ile Glu Gly Pro Arg Arg Leu Val Asn Asn Ile Gln Lys
        275                 280                 285

Leu Ile Arg Ala Met Pro Arg Gly Ser Glu Tyr Tyr Val Ser Cys Ser
    290                 295                 300

Ala Val Asn Thr Leu Pro Pro Ile Ile Phe Thr Ile Lys Gly Ile Asn
305                 310                 315                 320
```

```
Tyr Pro Val Pro Ala Gln Ala Tyr Ile Leu Lys Asp Ser Arg Gly His
            325                 330                 335

Cys Tyr Thr Thr Phe Lys Glu Asp Arg Leu Ser Pro Pro Ser Thr Glu
        340                 345                 350

Thr Trp Ile Leu Gly Asp Val Phe Leu Arg Arg Tyr Phe Ser Val Phe
            355                 360                 365

Asp Arg Gly Asn Asp Arg Ile Gly Leu Ala Arg Ala Val
        370                 375                 380

<210> SEQ ID NO 51
<211> LENGTH: 1154
<212> TYPE: DNA
<213> ORGANISM: bovidae

<400> SEQUENCE: 51
aggaaagaag catgaagtgg cttgtggtcc tcggacttgt ggccttctca gagtgcatag    60 tcaaatacc tctaaggaga gtgaagacca tgagaaaagc cctcagtgga aaaaacatgc   120
tgaacaattt cctgaaggaa catgcttaca gactgtccca gatttctttt cgtggctcaa   180
atctaactag tcacccgctg agaaacatca aggatttggt ctacctggct aatatcacca   240
ttggaacacc ccctcaggag ttccaggttt tccttgacac aggctcatct gacttgtggg   300
tgccctctga cttttgcacc agcccaggct gttctaaaca cgttagattc agacatcttc   360
agtcttccac cttccggctt accaataaga ccttcagcat cacctatgga tctgggagaa   420
ttaaaggagt tgttgctcat gacacagttc ggattgggga ccttgtaagc actgaccagc   480
cgttcagtct aagcatggca gaatacgggc ttgagcatat accttttgat ggcatcttgg   540
gcttgaacta ccccaacgta tcttcttctg gagcaatccc tatctttgac aagctgaaga   600
atcaaggtgc catttctgaa cctgtttttg ccttctactt gagcaaagac aagcaggagg   660
gcagtgtggt gatgtttggt ggggtggacc atcgctatta caggggaaag ctcaactggg   720
taccattgat ccaagcggga actggattac acacatgga cagcatctcc attgaaagaa   780
aggttattgc ttgttctgga ggctgcgtgg ccttttgtga tcgggaca gcattcatcg   840 aaggcccaaa accactggtc gataacatgc agaagctcat cagggccaag ccatggcgtt   900
ccaagcacta tgtttcatgt tctgcggtca atacactgcc ctctattacc ttcaccatca   960
acggcatcaa ctacccagtg ccaggtcgag cctacatcct caaggattct agacgccgtt  1020
gctatagcac cttaaagag atcccattga gtccaactac agagttctgg atgctgggtg  1080
acgtcttcct gaggctgtat ttctcagtct ttgatcgagg aaatgacagg attgggctgg  1140
cacgggcagt gtaa                                                    1154

<210> SEQ ID NO 52
<211> LENGTH: 380
<212> TYPE: PRT
<213> ORGANISM: bovidae

<400> SEQUENCE: 52

Met Lys Trp Leu Val Val Leu Gly Leu Val Ala Phe Ser Glu Cys Ile
  1               5                  10                  15

Val Lys Ile Pro Leu Arg Arg Val Lys Thr Met Arg Lys Ala Leu Ser
             20                  25                  30

Gly Lys Asn Met Leu Asn Asn Phe Leu Lys Glu His Ala Tyr Arg Leu
         35                  40                  45

Ser Gln Ile Ser Phe Arg Gly Ser Asn Leu Thr Ser His Pro Leu Arg
     50                  55                  60
```

```
Asn Ile Lys Asp Leu Val Tyr Leu Ala Asn Ile Thr Ile Gly Thr Pro
 65                  70                  75                  80

Pro Gln Glu Phe Gln Val Phe Leu Asp Thr Gly Ser Ser Asp Leu Trp
                 85                  90                  95

Val Pro Ser Asp Phe Cys Thr Ser Pro Gly Cys Ser Lys His Val Arg
            100                 105                 110

Phe Arg His Leu Gln Ser Ser Thr Phe Arg Leu Thr Asn Lys Thr Phe
        115                 120                 125

Ser Ile Thr Tyr Gly Ser Gly Arg Ile Lys Gly Val Val Ala His Asp
    130                 135                 140

Thr Val Arg Ile Gly Asp Leu Val Ser Thr Asp Gln Pro Phe Ser Leu
145                 150                 155                 160

Ser Met Ala Glu Tyr Gly Leu Glu His Ile Pro Phe Asp Gly Ile Leu
                165                 170                 175

Gly Leu Asn Tyr Pro Asn Val Ser Ser Ser Gly Ala Ile Pro Ile Phe
            180                 185                 190

Asp Lys Leu Lys Asn Gln Gly Ala Ile Ser Glu Pro Val Phe Ala Phe
        195                 200                 205

Tyr Leu Ser Lys Asp Lys Gln Glu Gly Ser Val Val Met Phe Gly Gly
    210                 215                 220

Val Asp His Arg Tyr Tyr Arg Gly Lys Leu Asn Trp Val Pro Leu Ile
225                 230                 235                 240

Gln Ala Gly Asn Trp Ile Ile His Met Asp Ser Ile Ser Ile Glu Arg
                245                 250                 255

Lys Val Ile Ala Cys Ser Gly Gly Cys Val Ala Phe Val Asp Ile Gly
            260                 265                 270

Thr Ala Phe Ile Glu Gly Pro Lys Pro Leu Val Asp Asn Met Gln Lys
        275                 280                 285

Leu Ile Arg Ala Lys Pro Trp Arg Ser Lys His Tyr Val Ser Cys Ser
    290                 295                 300

Ala Val Asn Thr Leu Pro Ser Ile Thr Phe Thr Ile Asn Gly Ile Asn
305                 310                 315                 320

Tyr Pro Val Pro Gly Arg Ala Tyr Ile Leu Lys Asp Ser Arg Arg Arg
                325                 330                 335

Cys Tyr Ser Thr Phe Lys Glu Ile Pro Leu Ser Pro Thr Thr Glu Phe
            340                 345                 350

Trp Met Leu Gly Asp Val Phe Leu Arg Leu Tyr Phe Ser Val Phe Asp
        355                 360                 365

Arg Gly Asn Asp Arg Ile Gly Leu Ala Arg Ala Val
    370                 375                 380

<210> SEQ ID NO 53
<211> LENGTH: 1154
<212> TYPE: DNA
<213> ORGANISM: bovidae

<400> SEQUENCE: 53
aggaaagaag catgaagtgg cttgtgctcc tcggtctggt ggccttctca gagtgcatat      60 tcaaatacc tctaaggaga gtgaagacca tgagaaaaac cctcagtgga aaaacatgc      120 tgaacaattt cctgaaggag catccttaca aactgtccca gatttctttt cgtggctcaa     180
atctaaccac tctcccactg aggaacatct gggatatatt ctacataggt accatcacca     240
ttggaacacc ccctcaggaa ttccaggttg tctttgacac agcctcatct gacttgtggg     300
tgccctccat catttgcaac agctcaacct gttctacaca cgttagattc agacatcgtc     360
```

-continued

```
agtcttccac cttccggctt accaataaga cgttcgggat cacgtatgga tctgggagaa      420
tgaaaggagt tgttgttcat gacacagttc ggattgggga ccttgtaagt actgaccagc      480
cattcggtct aagcgtggcg gaatacgggt ttgagggcag aagatttgat ggtgtcttgg      540
gcttgaacta ccccaacata tccttctcta aagccatccc catctttgat aagctgaaga      600
atgaaggtgc catttcagag cctgtttttg ccttctactt gagcaaagac aagcagaagg      660
gcagtgtggt gatgtttggt ggggtggacc accgctacta caaaggagag ctcaactggg      720
taccattgat ccgagcgggt gactggagtg tacacgtaga ccgcatcacc atgaaaggag      780
aggttattgg ttgttctgat ggctgcacgg ccatggtgga caccgggtca tcaaatatcc      840
aaggcccagg aagagtgatc gataacatac acaagctcat tggtgccaca ccacggggtt      900
ccaagcacta cgtttcatgt tctgcggtca gtgctctgcc ctctgttgtc ttccaccatca     960 atggcatcaa ctacccagtg ccagctcgag cctacgtcct caaggatttt acaggcaact     1020
gctacaccac ctttaaagag aaaagggtaa ggagatctac ggagttctgg atcctgggtg     1080
aagccttcct gaggctgtat ttctcggtct ttgatcgagg aaatgacagg attggcctgg     1140
cacgggcagt gtaa                                                       1154
```

<210> SEQ ID NO 54
<211> LENGTH: 380
<212> TYPE: PRT
<213> ORGANISM: bovidae

<400> SEQUENCE: 54

```
Met Lys Trp Leu Val Leu Leu Gly Leu Val Ala Phe Ser Glu Cys Ile
  1               5                  10                  15

Phe Lys Ile Pro Leu Arg Arg Val Lys Thr Met Arg Lys Thr Leu Ser
             20                  25                  30

Gly Lys Asn Met Leu Asn Asn Phe Leu Lys Glu His Pro Tyr Lys Leu
         35                  40                  45

Ser Gln Ile Ser Phe Arg Gly Ser Asn Leu Thr Thr Leu Pro Leu Arg
     50                  55                  60

Asn Ile Trp Asp Ile Phe Tyr Ile Gly Thr Ile Thr Ile Gly Thr Pro
 65                  70                  75                  80

Pro Gln Glu Phe Gln Val Val Phe Asp Thr Ala Ser Ser Asp Leu Trp
                 85                  90                  95

Val Pro Ser Ile Ile Cys Asn Ser Thr Cys Ser Thr His Val Arg
            100                 105                 110

Phe Arg His Arg Gln Ser Ser Thr Phe Arg Leu Thr Asn Lys Thr Phe
        115                 120                 125

Gly Ile Thr Tyr Gly Ser Gly Arg Met Lys Gly Val Val His Asp
    130                 135                 140

Thr Val Arg Ile Gly Asp Leu Val Ser Thr Asp Gln Pro Phe Gly Leu
145                 150                 155                 160

Ser Val Ala Glu Tyr Gly Phe Glu Gly Arg Arg Phe Asp Gly Val Leu
                165                 170                 175

Gly Leu Asn Tyr Pro Asn Ile Ser Phe Ser Lys Ala Ile Pro Ile Phe
            180                 185                 190

Asp Lys Leu Lys Asn Glu Gly Ala Ile Ser Glu Pro Val Phe Ala Phe
        195                 200                 205

Tyr Leu Ser Lys Asp Lys Gln Lys Gly Ser Val Val Met Phe Gly Gly
    210                 215                 220
```

```
Val Asp His Arg Tyr Tyr Lys Gly Glu Leu Asn Trp Val Pro Leu Ile
225                 230                 235                 240

Arg Ala Gly Asp Trp Ser Val His Val Asp Arg Ile Thr Met Lys Gly
            245                 250                 255

Glu Val Ile Gly Cys Ser Asp Gly Cys Thr Ala Met Val Asp Thr Gly
        260                 265                 270

Ser Ser Asn Ile Gln Gly Pro Gly Arg Val Ile Asp Asn Ile His Lys
        275                 280                 285

Leu Ile Gly Ala Thr Pro Arg Gly Ser Lys His Tyr Val Ser Cys Ser
    290                 295                 300

Ala Val Ser Ala Leu Pro Ser Val Val Phe Thr Ile Asn Gly Ile Asn
305                 310                 315                 320

Tyr Pro Val Pro Ala Arg Ala Tyr Val Leu Lys Asp Phe Thr Gly Asn
                325                 330                 335

Cys Tyr Thr Thr Phe Lys Glu Lys Arg Val Arg Arg Ser Thr Glu Phe
            340                 345                 350

Trp Ile Leu Gly Glu Ala Phe Leu Arg Leu Tyr Phe Ser Val Phe Asp
        355                 360                 365

Arg Gly Asn Asp Arg Ile Gly Leu Ala Arg Ala Val
    370                 375                 380

<210> SEQ ID NO 55
<211> LENGTH: 1320
<212> TYPE: DNA
<213> ORGANISM: bovidae
<220> FEATURE:
<221> NAME/KEY: modified_base
<222> LOCATION: (1196)..(1196)
<223> OTHER INFORMATION: N = A, C G, or T/U

<400> SEQUENCE: 55
gtcgacggaa agaagcatga agtgggttgt gctccttggg ctggtggcct tctcagagtg      60
catagtcaaa atacctctaa ggcgagtgaa gaccatgaga aaaaccctca gtggtaaaaa     120
catgctgaac aatttcttga aggagcatgg taacagattg tccaagattt cttttcgtgg     180
ctcaaatcta actactctcc cgctgagaaa catcgaggat ttgatgtacg tgggtaacat     240
caccattgga acacccccac aggaattcca ggttgtcttt gatacaggct catctgactt     300
ttgggtgccc tccgactttt gcactagtcc agactgtatt acacacgtta gattcagaca     360
acatcagtct tccaccttcc ggcctaccaa taagaccttc agcatcacct atggatctgg     420
gagaatgaga ggagttgttg ttcatgacac agttcggatt ggggaccttg taagtactga     480
ccagccgttc ggtctaagcg tgtcagaata cgggtttaag gacagagctt atgatggcat     540
cctgggcttg aactaccccg acgaatcctt ctctgaagcc atccccatct ttgacaagct     600
aaagaatgaa ggtgccattt ctgagcctat ttttgccttc tacttgagca aaaaaaagcg     660
ggagggcagt gtggtgatgt tggtggggt ggaccaccgc tactacaagg gagagctcaa     720
ctgggtacca ttgatcgaag agggtgactg gagtgtacgc atggacggca tctccatgaa     780
aacaaaggta gttgcttgtt ctgacggctg cgaggctgtt gttgacactg gacatcact     840 gataaaaggc ccaagaaaac tggtcaataa aatacagaag ctcattggtg ccacgccacg     900
gggttccaag cactacgttt attgttctgc ggtcaatgct ctgccctcta ttatcttcac     960
catcaatggc atcaactacc cagtgccagc tcgagcctac attctcaagg attctagagg    1020
ccgctgctat accgccttta aaagcaacg attcagttca tctacagaga cctggctcct    1080
gggtgacgcc ttcctgaggg tgtatttctc ggtctttgat cgaggaaatg caggattgg    1140
```

```
cctggcacag gcagtgtaaa tgcttggagt ggttcaagaa tcagtaaggc cgcttntaac    1200
acacactcac tcacactagg gcactcctgc ccaggatggt ggtgaactgt atttggtggt    1260
ctgtacaccc tattctcagt gaagaataaa cggtttcact cttaatggtg ctgaaaaaaa    1320
```

<210> SEQ ID NO 56
<211> LENGTH: 380
<212> TYPE: PRT
<213> ORGANISM: bovidae

<400> SEQUENCE: 56

```
Met Lys Trp Val Val Leu Leu Gly Leu Val Ala Phe Ser Glu Cys Ile
 1               5                  10                  15

Val Lys Ile Pro Leu Arg Arg Val Lys Thr Met Arg Lys Thr Leu Ser
            20                  25                  30

Gly Lys Asn Met Leu Asn Asn Phe Leu Lys Glu His Gly Asn Arg Leu
        35                  40                  45

Ser Lys Ile Ser Phe Arg Gly Ser Asn Leu Thr Thr Leu Pro Leu Arg
    50                  55                  60

Asn Ile Glu Asp Leu Met Tyr Val Gly Asn Ile Thr Ile Gly Thr Pro
65                  70                  75                  80

Pro Gln Glu Phe Gln Val Val Phe Asp Thr Gly Ser Ser Asp Phe Trp
                85                  90                  95

Val Pro Ser Asp Phe Cys Thr Ser Pro Asp Cys Ile Thr His Val Arg
            100                 105                 110

Phe Arg Gln His Gln Ser Ser Thr Phe Arg Pro Thr Asn Lys Thr Phe
        115                 120                 125

Ser Ile Thr Tyr Gly Ser Gly Arg Met Arg Gly Val Val His Asp
    130                 135                 140

Thr Val Arg Ile Gly Asp Leu Val Ser Thr Asp Gln Pro Phe Gly Leu
145                 150                 155                 160

Ser Val Ser Glu Tyr Gly Phe Lys Asp Arg Ala Tyr Asp Gly Ile Leu
                165                 170                 175

Gly Leu Asn Tyr Pro Asp Glu Ser Phe Ser Glu Ala Ile Pro Ile Phe
            180                 185                 190

Asp Lys Leu Lys Asn Glu Gly Ala Ile Ser Glu Pro Ile Phe Ala Phe
        195                 200                 205

Tyr Leu Ser Lys Lys Arg Glu Gly Ser Val Val Met Phe Gly Gly
    210                 215                 220

Val Asp His Arg Tyr Tyr Lys Gly Glu Leu Asn Trp Val Pro Leu Ile
225                 230                 235                 240

Glu Glu Gly Asp Trp Ser Val Arg Met Asp Gly Ile Ser Met Lys Thr
                245                 250                 255

Lys Val Val Ala Cys Ser Asp Gly Cys Glu Ala Val Val Asp Thr Gly
            260                 265                 270

Thr Ser Leu Ile Lys Gly Pro Arg Lys Leu Val Asn Lys Ile Gln Lys
        275                 280                 285

Leu Ile Gly Ala Thr Pro Arg Gly Ser Lys His Tyr Val Tyr Cys Ser
    290                 295                 300

Ala Val Asn Ala Leu Pro Ser Ile Ile Phe Thr Ile Asn Gly Ile Asn
305                 310                 315                 320

Tyr Pro Val Pro Ala Arg Ala Tyr Ile Leu Lys Asp Ser Arg Gly Arg
                325                 330                 335

Cys Tyr Thr Ala Phe Lys Lys Gln Arg Phe Ser Ser Thr Glu Thr
            340                 345                 350
```

-continued

```
Trp Leu Leu Gly Asp Ala Phe Leu Arg Val Tyr Phe Ser Val Phe Asp
        355                 360                 365

Arg Gly Asn Gly Arg Ile Gly Leu Ala Gln Ala Val
    370                 375                 380
```